US005639671A

United States Patent [19]

Bogart et al.

[11] Patent Number: 5,639,671

[45] Date of Patent: Jun. 17, 1997

[54] METHODS FOR OPTIMIZING OF AN OPTICAL ASSAY DEVICE

[75] Inventors: Gregory R. Bogart, Fort Collins; Jeffrey B. Etter, Boulder, both of Colo.

[73] Assignee: Biostar, Inc., Boulder, Colo.

[21] Appl. No.: 412,600

[22] Filed: Mar. 28, 1995

Related U.S. Application Data

[63] Continuation of Ser. No. 76,319, Jun. 10, 1993, abandoned, which is a continuation-in-part of Ser. No. 923,048, Jul. 31, 1992, abandoned, which is a continuation-in-part of Ser. No. 873,097, Apr. 24, 1992, abandoned, which is a continuation-in-part of Ser. No. 408,291, Sep. 18, 1989, abandoned.

[51] Int. Cl.⁶ .................. G01N 33/543; G01N 33/545; G01N 33/547

[52] U.S. Cl. .................. 436/518; 359/581; 359/585; 359/586; 359/589; 422/55; 422/57; 422/82.05; 422/82.11; 427/162; 427/164; 427/165; 427/166; 427/167; 427/250; 427/255; 427/337; 427/338; 427/404; 427/419.1; 427/419.2; 435/4; 435/808; 436/164; 436/165; 436/524; 436/532

[58] Field of Search .................. 422/55, 57, 82.05, 422/82.11; 427/162, 164, 165–167, 250, 255, 337, 338, 404, 419.1, 419.2, 419.7; 359/581, 585, 586, 589; 435/808, 4; 436/164, 165, 518, 524, 525, 527, 805, 532

[56] References Cited

U.S. PATENT DOCUMENTS

| | | | |
|---|---|---|---|
| 3,002,861 | 10/1961 | Suchoff | 427/79 |
| 3,530,013 | 9/1970 | Smyth et al. | 148/6.3 |
| 3,530,159 | 9/1970 | Guinet et al. | 260/448.2 |
| 3,554,787 | 1/1971 | Plymale | 117/72 |
| 3,630,792 | 12/1971 | Smyth et al. | 148/6.3 |
| 3,667,926 | 6/1972 | Green et al. | 65/60 |
| 3,839,307 | 10/1974 | Schmifg | 260/86.1 |
| 3,926,564 | 12/1975 | Giaever | 23/259 |
| 3,960,488 | 6/1976 | Giaever | 23/230 B |
| 3,979,184 | 9/1976 | Giaever | 23/253 TP |
| 4,054,646 | 10/1977 | Giaever | 424/12 |
| 4,090,849 | 5/1978 | Healy et al. | 23/253 TP |
| 4,113,757 | 9/1978 | Kay | 260/429.5 |
| 4,208,506 | 6/1980 | Deichert et al. | 528/32 |
| 4,332,476 | 6/1982 | Stenberg et al. | 356/369 |
| 4,357,142 | 11/1982 | Schall et al. | 23/230 B |
| 4,363,634 | 12/1982 | Schall | 23/230 B |
| 4,369,268 | 1/1983 | Graziano et al. | 523/435 |
| 4,421,896 | 12/1983 | Dorman | 525/54.1 |
| 4,444,862 | 4/1984 | Yagi et al. | 430/67 |
| 4,497,899 | 2/1985 | Armstrong et al. | 436/510 |
| 4,497,900 | 2/1985 | Abram et al. | 436/511 |
| 4,507,466 | 3/1985 | Dewald et al. | 528/332 |
| 4,508,832 | 4/1985 | Carter et al. | 436/517 |
| 4,524,126 | 6/1985 | Marinace et al. | 430/311 |
| 4,535,007 | 8/1985 | Cannady | 427/226 |
| 4,558,012 | 12/1985 | Nygren et al. | 436/501 |
| 4,568,737 | 2/1986 | Dewald et al. | 528/332 |
| 4,587,329 | 5/1986 | Dewald et al. | 528/363 |
| 4,588,120 | 5/1986 | Frost et al. | 227/76 |
| 4,647,207 | 3/1987 | Bjork et al. | 356/369 |
| 4,647,544 | 3/1987 | Nicoli et al. | 436/518 |
| 4,655,595 | 4/1987 | Bjork et al. | 356/369 |
| 4,672,024 | 6/1987 | Giaever et al. | 430/396 |
| 4,818,611 | 4/1989 | Arai et al. | 428/364 |
| 4,820,649 | 4/1989 | Kawaguchi et al. | 436/501 |
| 4,876,208 | 10/1989 | Gustafson et al. | 436/531 |
| 4,886,761 | 12/1989 | Gustafson et al. | 436/518 |
| 4,946,920 | 8/1990 | Vaahs et al. | 528/33 |
| 4,959,303 | 9/1990 | Houts et al. | 435/7 |
| 5,030,561 | 7/1991 | Donahue et al. | 435/7.36 |
| 5,030,702 | 7/1991 | Vaahs | 528/33 |
| 5,047,325 | 9/1991 | Gilbert et al. | 435/7.36 |
| 5,075,220 | 12/1991 | Pronovost | 435/7.36 |
| 5,089,387 | 2/1992 | Tsay et al. | 435/6 |
| 5,104,692 | 4/1992 | Belmares | 427/164 |
| 5,418,136 | 5/1995 | Miller et al. | 436/825 |

FOREIGN PATENT DOCUMENTS

| | | |
|---|---|---|
| 0261642 | 3/1988 | European Pat. Off. . |
| 0322549 | 7/1989 | European Pat. Off. . |
| 0347138 | 12/1989 | European Pat. Off. . |
| 2191744 | 1/1974 | France . |
| 2245809 | 5/1973 | Germany . |
| 81144541 | 11/1981 | Japan . |
| 6378051 | 4/1988 | Japan . |
| 6378052 | 4/1988 | Japan . |
| 2065298 | 6/1981 | United Kingdom . |
| 8909937 | 10/1989 | WIPO . |
| 9011525 | 10/1990 | WIPO . |
| 9104491 | 4/1991 | WIPO . |
| 9106862 | 5/1991 | WIPO . |
| 9203730 | 3/1992 | WIPO . |

OTHER PUBLICATIONS

Sandström et al., *Applied Optics*, vol. 24, No. 4, 15 Feb. 1985, pp. 472–479.

Handbook of Optics, Walter G. Driscoll, and William Vaughan, editors, McGraw–Hill Book Co., NY, 1978, pp. 8–48 to 8–49, Table 3.

Polymer Surfaces and Interfaces, edited by W.J. Feast and H.S. Munro, John Wiley and Sons, NY, p. 212, 1987.

C. Fredrik Mandenires and K. Mosbach, 170 Anal. Biochem. 68, 1988.

Neal and Fane, *Journal of Physics E: Scientific Instruments*, "Ellipsometry and its Applications to Surface Examination", 6:409–416, (1973).

(List continued on next page.)

*Primary Examiner*—Christopher L. Chin
*Attorney, Agent, or Firm*—Lyon & Lyon

[57] ABSTRACT

Method for optimizing an optical assay device for an analyte, including the steps of: providing a substrate having a chosen thickness of an optically active layer thereon; providing an attachment layer of a chosen thickness on the optical coating; providing a receptive layer of a chosen thickness for the analyte, wherein at least one of the thicknesses of the optically active layer, attachment layer and receptive layer is varied to provide a plurality of thicknesses of that layer; contacting analyte with the receptive layer under conditions in which an increase in mass on the receptive layer results; and determining the optical thickness of the layer.

5 Claims, 23 Drawing Sheets

OTHER PUBLICATIONS

Azzam, *Journal of Physics E. Scientific Instruments*, "Two–Reflection Null Ellipsometer Without a Compensator", 9:569–572, (1976).

Humphreys and Parsons, *J. Electroanal. Chem.*, "Ellipsometry of DNA Adsorbed at Mercury Electrodes a Preliminary Study", 75:427–436, (1977).

Zaghloul, *Optics Communications*, "Modified O'Bryan Ellipsometer (MOE) for Film–Substrate Systems", 27;1–3, (1878).

Stenberg et al., *Materials Science and Engineering*, "A New Ellipsometric Method for Measurements on Surfaces and Surface Layers", 42:65–69, (1980).

Stenberg and Nygren, *Analytical Biochemistry*, "A Receptor–Ligand Reaction Studied by a Novel Analytical Tool—The Isoscope Ellipsometer", 127:183–192, (1982).

Nygren et al., *Journal of Immunological Methods*, "Direct Visual Detection of Protein Antigen: Importance of Surface Concentration", 59:145–149, (1983).

Sandercock, *J. Phys. E: Sci. Instrum.*, "Film Thickness Monitor Based on White Light Interference", 16:866–870, (1983).

Mandenius et al., *Analytical Biochemistry*, "The Interaction of Proteins and Cells with Affinity Ligands Covalently Coupled to Silicon Surfaces as Monitored by Ellipsometry", 137:106–114, (1984).

Arwin, H. and Aspnes, D.E., "Determination of Optical Properties of Thin Organic Films By Spectroellipsometry", pp. 195–207, (1985).

Arwin, H., "Optical Properties of Thin Layers of Bovine Serum Albumin, v–Globulin, and Hemoglobin". (1985).

Jonsson, U. et al., *Journal of Colloid and Interface Science*, "Adsorption of Immunoglobulin G, Protein A, and Fibronectinin the Submonolayer Region Evaluated by a Combined Study of Ellipsometry and Radiotracer Techniques", 103:360–372, (1985).

Lee, J–J. and Fuller, G.G., *Journal of Colloid and Interface Science*, "Adsorption and Desorption of Flexible Polymer Chains in Flowing Systems", 103:569–577, (1985).

Nygren, H. and Stenberg, M., *Journal of Immunological Methods*, "Calibration by Ellipsometry of the Enzyme–Linked Immunosorbent Assay", 80:15–24, (1985).

Nygren, H. and Stenberg, M., *Journal of Colloid and Interface Science*, "Kinetics of Antibody–Binding to Surface–Immobilized Antigen: Influence of Mass Transport on the Enzyme–Linked Immunosorbent Assay (ELISA)", 107:560–566, (1985).

Ribarsky, M.W., *Handbook of Optical Constants of Solids*, "Titanium Dioxide (TiO2) (Rutile)", pp. 795–804, (1985).

Elwing, H. et al., *Eur. J. Biochem.*, "Complement Deposition from Human Sera on Silicon Surfaces Studied in Situ by Ellipsometry: The Influence of Surface Wettability", 156: 359–365, (1986).

Nygren, H. et al., *Journal of Immunological Methods*, "Determination by Ellipsometry of the Affinity of Monoclonal Antibodies", 92:219–225, (1986).

Golander, C–G. and Kiss, E., *Journal of Colloid and Interface Science*, "Protein Adsorption on Functionalized and ESCA–Characterized Polymer Films Studied by Ellipsometry", 121:241–253, (1988).

Werthen, M. and Nygren, H., *Journal of Immunological Methods*, "Effect of Antibody Affinity on the Isotherm of Antibody Binding to Surface–Immobilized Antigen", 115:71–78, (1988).

*Analytical Biochemistry*, vol. 145, pp. 106–112 (1985).

Biosensors, vol. 1, 1985, J.F. Place et al., "Opto–Electronic Immunosensors: A Review of Optical Immuno–assay at Continuous Surfaces", pp. 321–353. See the abstract.

Photonics Spectra, Feb. 1988, J. Hanlin, "Thin Films: New Medical Detectives", see entire document.

Giaver and Laffin, "Visual Detection of Hepatitis B Antigen", 71 *Proc. Nat. Acad. Sci USA*, 4533, Nov. 1974.

+

⇩

+

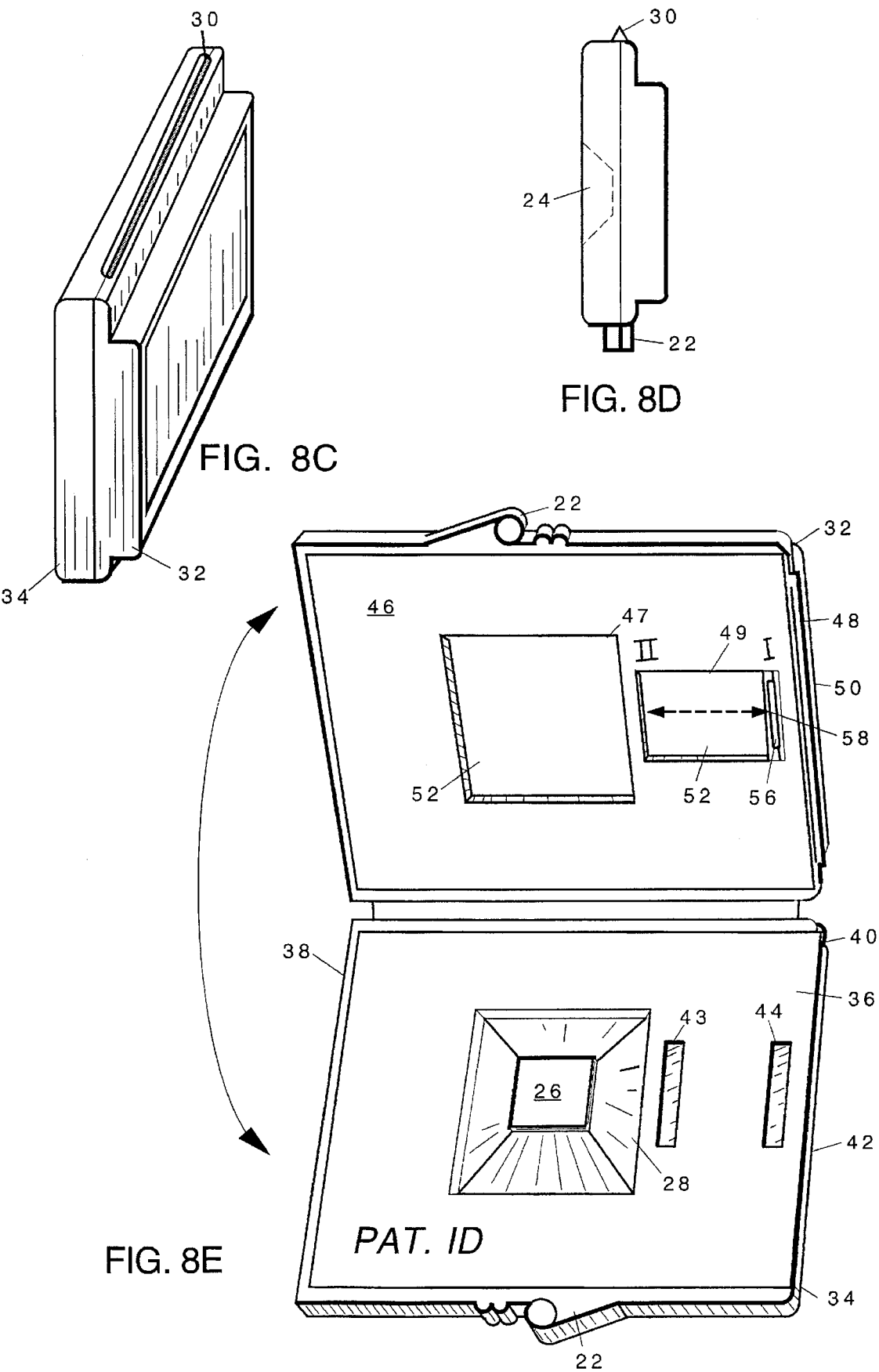

Negative   Positive

METHODS FOR OPTIMIZING OF AN OPTICAL ASSAY DEVICE

RELATED APPLICATIONS

This application is a continuation of Bogart et al., U.S. application No. 08/076,319, filed Jun. 10, 1993, now abandoned, which is a continuation-in-part of Bogart et al., U.S. application No. 07/923,048, filed Jul. 31, 1992, now abandoned, which is a continuation-in-part of Garret Moddel et al., U.S. application No. 07/873,097, filed Apr. 24, 1992, now abandoned, which is a continuation-in-part of Garret Moddel et al., U.S. application No. 07/408,291, filed Sep. 18, 1989, now abandoned. All of the above-noted applications (including drawings) are made a part hereof, and are incorporated herein by reference.

FIELD OF THE INVENTION

The present invention relates to devices which produce a detectable attenuation of the spectral characteristic of light impinging on the device by thin film phenomenon.

BACKGROUND OF THE INVENTION

Sandström et al., 24 *Applied Optics* 472, 1985, describe use of an optical substrate of silicon with a layer of silicon monoxide and a layer of silicon dioxide formed as dielectric films. They indicate that a change in film thickness changes the properties of the optical substrate to produce different colors related to the thickness of the film. That is, the thickness of the film is related to the color observed and a film provided on top of an optical substrate may produce a visible color change. They indicate that a mathematical model can be used to quantitate the color change, and that "[c]alculations performed using the computer model show that very little can be gained in optical performance from using a multilayer structure ... but a biolayer on the surface changes the reflection of such structures very little since the optical properties are determined mainly by the interfaces inside the multilayer structure . . . The conclusion is, somewhat surprisingly, that the most sensitive system for detection of biolayers is a single layer coating, while in most other applications performance can be improved by additional dielectric layers."

Sandström et al., go on to indicate that slides formed from metal oxides on metal have certain drawbacks, and that the presence of metal ions can also be harmful in many biochemical applications. They indicate that the ideal top dielectric film is a 2–3 nm thickness of silicon dioxide which is formed spontaneously when silicon monoxide layer is deposited in ambient atmosphere, and that a 70–95 nm layer of silicon dioxide on a 40–60 nm layer of silicon monoxide can be used on a glass or plastic substrate. They also describe formation of a wedge of silicon monoxide by selective etching of the silicon monoxide, treatment of the silicon dioxide surface with dichlorodimethylsilane, and application of a biolayer of antigen and antibody. From this wedge construction they were able to determine film thickness with an ellipsometer, and note that the "maximum contrast was found in the region about 65 nm where the interference color changed from purple to blue." They indicate that the sensitivity of such a system is high enough for the detection of protein antigen by immobilized antibodies. They conclude "the designs given are sensitive enough for a wide range of applications. The materials, i.e., glass, silicon, and silicon oxides, are chemically inert and do not affect the biochemical reaction studied. Using the computations above it is possible to design slides that are optimized for different applications. The slides can be manufactured and their quality ensured by industrial methods, and two designs are now commercially available. It is our hope that these sensitive, versatile, and inexpensive tools will further the development of simplified methods in immunology and biochemistry." [Citation omitted.]

Nygren et al., 59 *J. Immunol. Methods* 145, 1983, describe a system similar to that described above, in which specific anti-human serum albumin (HSA) antibodies are used to detect HSA. FIG. 2 of this publication indicates that $10^{-5}$ mg/ml of HSA can be detected with a 16 hour incubation, but that $10^{-6}$ mg/ml could not be detected in this system. They also state "[a]fter 72 hour of incubation time, the detection limit was lower (down to 1 ng/ml), however, the reaction was then more sensitive to unspecific reactions, giving rise to eventually occurring positive controls."

Nygren et al., U.S. Pat. No. 4,558,012 describe a similar system except that the overall array of layers is adapted to reduce reflection in respect to non-monochromatic or white light in the wavelength range of 525–600 nM.

SUMMARY OF THE INVENTION

This invention features improved devices, and methods for using such devices, for detecting the presence or amount of an analyte of interest within a sample. In contrast to prior devices, those of the present invention allow detection of extremely small quantities of analyte in a sample, in amounts as low as 0.1 nM, 0.1 ng/ml, or $2 \times 10^3$ organisms or even as low as 50 fg in a rapid assay lasting only a few minutes. Total assay times may vary from one hour to a few minutes from the initiation of the assay protocol (i.e., from the time that the analyte containing sample is contacted with the device). Indeed, the devices of the present invention permit detection of over 30% more true positive samples than prior devices and methods have previously permitted in certain assays, such as an assay for Streptococcus A antigen. The invention is based upon the finding of better structures in the present device compared to those described by Sandström and co-workers (see above), the details of which are provided below. Such devices can be used in an instrumented format. They are also useful when provided in a format in which a visual color change can be observed, especially when that visual color change is extremely easy to interpret, e.g., as a change from a gold background to a dark purple or blue color.

Thus, in a first aspect, the invention features a device for detecting the amount or presence of an analyte of interest. The device includes a substrate which has an optically active surface exhibiting a first color in response to light impinging thereon. This first color is defined as a spectral distribution of the emanating light. The substrate also exhibits a second color which is different from the first color (by having a combination of wavelengths of light which differ from that combination present in the first color, or having a different spectral distribution, or by having an intensity of one or more of those wavelengths different from those present in the first color). The second color is exhibited in response to the same light when the analyte is present on the surface. Such a device provides a sensitive method for detecting an amount of 0.1 ng, 0.1 nM, 0.1 ng/ml, 50 fg, or $2 \times 10^3$ organisms containing the analyte of interest. Indeed, in preferred embodiments, the amount detected can be considerably smaller by as much as 10, 100 or even 1000 fold. The change from one color to another can be measured either by use of an instrument, or by eye. Such sensitive detection is a significant advance over the devices described by Sandstrom and Nygren, supra, and allow use of the devices in commercially viable and competitive manner. Indeed, the sensitivity of the devices so far surpasses existing techniques that existent "gold" standards of detection are exceeded by devices and methods of this invention.

An "optically active surface" is a surface that participates in the generation of an optical effect such that the light impinging upon that surface is in some way altered. Such optically active surfaces may be adapted to respond not only to polychromatic light (e.g., white light) but also to monochromatic light (e.g., laser light, which may be inherently polarized). Devices of this invention preferably produce a color signal that strongly contrasts the background interference color of the unreacted test surface and a reacted surface. The test surface may produce various shades or intensities of color that correspond to a semi-quantitative measurement of the analyte concentration in the sample, and may be visually or instrumentally measured. Such devices allow the quantitative, instrumented analysis of thin film assay systems.

In one embodiment, the optically active surface has a non-specular surface, or is provided with a transparent layer having a non-specular surface through which the optically active surface may be viewed. This embodiment is useful in the invention since it makes the angle from which the surface is viewed less important. The term "non-specular" is meant to indicate that the surface does not act mirror-like (specular), but provides a diffuse response to light. Generally, it includes an irregular surface with between 100 nm and 100 μm variations in height. The primary advantage is that a diffuse reflection allows the color change to be visible over a broad range of angles relative to the incident light.

In yet further embodiments, the substrate may include an interference film which may be formed from silicon nitride, silicon oxides, titanium dioxide, silicon oxynitride or cadmium sulfide and the like. This film acts to cause incident light to undergo interference such that a specific color is produced on the surface of the substrate. This film interacts with other layers on the substrate to ensure that a color change or wavelength intensity change is observed when the analyte is present on the device. In more preferred embodiments, an attachment layer is provided which allows bonding of a receptor molecule specific for the analyte of interest to be bound to the device. It is important in the invention that this attachment layer allow attachment of sufficient of the receptor material so that a signal is produced on the device. In other related embodiments, the device may be used in a manner in which, once the analyte of interest is bonded to the attachment layer, other layers may be deposited on the device in an analyte-specific manner to produce the color signal or a more intense color signal.

While it may be preferred to produce a device which can be analyzed by eye, the invention also includes those devices which can be used with an ellipsometer, a comparison ellipsometer, a reflectometer, a profilometer or modified ellipsometers as described in this application, and the like.

In other related aspects (described in more detail below), the invention features methods for use of the above devices, specific devices adapted for use in the invention, and methods for optimizing devices of the invention by formation of a substrate having an optically active surface with varying thicknesses of each of the component layers such that the optimal thickness of each layer can be readily determined.

Specifically, the invention features similar devices in which the substrate has an attachment layer formed from a chemical selected from the group consisting of dendrimers, star polymers, molecular self-assembling polymers, polymeric siloxanes, and film forming latexes; the substrate itself is formed from a material selected from the group consisting of monocrystalline silicon, a amorphous silicon on glass, amorphous silicon on plastic, a ceramic, polycrystalline silicon, and composites of these materials; and the substrate may have an optical thin film formed from a material selected from the group consisting of silicon nitride, silicon/ silicon dioxide composites, silicon oxynitride, titanium dioxide, titanates, diamond, oxides of zirconium, and silicon carbide.

In particularly preferred embodiments, the second color is discernable in less than one hour after contact of the analyte with the device; the response to light is observed when the analyte is present on the surface in any amount selected from 0.1 nM, 0.1 ng/ml, 50 fg, and $2\times10^3$ organisms having the analyte; the surface is specular, or non-specular, or a transparent layer having a non-specular surface is provided for viewing of the optically active surface; the substrate is selected from the group consisting of a solid support, a flexible support, a plastic, a glass, a metal and a non-metal; the substrate is light reflective or light transmissive; the light is monochromatic light, polychromatic light, ultraviolet light, or infrared light; the analyte is selected from the group consisting of rheumatoid factor; IgE antibodies specific for Birch pollen; carcinoembryonic antigen; streptococcus Group A antigen; vital antigens; antigens associated with autoimmune disease, allergens, a tumor or an infectious microorganism; streptococcus Group B antigen, H/V I or HIV II antigen; or host response (antibodies) to said virus; antigens specific to RSV or host response (antibodies) to the virus; an antibody; antigen; enzyme; hormone; polysaccharide; protein; lipid; carbohydrate; drug or nucleic acid; is derived from the causative organisms for meningitis; Neisseria meningitides groups A, B, C, Y and $W_{135}$, Streptococcus pneumoniae, E. coli K1, Haemophilus influenza type B; an antigen derived from microorganisms; a hapten, a drug of abuse (including drugs which are unlawful to use without a permit or license); a therapeutic drug; an environmental agents; and antigens specific to Hepatitis, the non-specular surface has a reading of between 2700 and 3295 with a profilometer, wherein this value represents the RMS roughness divided by the average peak height of the surface texture, and whose specular reflectances measured by an HeNe laser light source is less than about 5%; the substrate is selected from the group consisting of glass, and plastic, comprising a layer of amorphous silicon on its surface, whereby an optically active surface is produced; the optically active surface includes monocrystalline silicon or metal; the substrate is metal further having a layer of amorphous silicon; a receptor layer receptive to analyte is provided with a; specific binding partner for the analyte; the receptor layer is formed from material selected from the group consisting of antigens, antibodies, oligonucleotides, chelators, enzymes, bacteria, bacterial pili, bacterial flagellar materials, nucleic acids, polysaccharides, lipids, proteins, carbohydrates, metals, viruses, hormones and receptors for said materials; and the first color is golden in appearance and the second color is purple or blue in appearance to the eye.

In other preferred embodiments, the device is configured and arranged to provide a symbol detectable by eye in response to polychromatic light; and the optical film is coated on the device in a thickness between 480 Å and 520 Å; and the analyte of interest is sandwiched between the receptive material and a secondary binding reagent.

In another aspect, the invention features a device for use in an optical assay for an analyte, which includes a multilayered substrate formed with a layer of base material, a conducting metal layer of aluminum, chromium, or a transparent conducting oxide, and a layer of amorphous silicon, wherein the metal layer is positioned adjacent the amorphous silicon. Alternatively, the device has a multi-layered substrate with a layer of base material (any solid material on which optically active layers may be applied), and a layer of amorphous silicon adjacent the base material. In preferred embodiments, the device has an anti-reflective layer attached to the upper substrate surface, having an optical material able to attach to the upper substrate surface, and a receptive material positioned most remote from the upper substrate surface and selected from materials specific to bind the analyte of interest in a fluid to be tested; the base material is selected from any of the group consisting of glass, fused silica, plastics, semiconductors, ceramics, and metals, and may be either rigid or flexible; and an attachment layer is interposed between the optical material and the receptive material.

In yet other aspects, the invention features an optical assay device for detection of an analyte formed with a substrate selected from glass, plastic, silicon and amorphous silicon, an anti-reflective layer selected from silicon nitride, composite of silicon/silicon dioxide, titanates, silicon carbide, diamond, cadmium sulfide, and titanium dioxide, an attachment layer selected from a polymeric silane, polymeric siloxanes, film forming latex, or a dendrimer, and a specific binding layer for the analyte.

In preferred embodiments, the amorphous silicon layer has a thickness between about 900 and 1100 nm; an aluminum layer of between about 1800 and 2200 Å thickness is provided on the glass; the silicon nitride, composites of silicon/silicon dioxide, titanates, or titanium dioxide layer has a thickness between about 480 and 515 Å; the attachment layer is an aminoalkyl-T-structured branched siloxane of between about 90 and 110 Å thickness; and the receptive material is an antibody layer of between about 30 and 60 Å thickness.

In more preferred embodiments, the substrate is configured and arranged so that any change from the first color to the second color is indicated by the output of an instrument, such as an ellipsometer; the change is in the intensity of light reflected or transmitted from the surface; the impinging light is reflected by the device and the reflected light is elliptically or linearly polarized, monochromatic, polychromatic, unpolarized, visible, UV, or IR, or any combination thereof; the substrate supports an optically active surface or is optically active itself.

In another aspect, the invention features a method for detecting the presence or amount of an analyte of interest in a sample, including the steps of providing a device as described above, and contacting the optically active surface with a sample potentially including the analyte of interest under conditions in which the analyte can interact with the optically active surface to cause the optically active surface to exhibit the second color when the analyte is present. An optical reader may be used to measure the change in the second color. An optical reader consists of one of the following group of instruments: an ellipsometer, a refletomer, a comparison ellipsometer, a profilometer, a thin film analyzer, or modifications thereof.

In preferred embodiments, the analyte of interest is sandwiched between a receptive material (e.g., an antibody or antigen) and a secondary binding reagent (e.g., an antibody or antigen); the analyte of interest is detected directly by the binding of the analyte; the analyte of interest is detected by competition with a signal generating reagent for the receptive material; the analyte of interest is detected by indirect signal generation; the sample is selected from the group consisting of urine, serum, plasma, spinal fluid, sputum, whole blood, saliva, uro-genital secretions, fecal extracts, pericardial, gastric, peritoneal, pleural washes, vaginal secretions, and a throat swab; and the method includes using a reflectometer to measure the change in color or intensity.

In particularly preferred embodiments, the method involves contacting the substrate with a test sample potentially containing the analyte under conditions in which the substrate exhibits the second color when the substrate includes the analyte in the above amount in less than one hour; and the device is a reflectometer set such that the first color is a background intensity of a specific wavelength or range of wavelengths of light, and the second color is a change in intensity of one or more of those wavelengths of light relative to the first color; or the device is a thin film analyzer set such that the first color is a background intensity of light transmitted through the analyzer to a detector, and the second color is a change in intensity of the light transmitted through the analyzer to the detector relative to the first color; or the device is set such that the first color is an eye-observable interference color, and the second color is a change in color relative to the first color.

In yet another aspect, the invention features a method for producing an optical assay device having a substrate and one or more optical layers, an attachment layer and a receptive layer, by spin coating one or more of the layers.

In preferred embodiments, the method involves spin coating an optical thin film on the surface of a substrate, where the film is formed from one or more of the group consisting of: polysilizanes, aluminum alkyloxides, silicates, titanates, zirconates, and T-resin siloxanes, and the film has a thickness between 250 and 550 Å; the method includes spin coating an attachment layer on the optical device on the optical surface of the device, most preferably formed from one or more of the group consisting of: non-linear branched polymeric siloxanes, film forming latexes, and dendrimers, with a thickness between 25 and 250 Å; and the receptive material is spin coated or solution coated to the attachment layer.

In another aspect, the invention features an optical assay device having an active receptive surface supported on a pedestal and held within a first container; the first container includes a first absorbent material located at the base of the pedestal, configured and arranged to absorb liquid draining from the surface, a second container, hingedly connected to one side of the first container, the second container having a second absorbent material, wherein the second container can be closed to the first container by rotation about the hinge, and wherein such closing causes the second absorbent material to contact the surface.

In preferred embodiments, the second container further has a handle configured and arranged to cause the second absorbent material to move relative to the location at which the second absorbent material contacts the surface; the device further has a movable flap in the second container which is configured and arranged to prevent the second absorbent material from moving from the second container; the device has a movable flap in the first container which is configured and arranged to prevent the second absorbent material from moving from the first container; each flap is hingedly connected to the first or second container, and is provided with one or more apertures to allow access to the surface or the second absorbent material.

In a related aspect, the invention features an optical assay device with a plurality of optically active surfaces supported on a base, the base having a first absorbent material configured and arranged to absorb liquid draining from the surfaces, and a slidable lid having one or more absorbent regions configured and arranged to contact the optically active surfaces during use of the device.

In preferred embodiments, the device is provided with step means to allow stepped movement of the lid relative to the base; the lid has a series of apertures which allow selected access to the surfaces during use of the device; the lid has an elongated aperture and wherein the base comprises a series of indicia, wherein the elongated aperture cooperates with the indicia to indicate a method for use of the device; the analyte of interest is the *Human Immunodeficiency Virus* (HIV) I or II or a combination thereof, Streptococcus Group A, Streptococcus Group B, RSV (Respiratory Syncytial virus), Hepatitis B, a Chlamydia species, HSV (Herpes Simplex virus), an antigen, an antibody, nucleic acid, oligonucleotides, chelators, enzymes, bacteria, viruses, hormones and receptors for the materials; and the device is configured and arranged to measure the presence of amount of Streptococcus A antigen, Streptococcus B, RSV, Chlamydia or a Hepatitis antigen; and has an optically active receptive surface.

In another aspect, the invention features an optical assay device, having an optically active receptive surface configured and arranged to allow simultaneous assay of a plurality of samples on the surface for one analyte of interest, and an automated liquid handling apparatus (e.g., a pipetting device) configured and arranged to dispense sample and reagent solutions to the surface.

In preferred embodiments, the device further has an optical reader to determine the result of each assay; the device has a blotting or blowing means configured and arranged for drying the surface; and the device provides a quantitative or qualitative assessment of a sample applied to the device.

In another aspect, the invention features a method for detecting an analyte of interest, by the steps of providing a detection device having a light reflective or transmissive substrate supporting one or more layers with an adhering attachment layer to which is affixed a receptive material which specifically interacts with the analyte of interest, reacting the device with a sample potentially containing the analyte under conditions in which the analyte binds to the receptive material, and reacting bound analyte with a reagent which creates a mass change on the surface of the device.

In preferred embodiments, the device has a substrate of planar reflective material supporting an attached layer of immunologically active material; the substrate consists of a planar reflective material; the substrate and the attached layer polarize radiation ellipsometrically upon reflection; the reagent increases or decreases the mass on the device, e.g., the reagent is an enzyme, or includes a polymeric latex, such as a film forming styrene-butadiene copolymer which is covalently attached to a secondary receptive material specific to the analyte of interest; most preferably, the reagent is an enzyme conjugate, which includes an anti-bacterial-antibody-enzyme complex; the reagent causes precipitation of mass by a precipitating agent, such as a substrate for an enzyme, e.g., containing 3,3',5,5'-tetramethylbenzidene.

In a related aspect, the invention features a kit for an optical assay for an analyte of interest having a test device with an optically active surface reactive with the analyte, and a reagent adapted to react with the analyte bound to the surface to alter the mass on the surface. Preferably, the reagent is an enzyme conjugate or a polymeric latex.

In another related aspect, the invention features a method for detecting an analyte of interest in a sample, by the steps of providing a thin film optical immunoassay device having a substrate, having an upper and a lower surface, and supporting on its upper surface, an unlabeled antibody layer bound to the substrate, at least one layer containing the analyte from the sample, the analyte containing layer supporting at least one layer having an enzyme conjugate complexed with the analyte; contacting the enzyme conjugate with a precipitating agent; incubating for a time period sufficient to cause precipitation of product from interaction of the precipitating agent and the enzyme; and optically measuring the mass change of the enzyme conjugate layer and the unlabeled antibody layer as an indication of the amount of the analyte in the test sample.

Preferably, the enzyme conjugate has an immobilized peroxidase or an anti-bacterial anti-body-horseradish peroxidase complex; or the enzyme conjugate is alkaline phosphatase and comprises an anti-bacterial-antibody-alkaline phosphatase complex; and the precipitating agent is a substrate containing 5-bromo-4-chloro-3-indolyl phosphate.

In another aspect, the invention features an instrument configured and arranged to detect the presence or amount of an analyte of interest on the substrate of an optical device. The instrument has a source of linearly polarized, monochromatic light positioned at an angle other than Brewster's angle relative to the substrate, and an analyzer positioned at the angle relative to the substrate at a location suitable for detecting reflected polarized light from the substrate. The analyzer is configured and arranged to approximately maximize change in the intensity of the light reflected from the substrate that is transmitted through the analyzer when a change in mass occurs at the substrate relative to an unreacted surface.

In another aspect, the invention features a method for optimizing an optical assay device for an analyte, by the steps of providing a substrate having a chosen thickness of an optically active layer thereon, providing an attachment layer of a chosen thickness on the optical coating, providing a receptive layer of a chosen thickness for the analyte, wherein at least one of the thicknesses of the optically active layer, attachment layer and receptive layer is varied to provide a plurality of thickness of the layer, contacting analyte with the receptive layer under conditions in which an increase in mass on the receptive layer results, and determining the optical thickness of the at least one thickness of a the layer. Preferably, the thickness of optical coating is varied incrementally along the length of the substrate.

Applicant has discovered that one feature useful for optimization of the claimed devices is the use of a substrate having a known refractive index having an anti-reflective layer attached to the upper substrate surface consisting of at least one layer of a material able to attach to the upper substrate surface and at least one layer of a receptive material positioned most remote from the upper surface and selected from materials specific to bind said analyte of interest in a fluid to be tested. It is important that the anti-reflective layer has a refractive index which is approximately the square root of the known refractive index of the substrate surface material adjacent to the anti-reflective layer, and has a thickness less than an odd number multiple of a quarterwave of the wavelength of a light incident upon the device.

That is, applicant has discovered that in order to optimize devices of the present invention it is necessary to deviate from previously developed mathematical algorithms (see Table 3, of the "Handbook of Optics", Walter G. Driscoll, and William Vaughan, editors, McGraw-Hill Book Co., NY, 1978, pp. 8-48 to 8-49) reflecting the desired thickness of specific optical layers in the device (see Background of the Invention). Thus, while such mathematical formulae may provide an indication of a general thickness that might be useful in a rather insensitive device, the method of this invention provides a device with significantly and surprisingly greater sensitivity.

Below is provided an indication of the methodology by which the optimal materials and methods useful for construction of optical test surfaces of this invention can be made. Generally, the present invention includes novel optically active test surfaces for the direct detection of an analyte, whether through colored signal generation detectable by eye or instrumented analysis. These test surfaces have a specific receptive material bound to the test surface by use of an attachment layer. Thus, the present invention provides a detection method which includes selecting an optical substrate, attaching receptive material specific to the analyte of interest on the upper layer of the substrate, contacting the receptive material with a sample fluid containing the analyte of interest, and then examining the change in reflection or transmission produced at the coated surface by observing a change in first color.

The present invention has a broad range of applications and, may be utilized in a variety of specific binding pair assay methods. For instance, the devices of this invention can be used in immunoassay methods for either antigen or antibody detection. The devices may be adapted for use in direct, indirect, or competitive detection schemes, for determination of enzymatic activity, and for detection of small organic molecules (e.g., drugs of abuse, therapeutic drugs, environmental agents), as well as detection of nucleic acids.

Devices of this invention feature a test surface suitable to performing assays which can be developed from a wide variety of substrates, anti-reflective, attachment, and receptive materials which can be introduced into a user friendly, broadly applicable assay device and protocol, may be used in a format which allows multiple test results from a single assay, and may be used to allow multiple analytes to be tested with a single sample in a simple way.

The use of an optical thin film or anti-reflective (AR) coating is one component in the device responsible for the observed color change. The devices of the present invention also provide improved performance attributes for assays which do not require this level of sensitivity. The improved performance attributes include length of assay, ease of interpretation, and flexibility in assay format and protocol.

Other features and advantages of the invention will be apparent from the following description of the preferred embodiments thereof, and from the claims.

DESCRIPTION OF THE PREFERRED EMBODIMENTS

The drawings will first briefly be described.

Drawings FIGS. 1A (unreacted test surface) and 1B (reacted test surface) are diagrammatic representations of the interference phenomena central to the devices and methods of the present invention;

FIGS. 2A and 2B are diagrammatic representations of specular (FIG. 2A) and non-specular or diffuse (FIG. 2B) substrate surfaces;

FIGS. 3A–G are a diagrammatic representations of a method of the present invention for selection of optimal interference films for use in devices of the present invention;

FIG. 4 is a representation of the attachment of 3-aminopropyltriethoxysilane to an optical surface;

FIG. 5 is a diagrammatic representation of the attachment of multivalent siloxanes which are useful to produce devices of the present invention; R may be any one of a number of groups which do not interfere with the attachment of the chemically active groups to the silica atoms present on an optical surface, and which do not interfere with the later attachment of receptor (e.g., biological) moieties, for example, such R groups may be primary, secondary or tertiary amines, alcohols, ethoxy groups, phenyl groups and aromatic groups, among others;

FIGS. 6A–6F are a diagrammatic cross-sectional representations of devices of the present invention, which are useful for either instrument read results (FIGS. 6A–C), or for eye-visible readable results; (FIGS. 6D-F). Materials and layers are designated as follows: substrate (1), optical thin film (2), attachment layer (3), receptive material (4), amorphous silicon (5), metal film (6), and composite interference film (7);

FIGS. 7A–E are diagrammatic representations of methods of the present invention in which an optical signal is obtained or enhanced by provision of mass on the optical surface; e.g., by use of an antibody having a latex bead (FIGS. 7A and 7B), or by use of an enzyme labeled antibody to cause catalytic deposition of product material onto a substrate (FIGS. 7C–D). Materials and layers are designated as follows: substrate (1), optical thin film—optional (2), attachment layer (3), receptive material (4), amorphous silicon (5), metal film (6), analyte (7), and mass enhancement (8);

FIGS. 8A–8G are isometric and exploded views of a device of the present invention; specifically, FIGS. 8A, 8B, 8C, and 8D are respectively a top view, a bottom view, an isometric side view, and a side view of the device, FIG. 8E is an isometric view of the device opened for use in an assay, FIG. 8F is an exploded view of the test surface of the device, and FIG. 8G is an exploded view showing various components within the device;

FIGS. 9A–9E are isometric and other views of a multi-test device of the present invention, specifically, FIGS. 9A, 9B and 9C are respectively a top view, an isometric view, and an exploded view of the device, FIG. 9D shows the back of the front cover of the device, and FIG. 9E is the top of the device without the front cover;

FIGS. 10A–I are a diagrammatic representation showing method steps for use of the device shown in FIGS. 8A–G;

FIGS. 11A–E are a diagrammatic representation showing a method of use of a device similar to that shown in FIGS. 9A–E;

FIGS. 12A–C are diagrammatic representations of a potential batch sampling formats;

Figure 15:
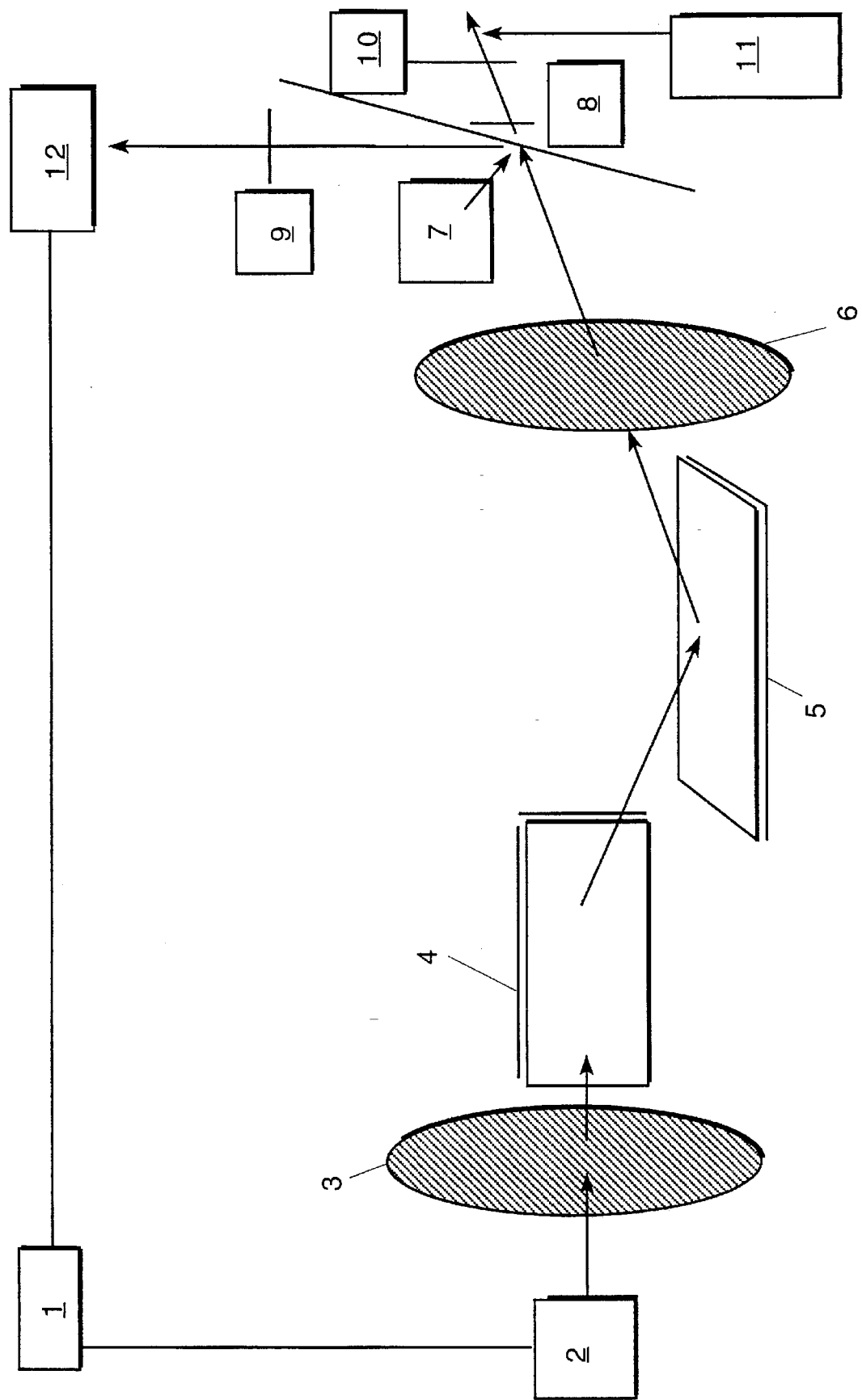
Figure 16:
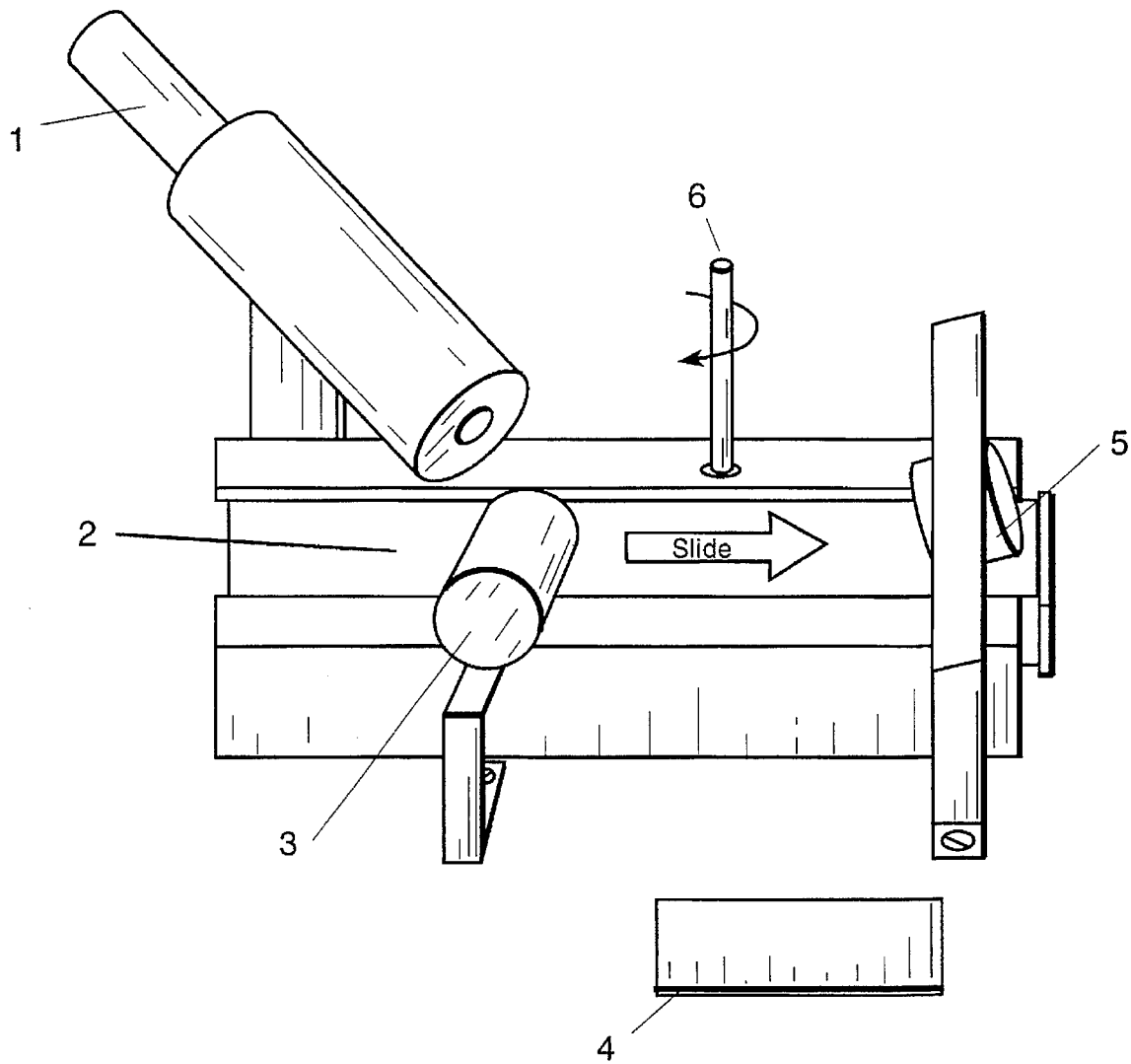
Figure 17A:
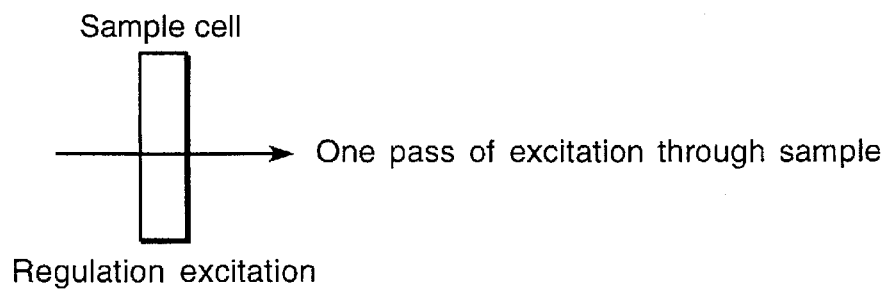
Figure 17B:
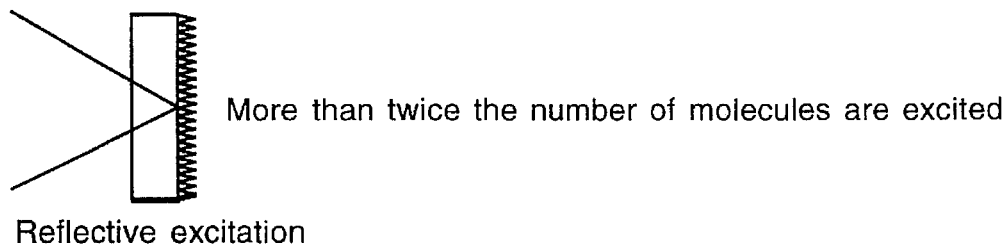
Figure 17C:
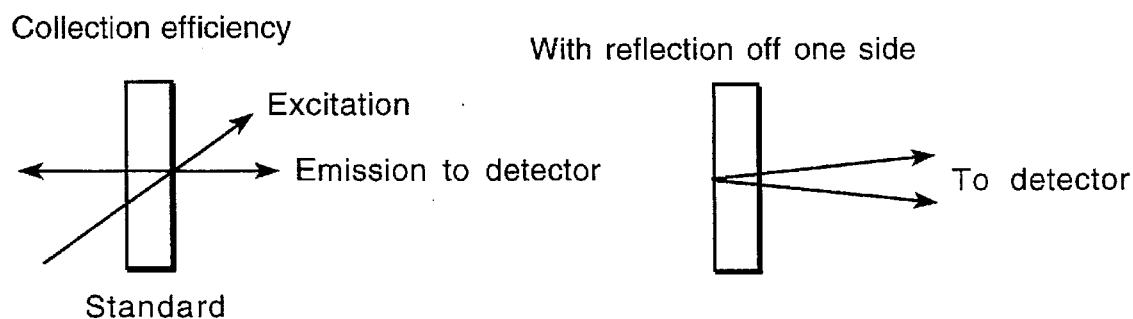
Figure 18:
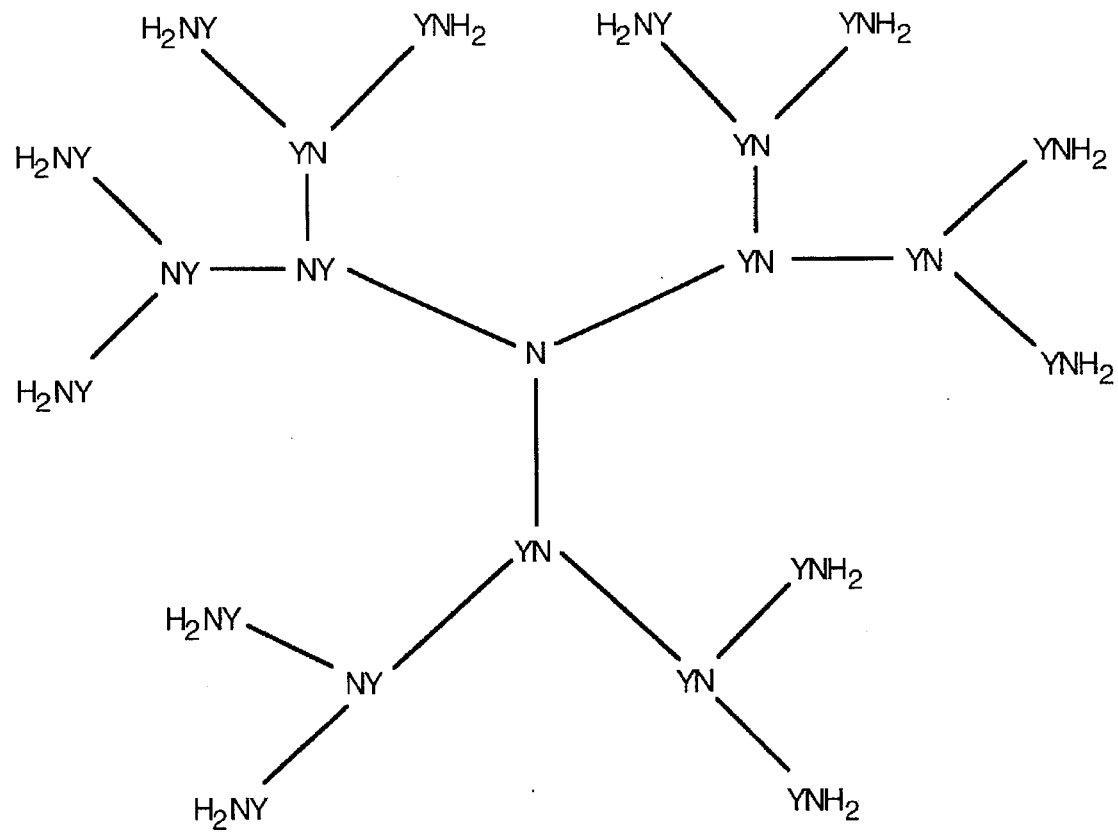

FIG. 15 is a diagrammatic representation of a modification of the prior art ellipsometer's optical path which demonstrates a new method for signal detection; and FIG. 16 is a diagrammatic representation of an ellipsometer having a reduced optical pathway length; and FIGS. 17A–C are diagrammatic representations of the advantages of a reflective substrate in fluorescent assay methods relative to conventional fluorescent methods;

FIG. 18 is a diagrammatic representation of a fifth generation star polymer or dendrimer (molecular self-assembling polymer).

Test Device

A number of types of optical thin film monitoring technology including ellipsometry, multiple angle reflectometry, interference spectroscopy, profilometry, surface plasmon resonance, evanescent wave, and various other forms or combinations of polarimetry, reflectometry, spectroscopy, and spectrophotometry are useful in this invention. This invention concerns the application of such technologies for the detection or measurement of changes in the thickness, density, or mass of thin films resulting from the concentration-dependent immobilization of analytes on a surface of suitably selected binding material. Such thin film assay technologies directly detect or quantitate the material of interest, and are alternatives to conventional solid phase assays. Thin film engineering problems have obstructed the development of test kits suitable to compete with existing diagnostic or other assay markets.

There are several critical features to the construction of a test surface of a device of this invention which combines specific binding layers and optical materials. More specifically, special considerations are required for combination of specific binding material with an anti-reflective or interference film. Each feature is discussed below, but in general, one must evaluate the interrelationships between an optical substrate, an optional optical thin film or interference film or anti-reflective (AR) film, an attachment layer, and the receptive material to be used in the composite test surface, as well as the final assay device requirements. The desired end use, visual/qualitative, instrumented/quantitative, and instrumented/qualitative will determine which feature of each component is selected in the production of a final useful test device of appropriate sensitivity and performance characteristics.

Figure 1B:
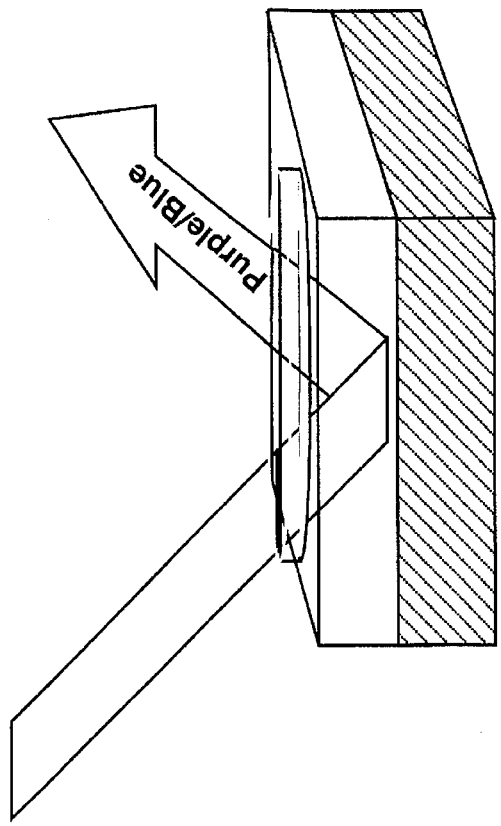
Figure 1A:
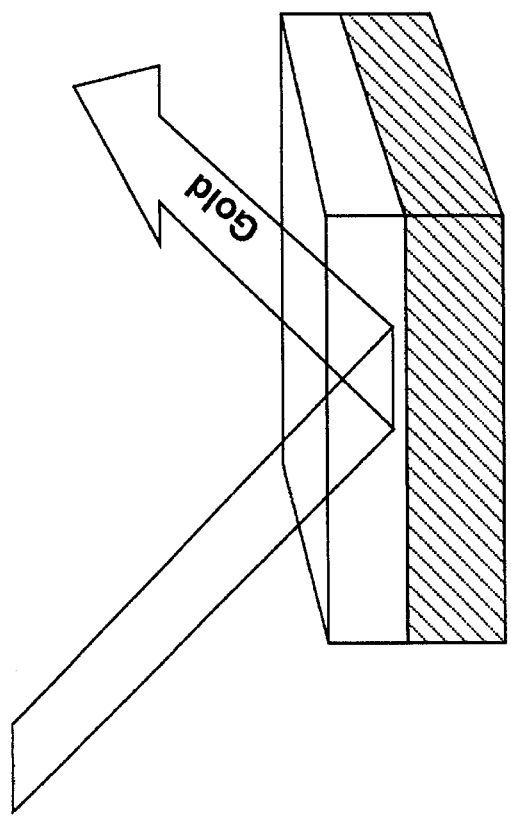

Referring to FIGS. 1A and 1B, there is shown the general phenomenon of light interference that is central to the utility of one embodiment of the present invention. This phenomenon is generally independent of the macroscopic surface characteristics of the test device. For example, it is important only that the device cause a change in the observed color of light reflected from the surface, and it is not necessary to provide any specific pattern on the surface, such as a diffraction grating or any related pattern. Thus, generally the surface is a planar surface with no specific pattern provided thereon. However, the surface may be provided in a shape or design that is visually useful to the human eye. An unreacted test surface causes white light incident at the device to be reflected as gold light, whereas a reacted test surface, due to the additional matter from analyte binding will cause the incident white light to be reflected as purple or blue light. The change from gold to purple or blue indicates the interference difference between the reacted and the unreacted test surfaces.

FIGS. 6A–F show in a diagrammatic form the general structure of various types of test surfaces of devices utilizing the present invention. For an instrument-read device the surface is provided with a substrate, an attachment layer and a receptive material layer, and may optionally also be provided with amorphous silicon and/or a metal film. In contrast, for visually readable devices it is necessary to provide an optical thin film (or an interference film) which, together with the attachment layer and receptive material layer, form a composite interference film. These various layers and their interactions are now discussed by way of exemplification.

Substrate

One or more thin films on a surface may attenuate incident light on that surface producing a change in the incident light that may be measured either by reflectance or transmittance. Reflection occurs when light encounters a medium of a different refractive index than the ambient medium. The ambient medium is generally air with a refractive index of 1.0. Transmission is a general term describing the process by which incident light leaves a surface or medium on a side other than the incident surface. The transmittance of a medium is the ratio of the transmitted light to that of the incident light. Both the reflected or transmitted light can be detected by eye, or may be measured with instrumentation. In this invention, use of such light attenuation in any specific device as a measure of the amount of an analyte in a sample is possible. The actual structure of the chosen device, however, depends on whether a reflection or transmission mode is desired, and whether the result is to be interpreted by eye or with an instrument. These specific combinations are relevant to the choice of a substrate(s) and are described generally below.

Reflectance Mode, Interpretation By Eye

One example of the phenomenon used in this invention is the interference colors observed when viewing oil on water on an asphalt surface. This interference effect is very common, and can be seen in a piece of multilayered mica, a fragment of ice, a stretched plastic bag, or a soap film. The change in color is due to local variations in the thickness of the material. The colors observed with oil on water are particularly intense and easily observed by the eye due to the difference in refractive index between water and oil. The colors are further intensified because the water provides a mirror-like (specular) reflection. The asphalt surface serves to absorb transmitted light, suppressing back reflection, which would tend to dilute the colors observed. The eye is more sensitive to contrast than to changes in intensity, therefore, selection of materials should allow for the production of colors which provide high contrast as a result of mass or thickness change at the surface. Films may be added to the surface of a material to modify the reflectance of one or more wavelengths or band of wavelengths. These types of materials are used to produce sunglasses, camera lenses, and solar windowpanes.

When the test surface is designed to produce a color change visible to the eye, the optical substrate must provide a surface that is reflective only at its uppermost surface, and of a known refractive index. Polished, monocrystalline silicon, metals, and some ceramics or dark glasses provide surfaces which may be used directly in this application. These materials inherently contribute to the generation of the observed signal and may be considered to be optically active.

Materials such as glass or plastics may require additional processing before they are useful in this technique. A material such as glass will allow reflection to occur at its upper and back surfaces. To prevent this, and allow such materials to be utilized, an additional film must be applied to the uppermost surface. Amorphous silicon, a thin metal film, or a combination of these materials may be used. In this case the glass serves as a solid support and is not inherently involved in the generation of the observed color, therefore it is considered to be optically passive.

Only the refractive index of the uppermost surface is important in the selection of the optical thin film or anti-reflective (AR) coating when either a single substrate material or a more complex structure is used (see below). AR materials compatible with a preselected substrate should approximate the calculations given in Table 3 pp. 8-48 to 8-49 of the "Handbook of Optics". With monocrystalline silicon this is simply the uppermost surface, with transparent glass this is the surface coated with amorphous silicon or other material. Adjustments to the AR film thickness are made using the wedge experiment described below. Using a reflective substrate to produce a color change perceived by the eye, the addition of a film of suitable refractive index and thickness is an absolute requirement in determining which wavelengths of light are antireflected.

The optical substrate materials may produce a specular reflection, or may be treated to, or intrinsically produce, a diffuse reflection which is less angle dependent in viewing the signal, as discussed below.

Transmission Mode, Interpretation By Eye

For this technique, the color produce is not viewed in the reflected light, but is observed as the light is transmitted through a surface. This selective transmission of different wavelengths of light is used to produce sunglasses, camera lenses, windowpanes, and narrowbandpass filters. The materials will selectively reflect and transmit different wavelengths of light. A narrowbandpass filter will reflect a large band of wavelengths of light, and will selectively transmit only a very small band of wavelengths centered around one specific wavelength. The narrowbandpass filter is constructed of an optical glass which is coated on one side with a material which will reflect many wavelengths of light. A change in the thickness of the material which coats the optical glass will change the useful range of the filter centering on a new set of wavelengths.

For this application, the optical substrate selected must be transmissive to the visible wavelengths of light, thus materials such as monocrystalline silicon, metals, certain plastics and ceramics are not suitable unless they are extremely thin, transparent sections. Glasses and certain transparent plastics are the most useful for this application. In this type of technique the substrate is optically active. For the generation of a color change visible to the eye, the refractive index of the substrate impacts the type of AR film which is selected. A uniform or smooth surface is required for use in this application to prevent loss of signal due to scattering at one or more of the transmitting surfaces.

A glass substrate coated with a layer of amorphous silicon may be transmissive to visible light at certain angles, if the amorphous silicon layer is sufficiently thin. This is also true for a very thin layer of metal on a glass substrate. For this type of test surface, the viewing should be arranged such that the amorphous silicon is the back surface of the test piece (i.e., opposite to the viewing surface).

Reflectance Mode, Instrumented Interpretation

The use of the AR or optical thin film component is optional when an instrumented detection is utilized. A reflectometer requires a color change or change in luminosity (intensity) for generation of a signal. This color change may be different from the color change selected for visualization by eye, as the instrument will record changes in intensity and does not require a maximal change in contrast. AR film thickness is preferably adjusted to provide the maximal change in recorded intensity as a function of analyte binding. In addition, modifications to the reflectometer will allow it to also measure changes in color/luminosity (intensity) with a specularly reflecting or diffusing reflecting surface.

For use with the ellipsometric type of instruments the optical substrate should provide a specular reflection. Reflection should occur only from the uppermost surface. As previously discussed, glass serves only as a support in this case and is optically passive or not involved in the generation of the detected signal. Instrumented detection will observe a change in light intensity due to its interaction with the thin films. The light may be elliptically or linearly polarized, polychromatic, monochromatic, and of any wavelength desired.

Transmission Mode, Instrumented Interpretation

Any optical substrate which is transparent to the incident light may be used in this application, whether that light is polychromatic, monochromatic, linearly polarized, or elliptically polarized, and of any wavelength desired. Use of an AR film is optional in this application, but if required for use with a reflectometer, the rules presented for the interpretation by eye also apply here. Thus, the refractive index of the optical substrate influences the selection of the AR coating. Design of the reflectometer is easily modified to allow reflection or transmission measurements to be made.

When a change in the transmitted light is to be made independent of any color, an AR film is not required. The only requirement for the substrate in this application is that some component or components of the incident light be transmitted, and that a change in mass or character on the uppermost surface of the test piece modifies the transmitted light in a detectable manner. Materials such as the Irtran series produced by Eastman Kodak may be of use in this application for monitoring changes in the infrared (IR) properties of these films.

Thus, the term "substrate" includes not only a solid surface for holding the layers described below, but also an optically active substrate which may include an optical thin film. For clarity, these two portions of a substrate are discussed separately, but those in the art will recognize that all that is essential in this invention is that the layers (to which the attachment layer and other layers are attached), be optically active to provide a detectable change in the thickness or mass of these layers as described above.

The optical substrate is either a solid material, or supports a layer of material which acts optically. These materials must have a known refractive index if it is to be combined with an optical thin film to produce an interference effect. Thus, it may be formed from any desired material which is reflective or made reflective, as discussed below. For instrument use, the substrate can also be transparent (e.g., glass or plastic) so that transmitted light is analyzed.

This invention is suited to use of a variety of optical substrate materials and formats to suit the needs of the end user. The optical substrate can be formed of, or have coated on it, a material that provides either diffuse or specular reflection, it may be rigid or flexible, reflective or transmissive, and it may form an optically functional component of the test surface, or it may act as an optically passive support (and be provided with optically active layers). Devices designed for instrumented analysis may not require an anti-reflective (optical thin film) coating on the substrate, while those designed for viewing by eye may require such a coating. Criteria useful for selecting an optical substrate for instrumented applications, or for viewing by eye of a color-signal generating application, are presented below.

A wide range of rigid materials may form the optical substrate, including glass, fused silica, plastic, ceramic, metal, and semiconductor materials. The substrate may be of any thickness desired. Flexible optical substrates include thin sheets of plastic and like materials. Most substrates require only a standard solvent, plasma etching, or acid cleaning, well known to those skilled in the art, before subsequent layers may be deposited on them.

For color-signal generation visible to the eye, an anti-reflective coating material is required. Polymer films, such as mylar (polyethylene terapthalate) and other materials having a low surface energy may not adhere well to such material and may require additional treatment before this layer can be deposited. To improve adhesion these optical substrates may be etched in an oxygen plasma, under conditions standard for oxygen plasma cleaning in semiconductor processing.

The surfaces of many solid materials, such as glass, and semiconductor materials, such as silicon, metals, etc., are sufficiently smooth to provide specular reflection if they are polished. For use in a reflection-based assay the major requirement in selecting an optical substrate is that the reflection occur, or be made to occur, only at the upper surface. This is especially critical for devices which include an interference film and are to be viewed by eye. This is easily accomplished by vapor deposition of a thin metal film on the substrate, and attachment of subsequent layers by techniques known to those skilled in the art. For example, the uppermost surface of a glass substrate may be coated with a layer to prevent unwanted reflections from the lower surface.

Metal Layer

If the substrate is to be used in a reflection mode, and is partially or fully transparent, it may be coated with an opaque material to block transmitted light and allow reflection to occur only from the upper surface. For example, a glass substrate may be coated with a layer of aluminum, chromium, or other transparent conducting oxide, by mounting in a vacuum chamber facing an aluminum-filled tungsten boat. The chamber is evacuated to a pressure of $1\times10^{-5}$ Torr. Current is passed through the tungsten boat, raising it to a temperature at which the aluminum deposits on the substrate at a rate of 20 Å/second for 100 seconds, coating the glass with an opaque layer of aluminum having a thickness of 2000 Å. Thinner layers of aluminum or chromium may also be used to eliminate any back surface reflections. Non-conducting deposition techniques may be used to deposit the metal film.

Amorphous Silicon

The aluminum-coated glass, described above, may be considered optically passive. Thus, if it is coated with a layer of hydrogenated amorphous silicon (a-Si:H), the optical characteristics of the substrate will be derived from the a-Si:H alone. The aluminum-coated glass is required only when the amorphous silicon deposition process requires a conducting surface. Techniques which do not require the use of a conducting surface for the deposition of amorphous silicon are known. To produce this substrate, the aluminum-coated glass is mounted on one of two opposing electrodes in plasma-enhanced chemical vapor deposition system. The system is evacuated, and the substrates are heated to 250° C. A constant flow of silane ($SiH_4$) gas into the chamber raises the pressure to 0.5 Torr. A plasma is struck by applying 10 mW/cm$^2$ of RF power to the electrodes. A film of a-Si:H deposits on the substrates, and grows to a thickness of approximately 1000 nm in about 75 minutes. The a-Si:H so formed may form the first optically functional layer on the test surface.

A glass substrate coated only with a-Si:H (without the aluminum layer) is also useful in this invention. Transparent substrates, such as glass, fused silica, sapphire, and many plastics may be used in instrument transmission measurements, without additional modification. Color-signal generation visible to the eye is possible with a transmissive substrate where the anti-reflection properties of the coatings are determined from the transmitted light.

Many of the substrates with a sufficiently reflective surface for thin film measurements are formed of metals. Examples of these metals, include but are not limited to, iron, stainless steel, nickel, cobalt, zinc, gold, copper, aluminum, silver, titanium, etc. and alloys thereof. Metals are particularly useful substrates when an instrument detection method is employed. For instrumented measurement systems, the main requirement is that the substrate be reflective and planar. In contrast, for eye visible color signal generation it is very difficult, but not impossible, to match the reflectivity of the metal with a suitable anti-reflective coating. The reflectivity of the optical substrate and the optical thin film (see below) used must match for the optimal production of an interference color. Thus, devices designed for color production are generally formed from other substrates, or from amorphous silicon-coated metal substrates as discussed above.

Non-Specular Surface

Figure 2A:
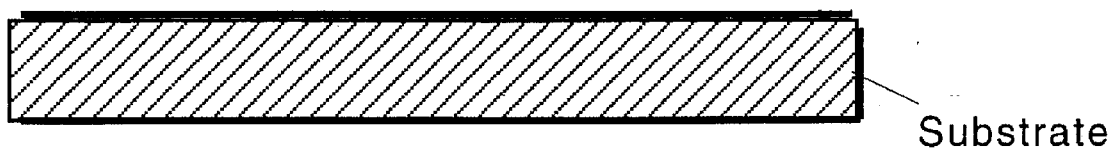
Figure 2B:
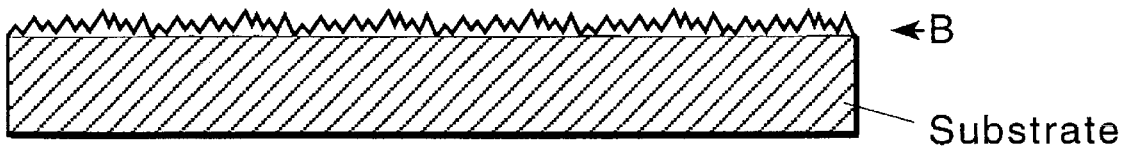

Referring to FIGS. 2A and 2B, there is a diagrammatic representation of a general concept of the present invention in which rather than providing a specular substrate (2A) (in which the surface is mirror-like or almost mirror-like), the surface is manufactured in a manner which will create irregular bumps as shown diagrammatically in FIG. 2B and referenced by the symbol B. These bumps are significantly exaggerated in the figure and are generally of a size between 1 nm and 100 μm, most preferably between about 100 nm and 100 μm. Again, these bumps are not provided in any regular manner, (such as in the form of a diffraction grating), but rather are provided simply to cause a general scattering of light incident upon the surface. By such provision it becomes unimportant from which direction the light incident on the substrate is angled and the color change noted in FIG. 1B can be observed by holding the substrate at any angle to incident light, or to the observing eye. Both instrument and eye-visible color signal generation surfaces can be constructed with specular or diffuse reflecting substrates.

A surface that provides a diffuse reflection can be obtained in several ways: physical abrasion, chemical abrasion, or coating of a, material. Specular substrates may be roughened by physical abrasion using a compound containing grains of silicon carbide to form a diffuse surface. Alternatively, the material may be chemically abraded. For example, a monocrystalline silicon wafer may be etched in an aqueous solution of 30% potassium hydroxide (by weight) at 80° C. to form a rough surface composed of pyramid structures. The abrasion process may be followed by an isotropic etch, well known to those skilled in the art, to yield an irregular surface that produces a diffuse reflection.

The diffusing properties of the substrate may also be produced by a coating. For example, polystyrene spheres having a diameter of 2 microns may be suspended in a fluid, such as a polyamide-containing solution. A glass slide is vacuum mounted onto a spin coater, and the central portion of the slide covered with the solution. The spin coater is switched on for several seconds at 3000 rpm, causing the spheres in the solution to disperse uniformly over the surface. The fluid is allowed to dry, yielding a surface that produces a diffuse reflection.

Embodiments of the present invention include use of an optical substrate with an irregular surface to produce diffuse light reflection. They also include use of a smooth optical substrate surface covered with, overlaid by, or observed through, a light diffusing or light modifying material such as or textured plastic. Viewing through such a plastic produces a similar effect to that discussed above.

In one example, the optical substrate is formed from a silicon crystal which is grown and extruded to 4 inches in diameter and then diamond sawed to form a wafer. The wafers are treated with chemical etchants to smooth the surface and reduce flaws. The wafers are lapped or ground with aluminum oxide, titanium oxide, or silicon carbide particles in a talc slurry. The initial grain size is large and successively smaller particle sizes are used to produce an increasingly smoother surface. Both sides of the wafer are subjected to this process. The final lapping process leaves a very diffusely reflective surface. Wafers may be further processed with chemical or plasma etching to modify the diffuse reflecting characteristic of the substrate.

Once the wafers are lapped, they are cleaned using the following process or a known modification thereof: the wafers are sonically cleaned with a cationic detergent, followed by a rinse with 18 megaohm water. Then they are cleaned with an anionic detergent, followed by a rinse in 18 megaohm water. They are ultrasonically cleaned with an aqueous ammonia solution made of 370 ml of 30% $H_2O_2$, 250 ml of aqueous ammonia and 9 gallons of water, and are rinsed in a cascade of water with the final rinse being with 0.1 micron filtered water. They are then spin-dried and are ready for optical coating. An alternative to this procedure is the "RCA Clean" described in *Polymer Surfaces and Interfaces*, edited by W. J. Feast and H. S. Munro, John Wiley and Sons, N.Y. N.Y., page 212, 1987.

For glass, the degree of surface character or the irregularity is discussed in terms of gloss. The diffuse reflective capability of the surface described here refers to the degree to which the reflection is scattered compared to a pure specular reflection. Diffuseness is a function of the surface topography and because the relevant topography is much larger than the interference film or biofilms, the fuzziness is not expected to vary significantly for different specific binding material. For eye-visible color-signal generation the film will affect the lightness or color of the reflected light, but not its diffuse character. Diffuse surfaces which produce color signal are particularly useful with reflectometers.

The surface topography, and hence fuzziness or irregularity may be characterized with a surface profilometer, such as the Dek-tak® (Sloan Technology Corp., Santa Barbara, Calif.). The Dek-tak® provides readings on the separation or distance between surface features and an average value for the height of surface features over a defined region of a surface. One useful measure of the surface is the Root Mean Square (RMS) or average surface roughness divided by the average peak spacing, where a peak is defined to be a protrusion with a height of at least 50% of the RMS roughness. Since roughness is a function of the reflectivity versus angle, it may be quantified by measuring the angle dependence of the reflectivity. For a light source incident at 30° from normal, the reflected light intensity on a photo-diode should be measured as a function of the angle from 0° to 90°. The wafer selected should optimally show a smoothly varying reflectivity over the angular range viewed. Using a HeNe laser light source, the specular reflectance from a roughened surface useful in this invention should be less than 5%, assuming a polished wafer reflects at 100%.

In an embodiment of the present invention, articles having the non-specular, i.e., irregular, surfaces are characterized by peak values between about 2700 and 3295 with a preferred measurement of approximately 2995. This value represents the RMS roughness divided by the average peak of the textures.

In addition to abrasive lapping, a wide range of chemical or plasma etching techniques are suitable for providing the diffuse properties of the substrate. For example, glass can be modified to a diffuse light reflecting surface using a HF etch as in the production of frosted glass.

For the color-signal generation, substrate selection will determine the characteristics of the anti-reflective material or materials used in subsequent coating steps. Below is described the selection of anti-reflective materials based on initial substrate selection.

The substrate material may be cut, sawed, scribed, laser scribed, or otherwise manipulated into the desired test piece configuration. Suitable test pieces for a single use assay are 0.5 $cm^2$ to 1 $cm^2$ with 0.75 $cm^2$ being preferred. Test piece sizes are not restricted to the above, as alternative formats may require substantially more or less reactive test surface.

Optional Optical Thin Film Material(s)

Referring to FIGS. 1A and 1B, the simplest description of a single optical thin film is that the substrate is coated with a thin layer of material such that reflections from the outer surface of the film and the outer surface of the substrate cancel each other by destructive interference. Two requirements exist for exact cancellation of reflected light waves. First the reflections must be 180° out of phase and second they must be of equal amplitude or intensity.

In the reflection mode, the optical thin film properties of the coatings of a device of this invention suppress the reflection of some wavelengths of light and enhance the reflection of others. This causes the suppressed wavelengths of incident light to enter the substrate, or an opaque coating on the substrate where they are absorbed. Most of the light of other wavelengths, whose reflection is not suppressed, does not enter the coated substrate and is reflected, however, some components may be absorbed. As the optical thickness of the coating changes, the range of wavelengths in the reflected light changes. In transmission mode, the properties of the coatings suppress the reflection of some wavelengths of light and enhance the reflection of others, as in the reflection mode. This causes the suppressed wavelengths of the incident light to enter the substrate and to be transmitted. Light of other wavelengths, whose reflection is not suppressed to as great an extent is reflected, and transmitted to a lesser extent. As the optical thickness of the coating changes, the range of wavelengths in the transmitted light changes.

Where eye-visible color-signal generation is required (see FIGS. 6D–F, right hand side), the final assay result may also be measured by instrumentation. Ideally, for the production of a perfect interference film using only the specific binding materials discussed below, and an optical substrate, the substrate should have a refractive index of the square of the refractive index of the receptor layer (see below), i.e., $(1.5)^2$ or 2.25, variations in this number can still provide useful devices of this invention as will be discussed below). The material selected should be mechanically stable to subsequent processes, reflective, and of known refractive index. It is not always possible to match the optical substrate to a particular film. For example, a biological film. In these cases, an intermediate optical thin film must be used to compensate for the lack of a suitable optical substrate. For eye-visible color-signal generation, the substrate material is subject to two restrictions: first, it must adhere to the optical thin film material, and second, in the simplest case, the refractive index of the substrate should approximately equal the square of the refractive index of the material directly above it or, on a more complex test surface, the refractive index of the substrate should be selected to fit generally one of the formulae in Table 3, pp 8-48 to 8-49, of the "Handbook of Optics". For example, use of a silicon wafer with a refractive index of approximately 4.1 allows a test surface to be designed with a wide variety of corresponding optical thin films or anti-reflective materials. The material should be coated to a thickness of a quarterwave for the wavelengths to be attenuated, or variations in the formulae given in Table 3. Those skilled in the art will realize that various other substrate materials are equally suited for use as a test surface if they satisfy the above criteria.

The optical thin film coating is deposited onto the surface of the substrate by known coating techniques. For example, by sputtering or by vapor phase deposition in a vacuum chamber. Various other useful coating techniques are known to those skilled in the art. Materials useful as optical thin film coatings are formed of clear material which is significantly transmissive at the thickness utilized, and suppresses some wavelength of reflective light when coated onto the substrate. The film, once deposited onto the optical substrate, is also stable to subsequent processes.

Preferably this test surface will have fewer optical layers, but more complex test surfaces possessing more layers corresponding to the formulae provided in Table 3 with modifications discussed below. As already noted, the theoretical calculations are the starting point for material selection. Theoretical considerations may be used to determine which materials are compatible with a pre-selected substrate. The coating thickness may be set at the predetermined quarterwave thickness or to a preselected interference color. However, for the construction of a specific binding material optical film composite of this invention a number of adjustments are required to the initial coating. These adjustments are described below.

For example, a substrate such as a polished silicon wafer has a refractive index of approximately 4.1. To maximize the utility of the test surface in accordance with the first equations in Table A, the optical thin film material selected should have an index of refraction of 2.02 (i.e., the square root of 4.1). Maximal "apparent" color change is achieved for silicon with materials having refractive indices near 2.0, such as silicon nitride ($Si_3N_4$) or silicon/silicon dioxide composites. Other optical thin film materials that have a similar refractive index include, but are not limited to: tin oxide, zinc oxide, chromium oxide, barium titanate, cadmium sulfide, manganese oxide, lead sulfide, zinc sulfide, zirconium oxide, nickel oxide, aluminum oxide, boron nitride, magnesium fluoride, iron oxide, silicon oxynitride ($Si_xO_yN_z$), boron oxide, lithium fluoride, and titanium oxide.

Silicon Nitride

One method for the deposition of silicon nitride is a plasma-enhanced chemical vapor deposition technique similar to that described above for the deposition of a-Si:H. It is recognized that this technique, or modifications of this technique, are suitable for the deposition of a large number of materials. For example, to produce $Si_3N_4$, ammonia ($NH_3$) gas is added to silane gas. Silicon nitride performs well as an optical thin film on substrates of monocrystalline silicon and polycrystalline silicon, or on amorphous silicon and polycrystalline silicon on optically passive substrates.

The compatibility of the silicon nitride deposition process with the a-Si:H deposition process produces a very cost-effective combination. The two films may be deposited as follows. Glass substrates are mounted in an evaporation systems where a 2000 Å thick layer of aluminum is deposited on the glass, as described above. Then the substrates are mounted in a plasma-enhanced chemical vapor deposition system, where a 1 micron thick layer of a-Si:H is deposited, as described above, followed by a silicon nitride layer. In this way an inexpensive reflection-mode test surface is formed on a glass substrate. This approach may be extended to the deposition of these coatings on dielectrics and flexible substrates described in U.S. Pat. No. 3,068,510 issued Dec. 18, 1962 to Coleman.

The refractive index of the silicon nitride, or by analogy the silicon/silicon dioxide composites, may be controlled in the vapor deposition process. The ratio of gases may be varied, or the deposition rates may be varied, and a variety of other methods known to those skilled in the art may be used to control or select the refractive index of the optical thin film deposited.

Multi-layer Films

Multi-layer optical thin film coatings may be deposited by electron beam evaporation. A substrate is mounted in a vacuum deposition chamber, and suspended over two or more crucibles of the various material to be evaporated. Each crucible is then heated by an electron-beam gun, and the rate of evaporation monitored using a crystal thickness monitor. Each crucible is covered by a movable shutter. By alternately opening and closing the shutters, the substrate is exposed sequentially to each vapor stream, until the desired multi-layer stack has been deposited, or a multi-component film is deposited. The described procedure may be generalized to more than two crucibles in order to deposit multiple layers of various optical thin film materials, or multi-component films tailored to a specific refractive index.

The test surface when coated at a specific thickness with a silicon nitride film suppresses certain wavelengths in the blue range of visible light and therefore reflects a yellow-gold interference color. Although a yellow-gold interference color is utilized in the examples below, the interference color of the test surface can be any suitable color in the spectrum of light. The color depends on the substrate material selected, the chemical composition and refractive index of the optical layer/s selected, and the thickness and number of coated layers. These design techniques can also be utilized to produce test surfaces with signals or backgrounds in the ultraviolet or infrared region of the spectrum of light, however, these test surfaces are useful only in instrumented detection of a bound analyte.

For example, lithium fluoride may form one component of a multi-layer stack. It has a refractive index of 1.39 for visible light, and thus forms a one-quarter wavelength layer for green light at a thickness of 925 Å. It may be evaporated from a platinum crucible at approximately 900° C.

Titanium Film

Titanium films are particularly useful for the production of optical films. Such films have advantages since they use materials which are safer to handle and dispose of than other optical materials, such as $SiH_4$. The method of application is also more cost effective and rapid with less instrumentation required.

Titanium dioxide has a refractive index of approximately 2.2 for visible light, and thus forms a one-quarter wavelength layer for green light at a thickness of 585 Å. Because titanium dioxide decomposes into lower oxides upon heating, the evaporated films are not stoichiometric. To deposit stoichiometric titanium dioxide the electron-beam must be pulsed. The deposition occurs at approximately 2000° C.

Organotitanates may be hydrolyzed to titanium dioxide ($TiO_2$) under conditions which prevent premature polymerization or condensation of titanates. The latter reactions are base catalyzed. The organotitanate may be mixed with an aqueous solvent system and a surfactant. The solvent/surfactant system selected should tolerate a high solid content, have good leveling or spreading capacity, and be miscible with water. Alcohols and the fluorosurfactants manufactured by 3M (Minnesota) are particularly useful for this method. Hydrolysis of the organotitanate should occur prior to any polymerization or condensation, and the solvent system should be acidic to prevent undesired polymerization reactions. The counter ion supplied by the acid can be used to improve the solubility of the titanium—acetic acid and hydrochloric acid are preferred. A nonaqueous solvent system may be used but the organotitanate must not be prehydrolyzed. The solvent must be anhydrous to improve the stability of the coating solution. Suitable solvents include toluene, heptane, and hexane. A surfactant is not required (as in the aqueous solvent system), but may further improve the coating characteristics.

Once the organotitanate and the solvent system are mixed, a predetermined volume of this solution is applied to an optical substrate using a spin coating technique. When the organotitanate is mixed with a non-aqueous solvent system the solution is applied to the optical substrate by dynamic delivery. In a dynamic delivery method the substrate is attached to the spin coater and spun at 4,000 to 5,000 rpm. The solution is applied to the spinning substrate which continues to spin until an even film is obtained. For aqueous solvent systems, dynamic or static delivery of the solution is possible. In static delivery, the solution is applied to the substrate and then the spinning is initiated. The spin rate required is dependent on the percent solids in the solution, the volume applied to the substrate, and the substrate size. The thickness of the titanium layer generated is a function of the percent solid, the volume applied, and the spin rate.

The titanium dioxide layer may be cured to the substrate by a number of techniques. The refractive index of the titanium dioxide layer is controlled by the temperature of the substrate during curing and to a much lesser degree the length of the curing process. The curing process may use a furnace, an infrared heat lamp, a hot plate, or a microwave oven.

Titanium dioxide offers a number of advantages for this application:

1. It is inexpensive and easy to apply to a wide range of optical substrates and is not hazardous to produce.
2. Its refractive index can be controlled and will cover a range from 1.6 to 2.2. Thus, it can be used to give an equivalent material to silicon nitride with a refractive index of 2.0.
3. The titanol formed at the surface reacts chemically similar to silanols in subsequent derivatization processes (see below).

In addition to the titanates, silicates, aluminum alkyloxides, and the corresponding analogs of zirconium may all be used to produce an optical thin film by this method.

In addition to spin coating the titanium dioxide, polysilazanes may be used to produce silicon nitride coatings by spin coating. These protocols may also be adapted for use in this technology. T-resins such as polymethylsilsesquioxane or polyphenylsilsesquioxane (general formula $RSiO_{1.5}$) may be spin coated to the optical substrate or support to provide a silicon carbide surface with a suitable refractive index for generation of an optical thin film.

Optimization Procedure

A model was developed to select an optimal background interference color for any particular combination of substrate, optical thin film (AR film), attachment layer and receptive material. Since the mathematical models developed to date are not effective to provide useful devices of the present invention, these models are used only as a starting point in the device construction. Optimization is necessary to provide a device of this invention. For illustration purposes only, the selected substrate was a silicon wafer and the optical material selected was silicon nitride. The most highly contrasting colors observed were a yellow-gold changing to magenta with an increase in mass on the test surface.

Figure 3A:
Figure 3B:
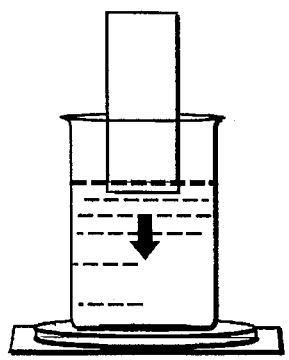
Figure 3C:
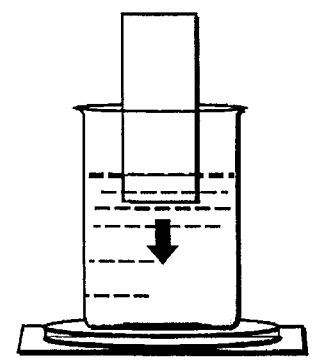
Figure 3D:
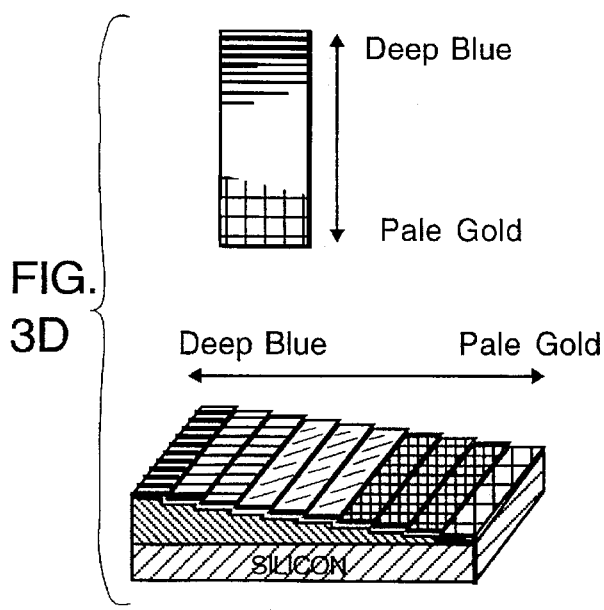
Figure 3E:
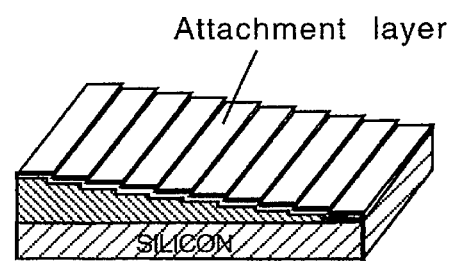
Figure 3F:
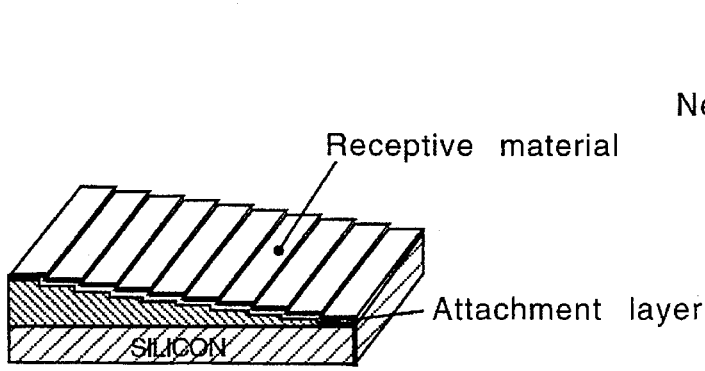
Figure 3G:
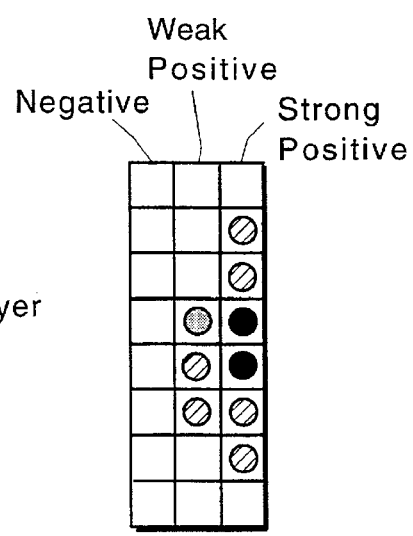

Referring to FIGS. 3A–3G, a method for selection of the optimal thicknesses of each layer for a device of the present invention is disclosed for a silicon nitride film on silicon. In a first step (see FIG. 3a), a silicon substrate is provided either with a specular or non-specular surface. A silicon nitride film is provided on this surface and, as shown in FIGS. 3B and 3C, is eroded away in a stepwise fashion by heating and stirring in an appropriate solution. The timing of each step is selected such that the portion which is subjected to erosion for the longest period of time exhibits a pale gold color, while that portion which is not exposed to erosion exhibits a deep blue color (see FIG. 3D). An attachment layer and a receptive material layer for analytes to be detected are provided on the silicon nitride (see FIGS. 6E and 6F). These layers are provided in a thickness which may be determined empirically, or can be similarly optimized (e.g., in this stepwise fashion) if so desired. In a seventh step, an assay is performed with three portions of the strip being treated in a different manner such that a negative response, a weak response, and a strong response can be recorded. The results are shown in FIG. 3G, and the thickness of silicon nitride useful in the invention can be determined by those sections providing the strongest weak positive response in the test.

Specifically, a silicon wafer was prepared with a thick coating (800 Å) of silicon nitride so that the wafer appeared to be a deep blue. Then the optical thin film material was etched off the wafer in a hot, phosphoric acid bath to produce a wedge of interference colors. The optical material was etched such that 300 Å remained at one end of the wedge and 700 Å remained at the other end of the wedge. (At 180° C. the silicon nitride was removed at approximately 20 Å per minute.)

The etched, wedged test surface was coated with an attachment material, and then a receptive material. The reactive surface was analyzed with a negative, a weak positive, and a strong positive sample. The thickness of the optical material was then measured at the wedge segments which appeared to provide the most distinctive color change, or visual contrast. The optimal film thickness is most readily selected based on the composite test surface analysis. This process maximizes the visual contrast obtained for the specific assays.

Silicon nitride is easily etched to produce the wedge of thicknesses needed for this empirical evaluation. Many materials are susceptible to an acid etching or base etching process. Other chemical methods of etching the material are possible. If a desired optical film is not easily removed from a particular optical substrate because the film is too easily destroyed, or the optical substrate is not stable to the required etchant, another method of generating the wedge may be used. For instance, monocrystalline silicon is not stable to prolonged exposure to basic solutions. If an optical film on silicon requires a basic etchant the wedge can not be generated using a chemical approach.

Several alternatives exist: (1) the optical film may be deposited on an optical substrate which is introduced stepwise into the coating chamber over a period of time. Each newly exposed section will receive a thinner coating than the previously exposed section. (2) The substrate may be masked and the mask removed stepwise over a period of time. (3) Several different coating runs each producing a different thickness of optical material may be performed. (4) Ion milling may also be used to etch certain materials.

For any given optical substrate and a substitute optical thin film of the same refractive index as the original optical thin film, this optimization need not be repeated. The above method was used to establish that a 480–520 Å film of Si$_3$N$_4$, with a refractive index of 2.0, was required for a silicon wafer (optical substrate) to be used in a binding assay (see Example 2). It has been demonstrated that TiO$_2$ at a refractive index of 2.0, using the same attachment layer and receptive material, requires a 480–520 Å coating. Minor thickness adjustments may be required if the refractive index is not exactly that of the original material.

Thus, the formulae established for the coating of optical thin films are used as a guideline only for the production of a test surface suited to a specific binding assay. For a pre-selected substrate, the square root dependence of an optical thin film is used to screen appropriate optical materials. Some deviation from the perfect square root dependence is acceptable for this invention. The use of a quarter-wave thickness of the optical coating is only an initial guide to coating thickness. Thickness of the optical thin film must thus be empirically derived in consideration of the specific binding materials. The composite specific binding optical thin film of this invention does not meet the conditions theoretically required to produce such a film. Neither the thickness nor the refractive index rules are followed. Surprisingly such deviation from these accepted formulae results in a test surface which is very sensitive to mass changes or thickness changes.

While of less importance, the relative thicknesses of each layer, and not just the optical thin film layer, may be varied as described above to optimize the final test device for any particular attachment layer and receptive material layer.

Attachment Layer

This invention is further concerned with materials and methods for producing a layer which attaches the specific binding layer to the optical substrate or optical thin film. Specifically, the invention pertains to a method for producing an attachment layer which optimizes the functional density, stability, and viability of receptive material immobilized on that layer. The attachment materials selected must be compatible with the biological or receptive materials, must physically adhere or covalently attach to the upper test surface (whether an optical thin film is included or not), must preferably not interfere with the desired thin film properties of the test surface, and must be sufficiently durable to withstand subsequent processing steps.

The density and stability of immobilized receptive material (or, in some cases, enzymes) must be controlled to optimize the performance of an assay test surface.

Applicant has determined that one problem in obtaining useful devices of this invention was the extremely limited macroscopic and/or microscopic surface area of the test films employed in a thin film assay as compared with the microscopically convoluted surface characteristics of other conventional solid phase assay materials. In most cases, the optical substrate must be evenly coated with a continuous attachment layer that protects the receptive material from any toxic effects of the reflective substrate while adhering it to the surface.

In conventional solid phase assays, the larger test surfaces generally employed, such as microtiter wells, have much greater total surface area and microscopically convoluted surfaces relative to a thin film substrate. Thus, the amount of receptive material immobilized compensates for any sparsity in coverage, or any losses in viability (ability to bind analyte) which result from conformational or chemical changes caused by the immobilization process. It also compensates for any receptive material which may be unavailable for binding due to poor orientation. Thus, applicant has discovered that in direct thin film assays the surface area limitations require the use or development of special materials and procedures designed to maximize the functional density, viability, stability, and accessibility of the receptive material.

Much of the original work to adapt siliceous materials for retention of specific binding molecules originated with affinity chromatography applications and used silica (SiO$_2$) gel, and solid supports such as glass. Initial activation of silica towards the binding material was accomplished by treatment with a dichlorodimethylsilane. Silanization, regardless of the process used to apply the silane, can introduce groups capable of covalently attaching the molecule by chemical means.

Figure 4:
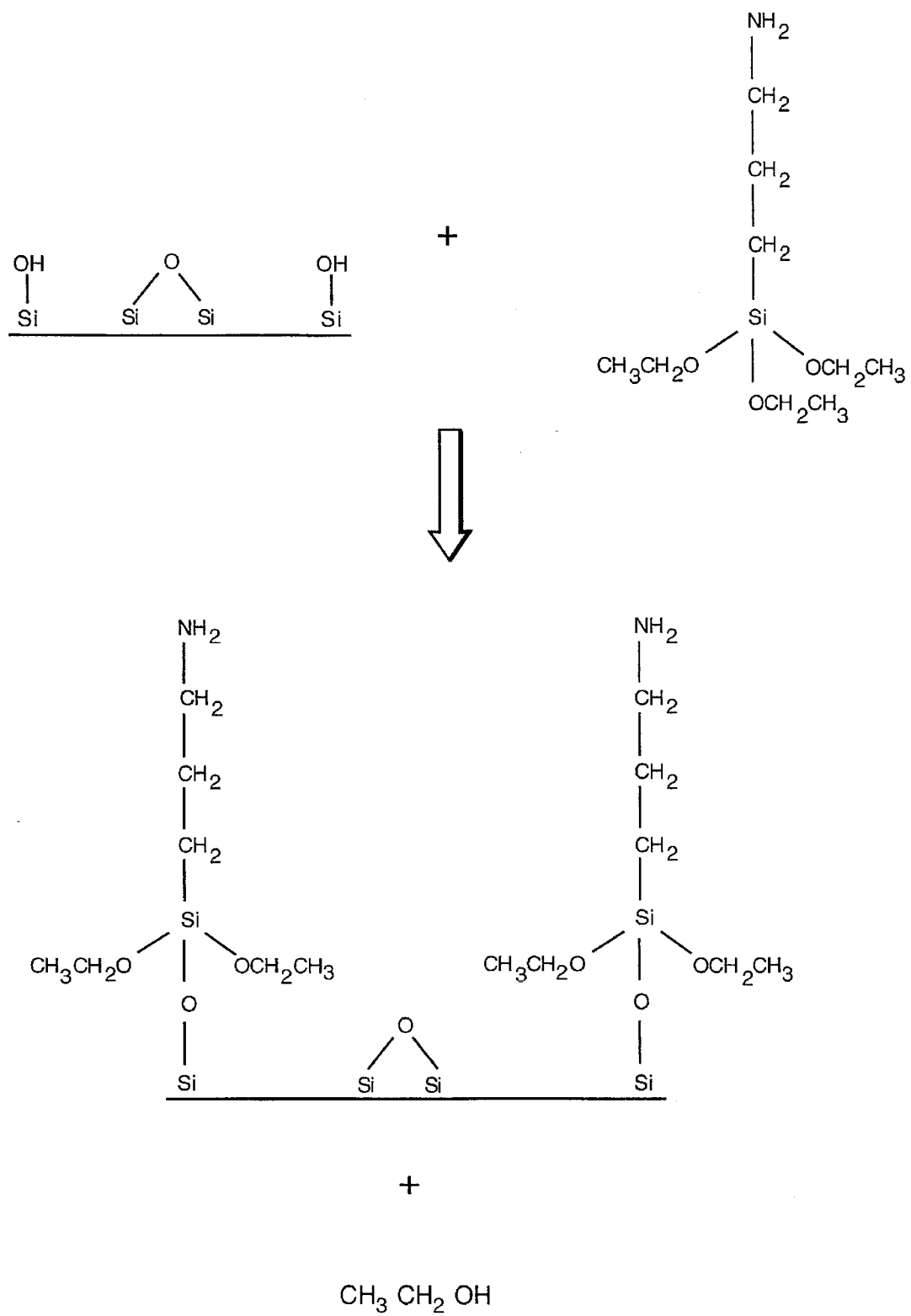
Figure 5:
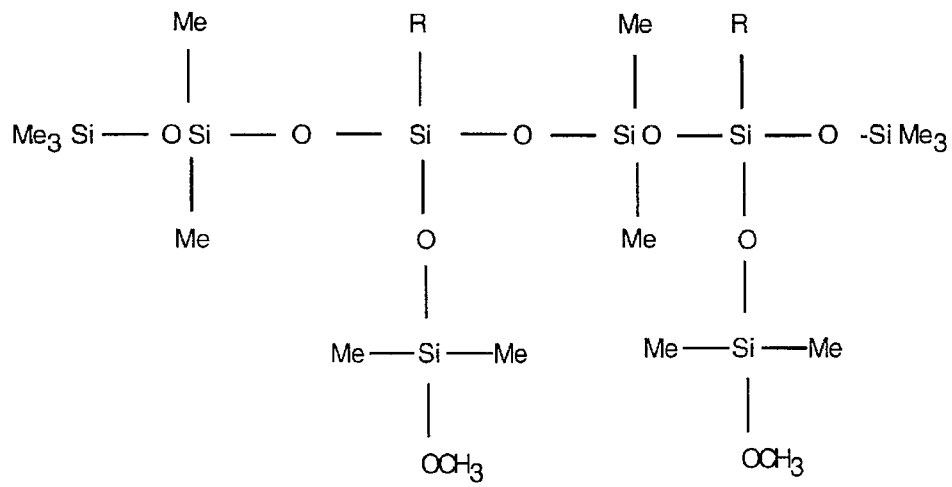
Figure 5:
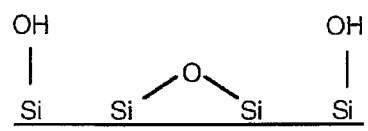
Figure 5:
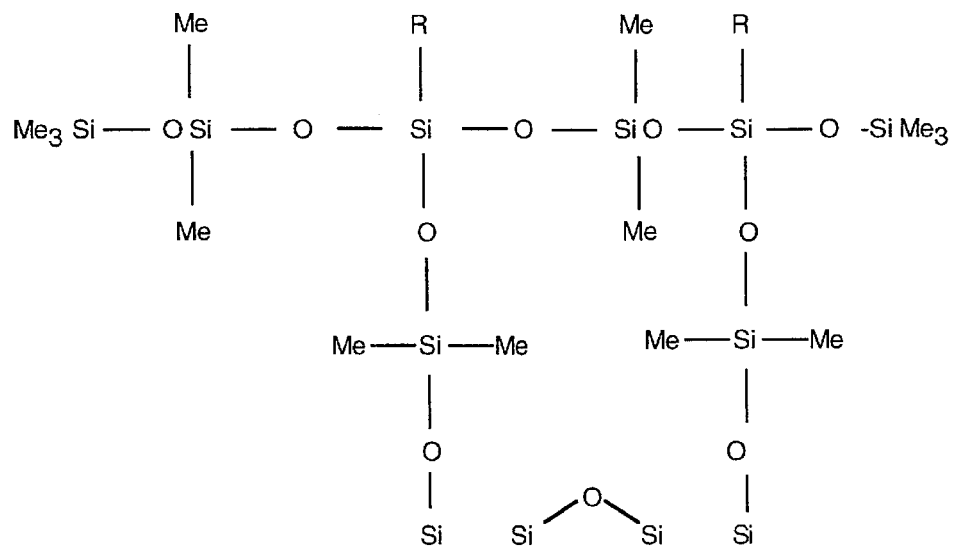
Figure 5:
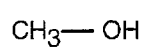
Figure 6A:
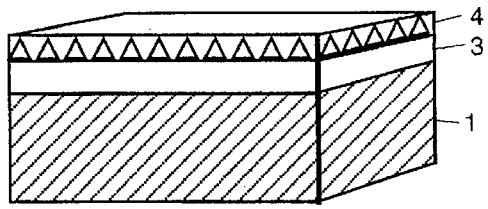
Figure 6B:
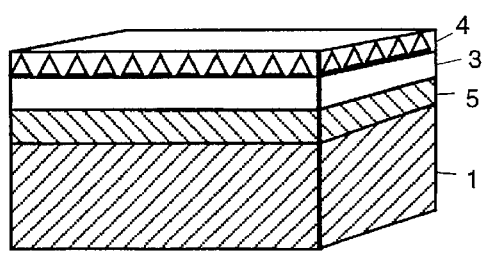
Figure 6C:
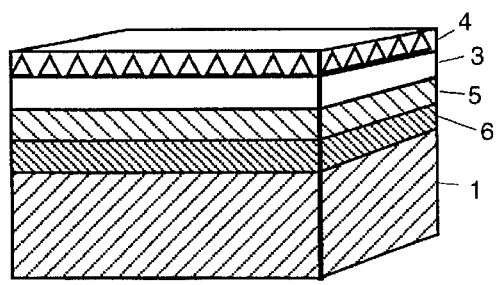
Figure 6D:
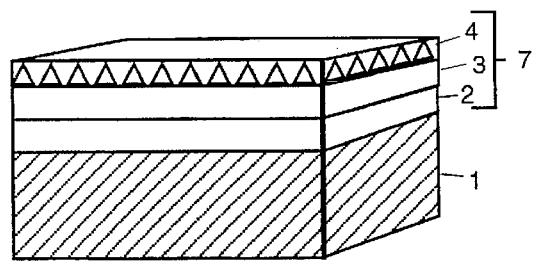
Figure 6E:
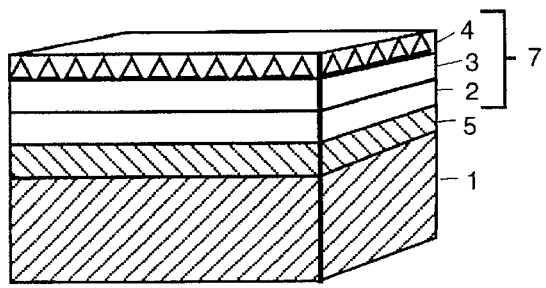
Figure 6F:
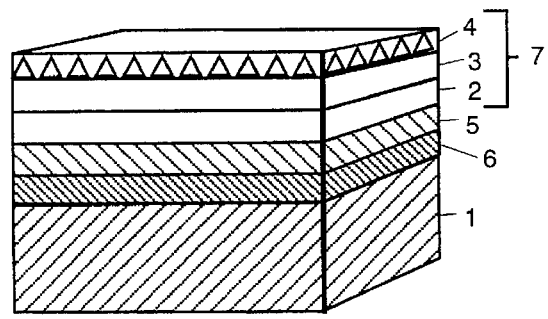

Previously, optically active surfaces have been made hydrophobic by use of dichlorodimethylsilane (C$_2$H$_6$Cl$_2$) which bonds with hydroxyl groups on the surface of silica to attach two methyl groups to that surface. Thus, a slight hydrophobicity results. Applicant has determined that such a reaction does not produce an optimal surface reactivity. Referring to FIG. 4, there is shown in diagrammatic form the bonding of a more useful silane material which bonds to the silica groups present on a substrate. Only bonding of such silane molecules to the surface provides an available group, such as an amine group for bonding with a receptor molecule. It is evident from this figure that the greatest number of biological molecules that can be bonded in this way is equal to the number of silica groups available for interaction with silane. In contrast, as shown in FIG. 5, even more useful attachment molecules of the present invention are multivalent with respect not only to the silica groups present on a substrate (thus, providing a stronger bond), but are also multivalent with respect to the groups that can bond to the receptor molecules since each R group shown in the figure can be multivalent, and can even bond with further siloxanes, if so desired. Those of ordinary skill in the art can readily determine equivalent siloxanes or other molecules which can be used as attachment layers to increase the amount of receptor molecules that may be bonded on any particular silicon-containing or other substrate.

Applicant has discovered that when silicon replaces silica as the solid support or substrate for subsequent attachment, conventional silanization is inadequate in this invention. A silane requires the presence of silanol residues in order to attach to the surface. With monocrystalline silicon, the silanol density is insufficient to yield the density of functional groups desired for immobilization reactions, thus, less than optimal receptive material will be attached to the test surface, see FIG. 4. Silica and many glasses possess a high silanol content or are easily treated to provide a high silanol content. However, silicon also introduces surface effects, not observed with silica or glass, which are toxic or detrimental to biomolecules. Such silanization processes also produce hazardous materials which require disposal, and in many cases are tedious and difficult to monitor and control. While this silanization process provides some level of reactivity, it does not provide the level of sensitivity required for many applications. In addition, amine-containing silanes introduce a number of unique difficulties. One is that amine-functionalized silanes are water soluble and the amine group catalyzes the hydrolysis of the silane from a modified surface. Applicant has discovered that silanes modified with a polymer are functionally better in devices of this invention, e.g., PEI modified silane or its equivalent (FIG. 5).

In a preferred embodiment, the attachment layer is spin coated or aerosol spray coated in a uniform manner. The various intermediate materials are coated to the substrate at thicknesses between 5 Å and 500 Å (thicker amounts can be employed). The layer can be formed of any material that performs the following functions and has the following characteristics: creates a favorable environment for the receptive material, permits the receptive material to be bound in active, functional levels (preferably by a cost-effective method), adheres tightly to the optical substrate, and can be coated uniformly.

Ideally, for direct eye detection methodologies, the surface activation technique should provide a covalent modification of the surface for stability while introducing a very dense uniform or conformal film on the surface of the substrate. A strongly adsorbed conformal film without covalent attachment may be adequate, for example, suitable substrates, such as monocrystalline silicon, macroscopically planar, uniform optical glasses, metalized glass and plastic, whether or not coated with an optical layer (i.e., SiO, $SiO_2$, $Si_xN_y$, etc.) have a deficiency of available reactive groups for covalent attachment, but are useful in this invention. Once applied, the attachment layer should provide an environment which supports the adherence of a specific binding layer by covalent or adsorptive interactions, that is dense and functional. This attachment layer must be of sufficient thickness to separate the specific binding layer from any toxic effects of the initial optical substrate.

Three examples of types of materials that may be used for the production of this test surface are now described. Referring to FIG. 5, non-linear branched polymeric siloxanes may meet the requirements of covalent attachment to the substrate and will adhere receptive material in a reactive and stable film. These polymers typically contain 2–3 branch points which may introduce a number of different functionalities (R) to the surface; including aminoalkyl, carboxypropyl, chloropropyl, epoxycyclohexylethyl, mercaptopropyl, phenethyl, phenethylsulfonate, vinyl, methyl and methacryloxy-propyl (produced by Petrarch Systems). These polymeric siloxanes are particularly useful when a layer of silicon nitride is the upper surface as even fewer silanols are available for attachment. T-structured polydimethylsiloxanes with functionality at the branch terminus include carboxy, propyl, and vinyl groups (Petrarch Systems). Typical examples of these materials are provided in U.S. Pat. Nos. 4,208,506, 3,530,159 and 4,369,268, all hereby incorporated by reference herein.

A second group of materials which demonstrate utility in the production of these test surfaces are copolymeric, conformal, surface activator or film forming latexes which commonly consist of a styrene/polybutadiene mixtures. Although these preparations perform as particles while in solution, they do not retain their particulate nature at a surface or upon drying. These materials are designed to strongly adhere to surface micro-structures. TC7 and TC3 particles distributed by Seradyn and the Surface Activators (amide or carboxylic acid) distributed by Bangs Laboratories or Rhone-Poulenc are particularly well suited to this application. Any similar film forming latex or styrene/butadiene/other copolymer may be used.

Another class of compounds which has utility in the production of this type of test surface is dendrimers, or star polymers, or molecular self-assembling polymers. These polymers strongly adhere to a surface once dried. These materials are generated in a cyclic fashion, each cycle producing a new generation of material. Any generation of material may be used in this application, however, generation 5 (shown diagrammatically in FIG. 18) has been demonstrated to provide the best reactivity. These materials are produced and composed of the materials listed in U.S. Pat. Nos. 4,507,466; 4,588,120; 4,568,737; and 4,587,329. Representative of a ternary dendrimer is the polyamidoamine shown in FIG. 18. In this figure, Y represents a divalent amide moiety. Such as $-CH_2CH_2CONHCH_2CH_2-$ and YN is a repeating unit. The terminal groups may be amines as shown in FIG. 17 but may be any active group which will serve as a dendritic branch for subsequent generations. Other suitable divalent moieties include alkylene, alkylene oxide, alkyleneamine and the like with the terminal being an amine, carboxy, aziridinyl, oxazolinyl, haloalkyl, oxirane, hydroxy, carboxylic esters, or isocyanato group.

All of these materials are stable to organic solvents which improve the spreading capacity on a solid support. This allows the attachment layer to be generated by a spin coating technique which is easy to control and produce in volume. Alternate methods of application include dip coating, spray coating, or other aerosoling techniques. The use of an organic solvent is acceptable because, following the curing process (generally a heat treatment), none of the organic solvent remains to contact the receptive material. The curing process improves the adhesion of the attachment layer to the optical test surface and helps drive the polymerization and condensation processes. Evaluation of each of these materials and the precise methods of producing these attachment layers are presented in Examples 5, 6, and 7, below.

The siloxanes point to a general class of materials that are useful in this application. The siloxanes are not water soluble, and do not hydrolyze upon contact with an aqueous coating solution or sample. Because of the branched structure and the polymeric features, rather than forming a single isolated island as a silane will (FIG. 4), the polymeric structure forms a continuous film (FIG. 5) on the test surface. The highly cross-linked structure of a siloxane increases the total surface coverage. The refractive index of the siloxane film can be controlled or varied with the functional group incorporated into the side chains of the siloxane and thus caused to interact with the other layers to produce an appropriate interference film.

The siloxanes covalently modify the substrate, but this is not an essential feature, as other materials which adhere to the surface without any subsequent delamination and are stable to mechanical manipulation are useful. Methods of coating polymers to substrates are known to those skilled in the art of semiconductor fabrication.

Although not required, additional materials which convey a desired property may be affixed to the attachment layer. This layer could improve receptor material orientation, for example, use of Protein A or Protein G for orienting antibodies. Other materials which can be used include avidin-biotin, synthetic or recombinant Protein A/Protein G fragments or peptides or combined A/G peptides, etc.

The immobilization chemistry for attaching the receptive material to the attachment layer is selected based on the properties of both the attachment layer and the receptive material. The receptive material can be covalently or passively attached to this material. When the attachment layer is specifically adapted for covalent attachment, an additional step to activate the attachment layer may be required. A variety of activation and linking procedures can be employed, for example, photo-activated biotin can be employed to adhere the receptive material. Usually, it is sufficient to passively adsorb the receptive material to the attachment layer, thus avoiding the time and expense of immobilization chemistry procedures.

Receptive Material

The receptive material is defined as one part of a specific binding pair and includes, but is not limited to: antigen/antibody, enzyme/substrate, oligonucleotide/DNA, chelator/metal, enzyme/inhibitor, bacteria/receptor, virus/receptor, hormone/receptor, DNA/RNA, or RNA/RNA, oligonucleotide/RNA, and binding of these species to any other species, as well as the interaction of these species with inorganic species.

The receptive material that is bound to the attachment layer is characterized by an ability to specifically bind the analyte or analytes of interest. The variety of materials that can be used as receptive material are limited only by the types of material which will combine selectively (with respect to any chosen sample) with a secondary partner. Subclasses of materials which can be included in the overall class of receptive materials includes toxins, antibodies, antigens, hormone receptors, parasites, cells, haptens, metabolites, allergens, nucleic acids, nuclear materials, autoantibodies, blood proteins, cellular debris, enzymes, tissue proteins, enzyme substrates, co-enzymes, neuron transmitters, viruses, viral particles, microorganisms, proteins, polysaccharides, chelators, drugs, and any other member of a specific binding pair. This list only incorporates some of the many different materials that can be coated onto the attachment layer to produce a thin film assay system. Whatever the selected analyte of interest is, the receptive material is designed to bind specifically with the analyte of interest. The matrix containing the analyte of interest may be a fluid, a solid, a gas, or a bodily fluid such as mucous, saliva, urine, fecal material, tissue, marrow, cerebral spinal fluid, serum, plasma, whole blood, sputum, buffered solutions, extracted solutions, semen, vaginal secretions, pericardial, gastric, peritoneal, pleural, or other washes and the like. The analyte of interest may be an antigen, an antibody, an enzyme, a DNA fragment, an intact gene, a RNA fragment, a small molecule, a metal, a toxin, an environmental agent, a nucleic acid, a cytoplasmic component, pili or flagella component, protein, polysaccharide, drug, or any other material, such as those listed in Table A. For example, receptive material for the bacteria listed in Table A may specifically bind a surface membrane component—protein or lipid, a polysaccharide, a nucleic acid, or an enzyme. The analyte which is specific to the bacteria may be a polysaccharide, an enzyme, a nucleic acid, a membrane component, or an antibody produced by the host in response to the bacteria. The presence of the analyte may indicate an infectious disease (bacterial or viral), cancer or other metabolic disorder or condition. The presence of the analyte may be an indication of food poisoning or other toxic exposure. The analyte may indicate drug abuse or may monitor levels of therapeutic agents.

One of the most commonly encountered assay protocols for which this technology, can be utilized is an immunoassay. The discussion presented for construction of a receptive material layer below specifically addresses immunoassays. However, the general considerations apply to nucleic acid probes, enzyme/substrate, and other ligand/receptor assay formats. For immunoassays, an antibody may serve as the receptive material or it may be the analyte of interest. The receptive material, for example an antibody, must form a stable, dense, reactive layer on the attachment layer of the test device. If an antigen is to be detected and an antibody is the receptive material, the antibody must be specific to the antigen of interest; and the antibody (receptive material) must bind the antigen (analyte) with sufficient avidity that the antigen is retained at the test surface. In some cases, the analyte may not simply bind the receptive material, but may cause a detectable modification of the receptive material to occur. This interaction could cause an increase in mass at the test surface or a decrease in the amount of receptive material on the test surface. An example of the latter is the interaction of a degradative enzyme or material with a specific, immobilized substrate, see Example 13. The specific mechanism through which binding, hybridization, or interaction of the analyte with the receptive material occurs is not important to this invention, but may impact the reaction conditions used in the final assay protocol.

In general, the receptive material may be passively adhered to the attachment layer. If required the free functional groups introduced onto the test surface by the attachment layer may be used for covalent attachment of receptive material to the test surface. Chemistries available for attachment of receptive materials are well known to those skilled in the art.

A wide range of techniques can be used to adhere the receptive material to the attachment layer. Test surfaces may be coated with receptive material by: total immersion in a solution for a pre-determined period of time; application of solution in discrete arrays or patterns; spraying, ink jet, or other imprinting methods; or by spin coating from an appropriate solvent system. The technique selected should minimize the amount of receptive material required for coating a large number of test surfaces and maintain the stability/functionality of receptive material during application. The technique must also apply or adhere the receptive material to the attachment layer in a very uniform and reproducible fashion.

Composition of the coating solution will depend on the method of application and type of receptive material to be utilized. If a spin coating technique is used a surfactant may improve the uniformity of the receptive material across the optical substrate or support. In general, the coating solution will be a buffered aqueous solution at a pH, composition, and ionic strength that promotes passive adhesion of the receptive material to the attachment layer. The exact conditions selected will depend on the type of receptive material used for the assay under development. Once coating conditions are established for a particular type of receptive material, e.g., polyclonal antibodies, these conditions are suitable for all assays based on such receptive material. However, chemically distinct receptive materials, for example polyclonal antibodies and nucleic acids, may not coat equally well to the attachment layer under similar buffer and application conditions.

It has been demonstrated that when the receptive material is an antibody suitable adhesion is obtained when the attachment layer is a T-structured siloxane. The T-structured siloxanes provide a very uniform hydrophobic surface for antibody interaction, see Example 6.

Surprisingly, the film forming latexes generally provide a better attachment for antigens than do the siloxanes. Antibody interaction with the immobilized antigen is improved on a siloxane modified surface, while enzymatic reaction with a substrate is improved on a latex modified surface relative to a siloxane modified surface.

The materials and methods described above allow the construction of a specific binding test surface. The test surface is composed of an optical substrate or support, an optional optical thin film, an attachment layer, and finally a layer of receptive material. For a visual determination of a specific binding event or interaction, the composite interference film is actually designed to include the optical thin film, the attachment layer and the receptive material. The initial interference color selected must be maintained when the attachment layer and receptive material are coated onto the optical thin film, see FIGS. 3G and 3F. Once a surface is coated with receptive material a small spot of a preparation containing the analyte of interest may be applied to the surface. This is incubated for a few minutes, rinsed, and then dried under a stream of nitrogen. This will generate a procedural control which will be developed whether the sample being assayed is positive or negative. This control assures the end-user, that the assay protocol was followed correctly and that all the reagents in the kit are performing correctly. The procedural control may be applied in any pattern desired.

Like the procedural control the receptive material may be applied in a pattern. Thus, the device will provide a symbol detectable by eye in response to polychromatic light when the optical thin film is applied to the optical substrate. The coating solution containing receptive material may be applied to the surface which is covered with a mask. The mask will allow the receptive material to be immobilized on the attachment layer only in the sections which are exposed to the coating solution. A surface which is uniformly coated with receptive material may be covered with a mask and the receptive material may be selectively inactivated. There are a number of techniques which are suitable for the inactivation of receptive material. One of the simplest techniques for biological materials is to expose section of the receptive material to UV irradiation for a sufficient period of time to inactive the material. The mask may be designed in any pattern which will assist the end-user in interpretation of the results.

Techniques such as stamping, ink jet printing, ultra-sonic dispensers, and other liquid dispensing equipment are suitable for generation of a pattern of the receptive material. The receptive material may be applied in the pattern by these techniques, incubated for a period of time, and then rinsed from the surface. Exposed sections of attachment material may be coated with an inert material similar to the receptive material.

A particularly useful combination of interference colors relies on a yellow/gold interference color for the test surface background or starting point. Once an increase in mass occurs at the surface, mass being a direct function of thickness and concentration, the reacted zone changes interference color to a purple/blue color. As described above, the optical thin film can be adjusted and optimized to compensate for the layers required in the construction of the biological test surface to maintain the desired starting interference color.

Mass Enhancement

Thin film detection methods which provide direct determination of specific binding pairs offer significant advantages relative to radioactive or enzymatic means, including fluorescent, luminescent, calorimetric, or other tag-dependent detection schemes. Thin film systems can be applied in the detection of small molecules. Such analytes, however, fail to produce sufficient thickness or optical density for direct eye or instrumented detection. Applicant has discovered that a means for mass enhancement is necessary. Thin film detection systems, however, perform optimally when the integrity of the film is maintained. Thus, any method designed for amplification in such a system should provide an increase in thickness or mass and maintain the film integrity, as well as meet any limitations imposed by the detection systems, and should be of the simplest possible construction.

C. Fredrik Mandenires and K. Mosbach, 170 *Anal. Biochem.* 68, 1988, describe a method of using small silica particles coated with concanavalin A or an anti-IgG antibody in an ellipsometric assay. Silica particles provide a refractive index which is sufficiently close to the biological layers that they increase the apparent thickness of the biological layers in a concentration dependent manner. These particles being rigid in nature do not, however, maintain the integrity of the films. Thus, light scattering occurs.

The amplification technique may be directly related to the concentration of the analyte of interest or may be inversely proportional to the concentration of the analyte of interest as in a competitive or inhibition assay format. The binding of a mass enhancement or amplification reagent must be a specific function of the analyte binding to the test surface and may be considered as part of a signal generating reagent.

Referring to FIGS. 7A–E, there is shown in diagrammatic form two methods by which the presence of an analyte on a device of the present invention can be detected by signal amplification. For example, the signal may be amplified by contacting the receptive material with analyte labeled with a latex particle or other means which will enhance the thickness of the receptor analyte layers when the two are bound together. Alternatively, the analyte may be labeled with an enzyme, through a secondary binding agent, such that, while the receptor-analyte-enzyme combination may not be detectable, by provision of a substrate for that enzyme, a product is deposited on the test device and can be detected by eye. Applicant has found that it is advantageous to ensure that the surface of the device is charged so that deposition of the product from the substrate is aided.

The mass enhancement reagent must be capable of passive or covalent attachment to a secondary receptive material. An example of passive attachment to a mass enhancing reagent is the adsorption of antibodies onto surface activator particles. An example of the covalent attachment of a mass enhancing reagent to the secondary receptive material is the conjugation of horseradish peroxidase (HRP, or another enzyme) to an antibody. Regardless of the mechanism employed, the mass enhancement reagent should form a stable product or adduct with the secondary receptive material. The coupling protocol selected should not leave or introduce non-specific binding effects at the test surface. The mass enhancement reagent may also be capable of direct, specific interaction with the analyte.

Thus, the invention features methods for the amplification of signals in assay systems which rely on a thin film detection method. Such methods include, but are not limited to, ellipsometry, interference effects, profilometry, scanning tunneling microscopy, atomic force microscopy, interferometry, light scattering, total internal reflection, or reflectometric techniques. The materials selected for use in these types of systems preferably maintain some degree of particulate character in solution, and upon contact with a surface or support form a stable thin film. The film is preferably conformal to the test surface to maintain the desired smoothness or texture of the substrate. The characteristic texture of the surface will be dependent on the detection method employed. The material selected must also be capable of adhering, through covalent or passive interaction, a receptive material or one member of a specific binding pair. A secondary receptive material or binding reagent preferably is adhered to the signal amplifying material or particle in a manner which preserves the reactivity and stability of that secondary receptive material. The secondary receptive material applied to the particle may be identical to, or matched to the receptive material immobilized on the test surface. The combination of a secondary receptive material or binding reagent and additional material, whether a particle, an enzyme, or etc., forms a mass enhancement or signal generating reagent.

In general, an optical assay that requires amplification consists of a substrate whose properties and characteristics are determined by the type of detection method used, an optional secondary optical material, an attachment layer, a layer of receptive material, and the mass enhancement reagent. A general assay protocol requires that the sample suspected of containing the analyte of interest be processed through any treatment necessary, such as extraction of a cellular antigen, and then be mixed with the secondary or amplification reagent. An aliquot of this mixture is applied to the receptive material coated substrate. After an appropriate incubation period, the unbound material is separated from the reacted film by either a physical rinse/dry protocol or with a device contained rinse/dry step. The signal is then interpreted by eye or instrumentally. The introduction of the secondary or amplification reagent can be achieved by addition of a reagent to the sample, as a lyophilized material in the sample collection or application device, or embedded in an assay device.

Polymer Solid

Polymers useful in this invention are conformal (film forming) and do not introduce a particulate character to the surface. A wide variety of styrene-butadiene copolymers have found utility in agglutination assays, immunoassays, and chromatography applications. The latexes commonly used are highly cross-linked, rigid copolymers. The most common use of latex particles in these applications is as the solid support for capture and separation of the desired analyte. Styrene-butadiene copolymers with low cross-linking have been designated surface activators or film forming latex particles. These preparations behave as particles in solution but upon contact with a surface dry to a conformal film. These film forming styrene-butadiene copolymers may contain a wide variety of functional binding groups.

Rigid polystyrene particles also have been used for signal generation by incorporation of a dye. These particles are simply an alternate method for the introduction of a tag or label for signal generation. Use of colored or dyed latexes for agglutination assays and for membrane based assays have been extensively utilized (for a review see L. B. Bangs, American Clinical Laboratory News, May 1990). As in previous cases, the primary requirement for these particles is that they maintain their structure for visualization in agglutination assays and do not distort to block the pores of the membrane-based tests. While covalent attachment provides specific advantages with certain interacting species, passive adsorption of the receptive material to the latex is frequently adequate.

The production of suitable amplifying film-forming latex particles requires the selection of a film-forming particle or surface activator compatible with the secondary reactive species and of sufficient size to increase the apparent thickness or density of the captured analyte.

The secondary reactive species may be immobilized on the surface activator particles by incubation at the appropriate temperature for a period of time. The temperature selected will be influenced by the chemistry utilized to attach the secondary reactive species to the particle, the nature of the reactive species, and the composition of the particle. In addition to the temperature, length of incubation, and chemistry of immobilization, the buffer composition (pH and ionic strength), and the amount of secondary reactive material must also be optimized to the particular application.

The specific examples (14 and 15) given below are intended to be illustrative of the type of method(s) used for the production of the film-forming amplification reagent. The conditions described are not intended as a limitation in the preparation of such amplification reagents. The styrene/butadiene/vinyl copolymers are the preferred film forming latex compositions. However, any styrene/butadiene copolymer which maintains the film forming property is acceptable. The functional group may be of any chemical composition which will support the adhesion or interaction of a secondary binding reagent, where the secondary binding reagent will specifically bind with the analyte of interest. The TC7 and TC3 formulation distributed by Seradyn and the Surface Activator formulations distributed by Bangs Laboratories or Rhone-Poulenc are preferred (the catalogs of which are hereby incorporated by reference herein). More conventional latex particles (referred to as $S/B/V-CONH_2$, $S/B/V-COOH$, $S/V-CONH^2$, $S/R-NH_2$, $S/HYDRAZIDE$, $S/V-COOH$, $S/B-COOH$, $S/B-CONH2$, $PS$, $S/VBC$, $S/A/V-COOH$, $PMMA-COOH$, $S/A-OH$, $S/R-OH$, and $S/R-SHO$) have demonstrated some utility in this invention, but tend to produce a more diffuse signal than the film forming latexes.

Catalytic Production of Solid

Applicant has found that even more sensitive optical thin film assays can be obtained with an enzyme/substrate pair which produces insoluble precipitated products on the thin film surface. The catalytic nature of this amplification technique improves the sensitivity of the method. Enzymes which are useful in the present invention include glucose oxidase, galactosidase peroxidase, alkaline phosphatase and the like. However, any process which provides a specific component which can be attached to a receptive material and can catalyze conversion of a substrate to a precipitated film product is suitable to this technology. An insoluble reaction product results when immobilized antibody-antigen-antibody-HRP complex is present on the test surface. The product is precipitated by the action of a precipitating agent such as combination of alginic acid, dextran sulfate, methyl vinyl ether/maleic anhydride copolymer, or carrageenan and the like, and with the product formed by the interaction of TMB (3,3',5,5'-tetra-methyl-benzidine) with an oxygen free radical. This particular substrate will form an insoluble product whenever a free radical contacts the TMB. Other substances such as chloronaphthol, diaminobenzidene tetrahydrochloride, aminoethyl-carbazole, orthophenylene-diamine and the like can also be used. These are used in concentrations from about 10 to about 100 mM. It is by these means that a measurable increase in mass occurs with the enzyme-conjugate layer. The color signal is unaffected by the underlying color of any chromophore present in the substrate solution. A variety of enzyme substrate systems or catalytic systems may be employed that will increase the mass deposited on the surface.

Examples of such an enzyme-labeled antibody methods in thin film assays for the detection of low levels of the polysaccharide antigens derived from the group of bacteria commonly responsible for bacterial infections in man, such as Meningitidis and Streptococcus are presented in Examples 16, 17, 18.

Figure 7A:
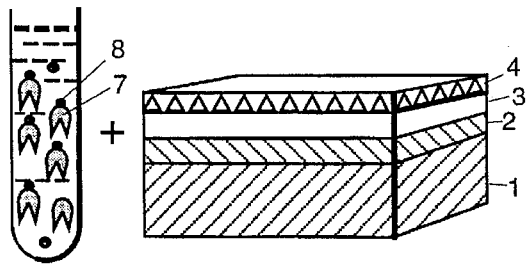
Figure 7C:
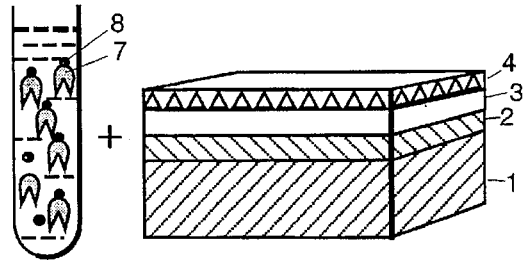
Figure 7B:
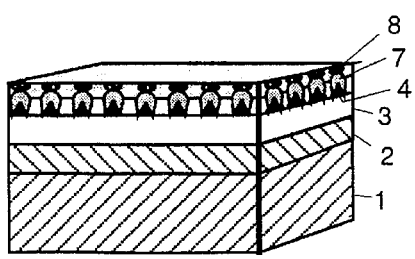
Figure 7D:
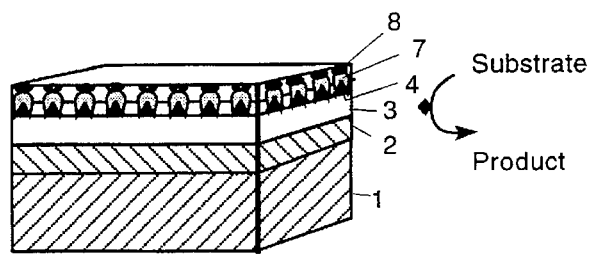
Figure 7E:
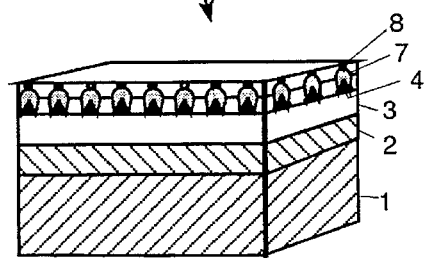

Referring to FIGS. 6A–F, there is a graphic representation of a cross-section of the multilayer device having a substrate upon whose upper surface, various layers are coated. In one example, these layers include a layer of silicon nitride immediately adjacent to the upper optical substrate layer, an attachment layer such as a polymeric siloxane, and the receptive material, which for a bacterial antigen assay is an antibody. Referring to FIGS. 7C–E, when the analyte is present, a complex with the enzyme-labeled antibody and analyte is simultaneously formed on the test surface. It is over this mass that the substrate is added to cause the product precipitate described to form.

If desired, the analyte of interest may be combined with the mass enhancing reagent and the immobilized receptive material either in a simultaneous or sequential addition process. Either mechanism results in the formation of an analyte/mass enhancement reagent complex which is immobilized on the test surface. Thus, the mass enhancement reagent may be mixed directly with the sample. This mixture may then be applied to the reactive test surface and incubated for the required period. This is a simultaneous assay format.

In some cases additional sensitivity is gained by performing a sequential addition of the sample followed by the mass enhancement reagent. Any mechanism or specific interaction can be exploited for the generation of a mass enhancement reagent. For instance, nucleic acids are known to tightly bind or intercalate a number of materials, such as metals, and certain dyes. These materials would serve to introduce mass into a specifically immobilized nucleic acid.

The increase of the product layer may be determined by various means including a visual means or by the use of instrumentation, such as ellipsometry and where light intensity differentials are caused by the increased thickness. The receptive material enzyme complex is thus capable of direct interaction with the analyte of interest and more particularly is evidence of an analyte, such as an antigen. This change is detectable by measuring the optical thickness and does not necessarily depend on any light reflectivity of the substrate material. One such instrument is the Sagax Ellipsometer, described in U.S. Pat. Nos. 4,332,476, 4,655,595, 4,647,207, and 4,558,012, which disclosures are incorporated in full and made a part hereof.

Devices

Several configurations of the above multilayer test surface in a device format are possible. The simplest assay format is a single use, single sample device. A more complicated device allows for a single sample to be screened for the presence of multiple analytes. Additional devices allow multiple samples to be screened for a single analyte or batch testing.

The single use device provides an easy to use format which is adaptable to a wide range of assays, such as infectious disease testing, pregnancy or fertility testing, etc. Protocols for using these single test devices are very simple. The sealed device is opened exposing the reactive test surface. Sample is applied to the test surface and incubated for a short period of time, for example, 2 minutes. The sample may or may not require pre-treatment, such as antigen extraction from bacteria, etc. Addition of a secondary reagent to the sample prior to application to the test surface may also be required. Once the incubation period is complete, the unreacted sample is removed with a water rinse. The device is blotted to dry the test surface. Depending on the test and the mass enhancement/amplification method used, the assay is complete or the assay may require additional incubation/wash/dry cycles. The test device and protocol are well suited to physician office, clinical laboratory, home or field testing environments. A protective shell is preferably provided around the device, e.g., composed of polystyrene, polypropylene, polyethylene, or the like, which is readily formed into a molded or injection molded devices. Multi-analyte or multi-sample devices may be made of similar materials using similar processes.

Single Use Device

Specific examples of such devices are shown in the Figures.

For example, referring generally to. FIGS. 8A–8G, a single use device may be packaged in any size of molded device, but in this example has a length of 1.74 inches and a width of 2.22 inches and a depth of 0.375 inches for the closed device. The device is constructed of a base which will hold the test surface and an absorbent pad for retaining the wash solution and excess sample. The device lid is designed to hold a blotter pad which will remove excess moisture from the test surface. To secure the absorbent pad in the base of the device or the blotter in the lid a thin sheet of plastic is attached to each portion of the device by a living hinge. The base and the lid of the device are joined by a living hinge. However, any clasp or hinge combination which will allow multiple opening/closing cycles is acceptable. Once the absorbent pad and blotter are placed in the device these covers are closed to secure the materials. These plastic covers provide protection to the end-user by preventing exposure to the wash solution and excess sample contained within the absorbent materials. The lid of the device may be designed with or without a clasp but it is preferred that a tight seal be obtained. The device should be easily disposed of or of a convenient size for storage. All components of the device, except the reactive test surface, may be sterilized if required.

The upper blotter pad has several unique requirements. The composite blotter material must be set in the lid of the device directly over the test surface. When the lid is closed and the rinsed test surface is contacted by the blotter pad, the test surface must compress into the blotter pad sufficiently to preferentially blot solution vertically away from the test surface. The blotter pad may be mounted on a small plastic slide such that fresh, dry material is presented to the test surface for additional wash/dry steps. The initial material in the blotter is selected to rapidly wick water vertically from the surface, i.e., the paper has a high rate of absorption, while the subsequent materials have high absorptive capacity and will remove solution horizontally from the test surface. The blotter material next to the surface must not shed or scratch the optical test surface. Whatman's Grade 1Chr paper serves this function very well but alternate materials are acceptable. Any highly absorbent material may be used as the additional layers in the blotter pad. Two additional pads in combination with the Grade 1Chr layer have been found to be optimal for a two stage drying process. The layers may be free or laminated together. When a multi-step rinse/dry is required, the slide supporting the blotting material has a handle for positioning fresh blotter over the test surface. This handle fits into openings in the protective shield over the base of the device to prevent the blotter from moving when it is contacting the test surface.

The reactive test surface is mounted on a pyramidal shaped pedestal which extends above the base of the device. Rinse solution flows over the test surface and down the faces of the pedestal where it is trapped in the adsorbent pad. The pedestal also positions the test surface so that it is compressed into the blotting material when the lid is closed. The test surface mounted on to the pedestal may range in size from 0.5 cm$^2$ to 1.0 cm$^2$ with 0.75 cm$^2$ being preferred. The only limitation on the size of the test surface for an eye-visible assay is that some unreacted test surface be visible for contrasting to the reacted zone. As the interference color change or other signal produced for a positive response is permanent, the test device may be sealed and stored as a permanent record.

Figure 8A:
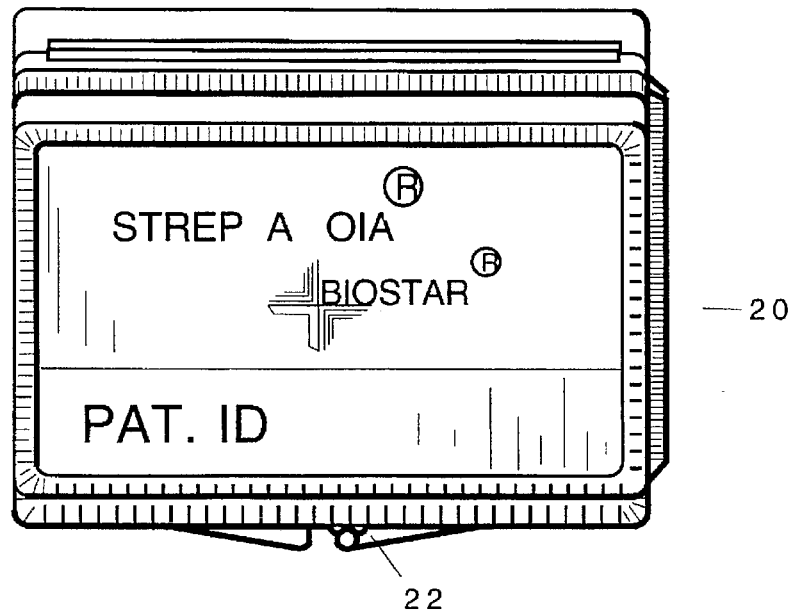
Figure 8B:
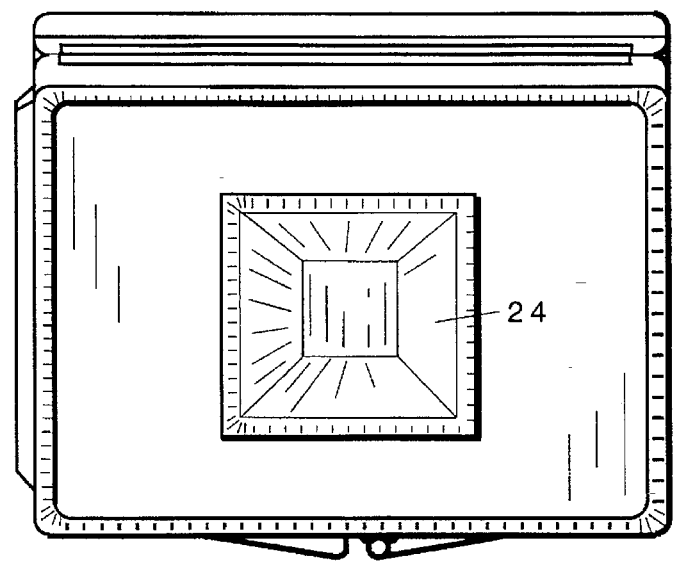
Figure 8F:
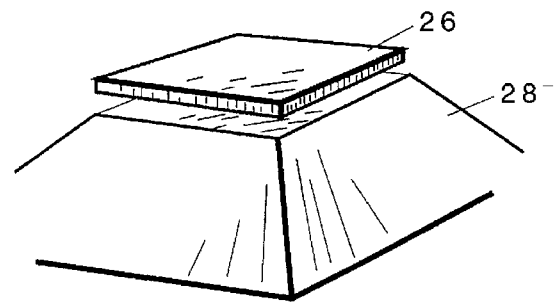

Referring to FIGS. 8A–8G, a single use device of the present invention is shown. Specifically, device 20 is formed of a readily moldable hard plastic material (with a clip 22) to prevent damage to the test surface present within the device, and to ensure appropriate alignment of components of the device. The lower surface of the device is indented at indent 24 such that the test surface is raised relative to other internal components (as shown in FIG. 8F), in which a test surface 26 is raised on a pyramidal structure 28. A hinge 30 is provided on the edge opposite clip 22 to allow raising and lowering of the upper half 32 of the device relative to the lower half 34.

Referring specifically to FIG. 8E, test surface 26 is provided in lower half 34 of the device raised on a pyramid 28 as discussed above, such that liquid placed on surface 26 may flow from that surface and down pyramid 28 into an enclosed area beneath plate 36 which has an upper surface located at the same height as the containing wall 38. Plate 36 is attached by a hinge 40 to one side 42 of lower half 34. Within plate 36 are provided two apertures 43 and 44.

Upper half 32 of the device is provided with a second plate 46 which is also attached by a hinge 48 to upper half 32 along one edge 50. Two apertures 47 and 49 are provided within plate 46. Beneath plate 46 is filter paper 52 along with a movable plate having a handle 56 which can be moved, as shown by arrow 58, from a position on the right hand side of aperture 48(I) to a left hand position within that aperture (II). Such movement causes movement of filter paper 52.

Figure 8G:
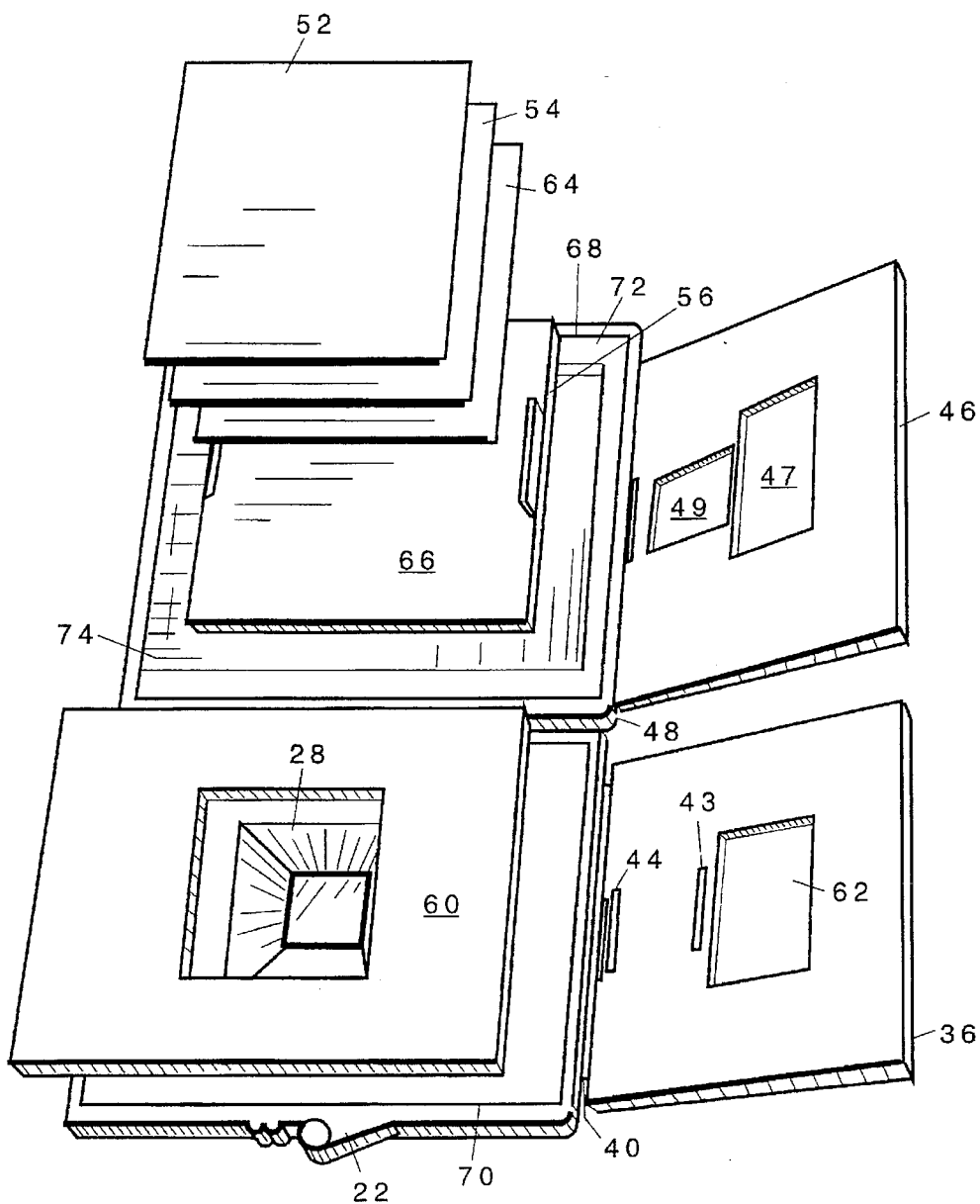
Figure 9A:
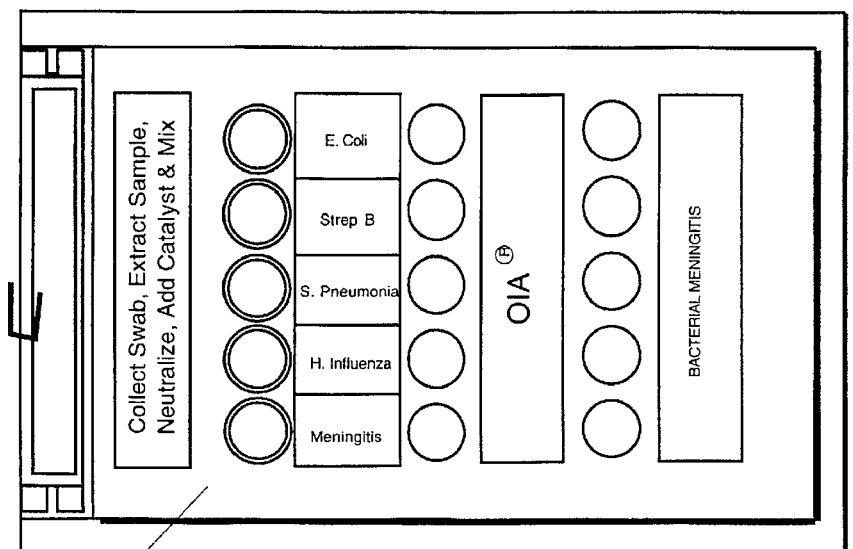
Figure 9B:
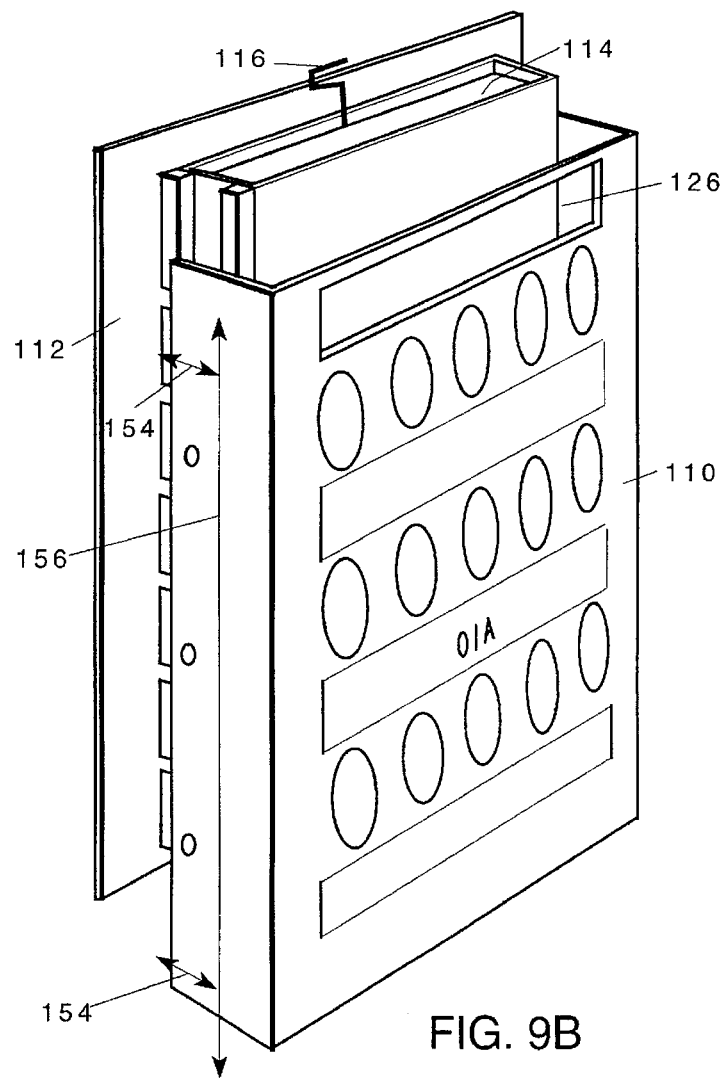
Figure 9C:
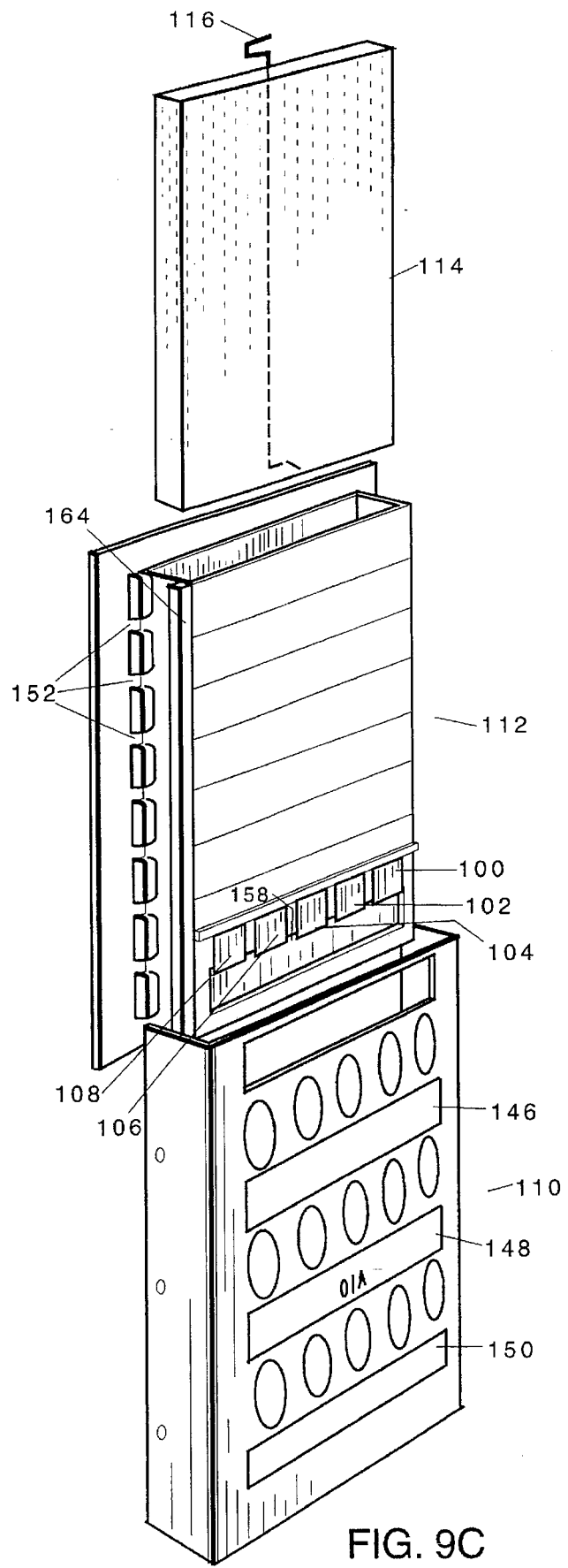
Figure 9D:
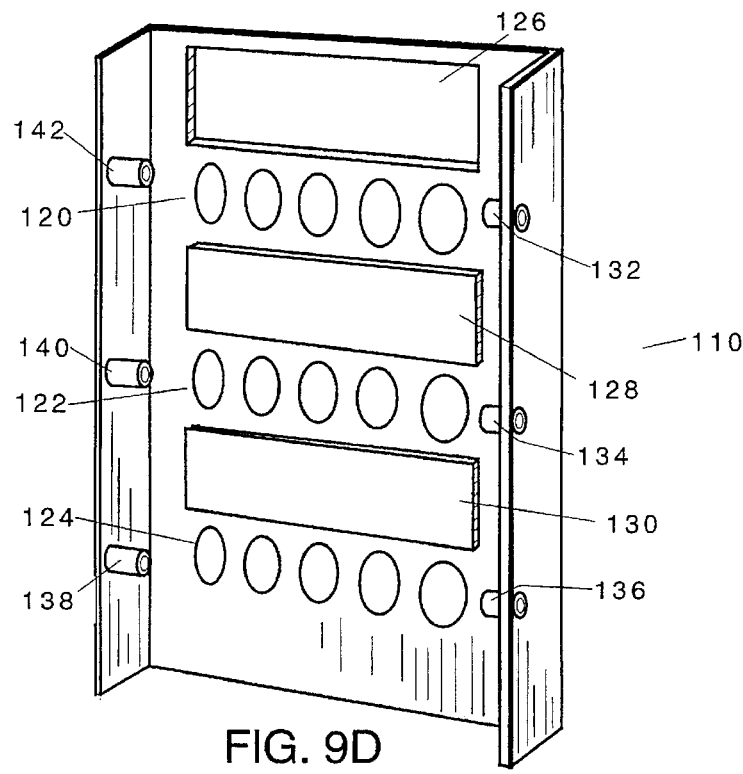
Figure 9E:
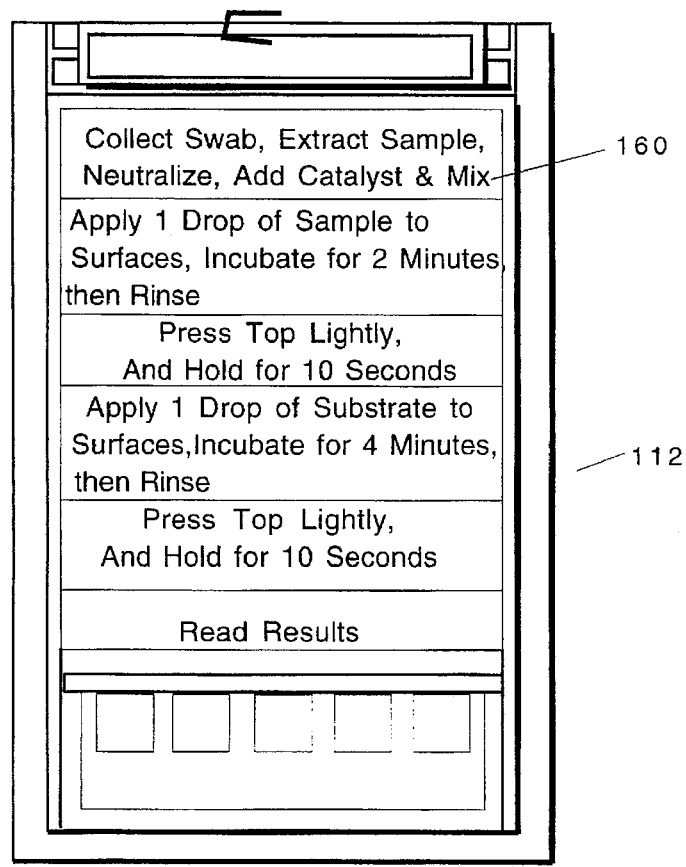

Referring now specifically to FIG. 8G, plates 36 and 46 can be removed from their position shown in FIG. 8E by rotation about hinges 40 and 48, respectively. Beneath plate 36 is a thick filter pad (absorbent) 60 designed to absorb liquid passing from pyramid 28. An aperture 62 is provided within plate 36 to allow plate 36 to fit over pyramid 28. Beneath plate 46 is provided filter papers 52, 54 and 64. Filter papers 52, 54 and 64 are caused to move from the left to the right relative to hinge 48 by movement of handle 56 from position I to II in FIG. 8E as noted above. Apertures 43 and 44 are provided within plate 36 to cooperate with handle 56 when it is in both position I and position II so that device 20 can be closed during use of the device. Specifically, the exposed level of filter paper 52 is such that when the device is closed the surface of filter paper 52 contacts the surface of test device 26, and absorbs liquid on that surface. Movement of handle 56 (and the attached plate 66) causes a new portion of filter paper 52 to be available for contact with test surface 26 when the device is closed again.

This device can be manufactured using standard procedures. Specifically, once the plastic molding has been formed, filter papers 52, 54 and 64 can be placed within the upper portion of the device and plate 46 secured over those papers to hold them within upper portion 32. Similarly, filter paper 60 can be secured within lower portion 34 by securing plate 36. Both plates 36 and 46 are provided with a plurality of small extrusions along their edges (not shown) which are adapted to mate with a lip portion 68 and 70, respectively, to hold those plates in place. Also provided is a shelf 72 within upper portion 32 to allow plate 46 to rest on the shelf, and to allow movement of filter papers 52, 54 and 64 within the inner space 74. No such shelf is necessary in lower portion 34 since the filter material is relatively thick, and no movement of that filter is required. Test surface 26 is readily attached to pyramid 28 by adhesive, or other means.

Use

Figure 10A:
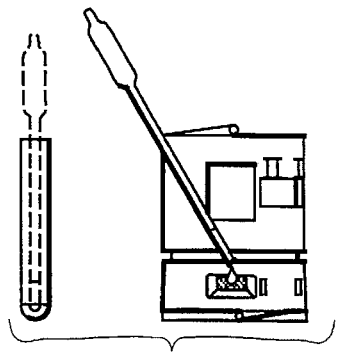
Figure 10B:
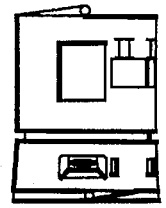
Figure 10C:
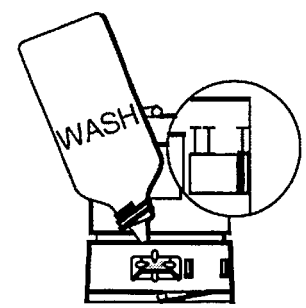
Figure 10D:
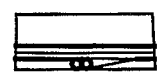
Figure 10E:
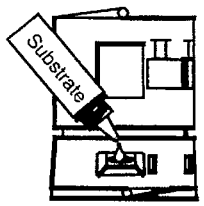
Figure 10F:
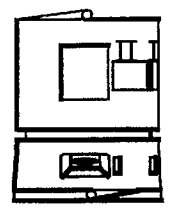
Figure 10G:
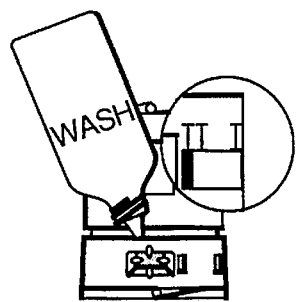
Figure 10H:
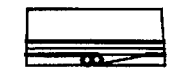
Figure 10I:
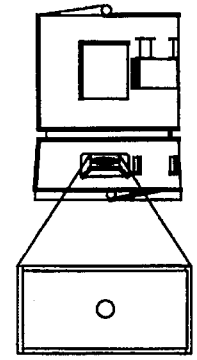

Referring to FIGS. 10A–I, there is shown a method by which device 20 may be used in a method of the present invention. Specifically, in a first step (FIG. 10A) 1 a sample is obtained and treated in an appropriate manner to prepare for application to the test surface. Such application is performed with the device open. In a second step (FIG. 10B) the sample is allowed to incubate so that any analyte present in the sample can react with the receptor layer. At a third step (FIG. 10C) the sample is washed from the test surface and the excess liquid allowed to flow into the filter below the pyramid holding the test device. At this stage the position of the upper filter material is at I. In a fourth step (FIG. 10D) the device is closed and latched so that the filter may blot the test surface. In a fifth step (FIG. 10E) an appropriate substrate is added, allowed to incubate (FIG. 10F) and then again (FIG. 10G) as above. At this point, the upper filter material is moved from position I to II, and the device again closed to allow the test surface to be dried (FIG. 10H). At this point, the device is again opened and the result can be read (FIG. 10I).

Multi-test Device

Referring generally to FIGS. 9A–9E, and 11A–E, a device which will examine a single sample for multiple analytes incorporates many of the features of the single use device. The device's first position exposes a number of test surfaces, each uniformly coated with a different receptive material. The device has the test protocol imprinted on the upper surface to assist the end user. Any number of test surfaces may be mounted into the device, but five independent assays are very easily accommodated. Sample is applied to each of the test surfaces and incubated. Following the incubation period the test surfaces are rinsed with water. The test surfaces are mounted over a sloping trough which will drain the rinse solution and excess sample into an adsorbent pad in the bottom of the device. The lid is lifted and advanced to a second position. This brings a blotter pad into contact with each test surface to dry them as described in the single use device. The lid is lifted and the test surfaces are exposed once again. As with the single use device the test may be ready for interpretation at this point, or may require additional incubation/rinse/dry cycles. The device is easily extended to accommodate the required number of steps. This type of device would be particularly useful for screening patients for drugs of abuse, allergy screening, meningitis screening, sexually transmitted diseases, TORCH panels, and the like. The test protocol is fairly simple and would be well suited to physician office, clinical or reference laboratory testing. Field use would be possible when urine or whole blood is the sample to be screened. For this example it was assumed that each reactive test surface was presented in the device as a separate 0.75 cm$^2$ test piece uniformly coated with receptive material. It is possible to apply each receptive material in discrete lines or spots across the surface of a test piece. The test device would then approach the size of a single use device.

It is also possible to design a device with multiple pedestals which very closely approximates the single use device. In this case the living hinged lid would contain ports which are positioned precisely above each test surface mounted on a pedestal. The wash solution and excess sample could be collected in an absorbent pad surrounding each pedestal or could flow through a porous solid pedestal support to a reservoir below.

The optical substrate or support may be cut to any size desired, thus, the reactive test piece may be any size required. A uniformly coated test surface could be of sufficient size that a standard microtiter well format could be designed. The wells provide a reservoir for sample application without cross contamination and exploit existing EIA assay automation technologies. The test device could be a simple plate, of any size, spotted with receptive material at pre-set x,y coordinates such that sample application is driven off of these coordinates. Cross-contamination between samples could be controlled by hydrophobic wells surrounding the reactive zones, other types of physical barriers, or by microspot sampling techniques. These types of multi-sample, single analyte test devices may be adapted to semi-automated or fully automated instrumentation, see FIGS. 12A–C. For batch testing, an instrumented rather than eye interpretation is preferred. Batch testing surfaces may be dried using a blotter design, a heat lamp or other such device, or may include a forced air or nitrogen drying method. Sample residue and contaminated rinse solution could be drained into a reservoir where it is treated prior to disposal. Or the excess sample and rinse solution could be drawn into a sealed section of the test device.

Batch or multi-sample devices may be designed in qualitative, semi-quantitative, or quantitative testing formats. Surfaces for batch testing may be any size. The size will be determined by the number of controls and samples to be performed in a single assay. Automated sample handling devices and sample application devices will impact test surface size. Automated sample handling and batch testing applications include screening blood for blood banks, as well as those for clinical and reference laboratories. These laboratories may require high volume, limited testing menus; high volume, large testing menus; or low volume, large testing menus. The flexibility in test surface design allows all of these requirements to be met with a single optical detection method. Additional sample handling and test device manipulation may be required to increase the volume of samples or the number of tests performed.

Specifically, referring to FIGS. 9A–9E, there is provided in diagrammatic representation a multi-test device of the present invention. This specific example is designed to test for the presence of *E. coli*, Streptococcus B, *Streptococcus pneumoniae*, H. influenza and *N. meningitidis*. Generally, this device is constructed with a plurality of test devices, namely five test devices, 100, 102, 104, 106 and 108. The device has an upper slidable cover 110, a lower shelf portion 112 which includes a large thick filter material 114 which is removable from section 112 by use of a wire loop 116. Upper cover is provided with three series of five apertures 120, 122 and 124 and with a large rectangular aperture 126. On its under surface are provided two absorbent wipes 128 and 130 formed of a filter material, and adhesively bonded to the lower surface of cover 110. General indicia may also be provided on the surface of cover as shown at 146, 148 and 150.

Also provided are a series of three cylindrical extensions extending approximately 4 mm from the inner surface of cover 110, labeled 132, 134, 136, 138, 140 and 142. The cylindrical extensions are adapted to mate with spaces 152 provided in the lower portion of portion 112 such that each row of apertures in the upper cover can be specifically positioned over the test devices or other indicia in lower portion 112, as desired. This movement is shown generally in FIG. 9B by arrows 154 and 156.

Lower portion 112 is further provided with an aperture 158 located to allow excess liquid on test surfaces 100, 102, 104, 106 and 108 to drain within portion 112 and to be absorbed by filter 114. Lower portion 112 is further provided with a series of instructions shown as 160 which are revealed in turn as cover 110 is moved in a stepwise fashion as dictated by the mating of cylindrical extensions 132, 134, 136, 138, 140 and 142 relative to spaces 152 along slidable portion 164 so that the user of the device has an indication of what step is needed to perform an assay of the invention. The upper and lower portions are constructed such that the filter paper 128, 130 is caused to contact the surface of each test device at an appropriate time in the assay procedure.

Figure 11A:
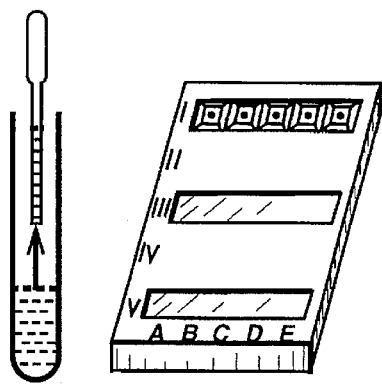
Figure 11B:
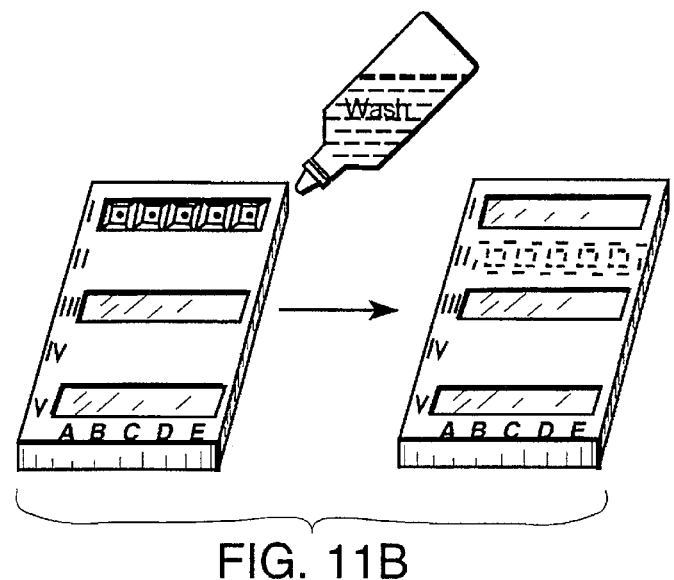
Figure 11C:
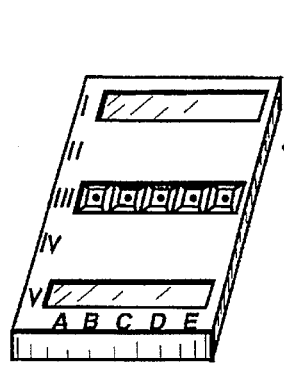
Figure 11D:
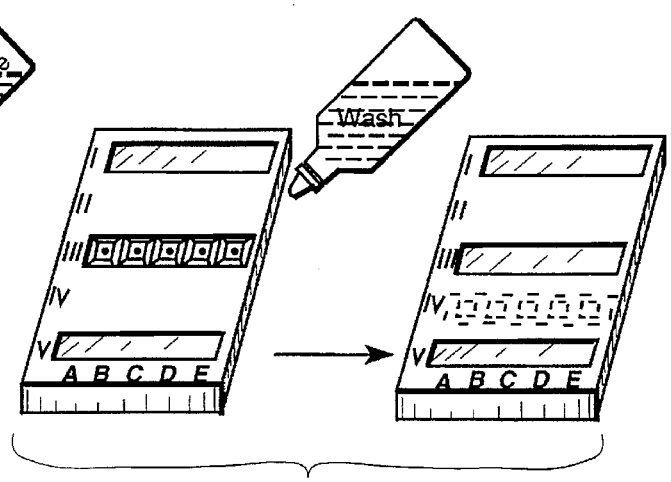
Figure 11E:
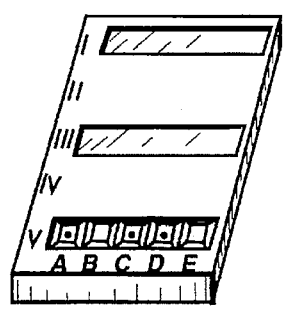

Referring to FIGS. 11A–E, there is shown in diagrammatic form a method of using the multi-assay device shown in FIGS. 9A–E (although the extension of the upper portion versus the lower portion is not shown specifically). At step 1 (FIG. 11A), a sample is collected and appropriate reagents mixed with it. The sample is then applied to each test device and that device is moved one notch (i.e., one cylindrical extension is moved along arrow 156 to the next available space 152) so that the test surface is available for such application. In step 2 (FIG. 11B) the surface is again moved such that first filter material 130 is in contact with the test surfaces. Prior to this step, the test surfaces are washed and that wash solution allowed to drain through aperture 158 to filter 114. After blotting, the device is again moved one notch to allow access to the test surfaces and substrate is applied (FIG. 11C). Once more, after appropriate incubation time, these surfaces are washed, with the wash solution draining to filter 114. The upper surface is then moved one more notch so that filter 128 contacts the test surfaces (FIG. 11D). One more movement of the two surfaces relative to one another allows reading of the results (FIG. 11E). At each step in the process, aperture 126 indicates the step that must be taken by the user, and thus prevents incorrect use of the device.

Figure 12A:
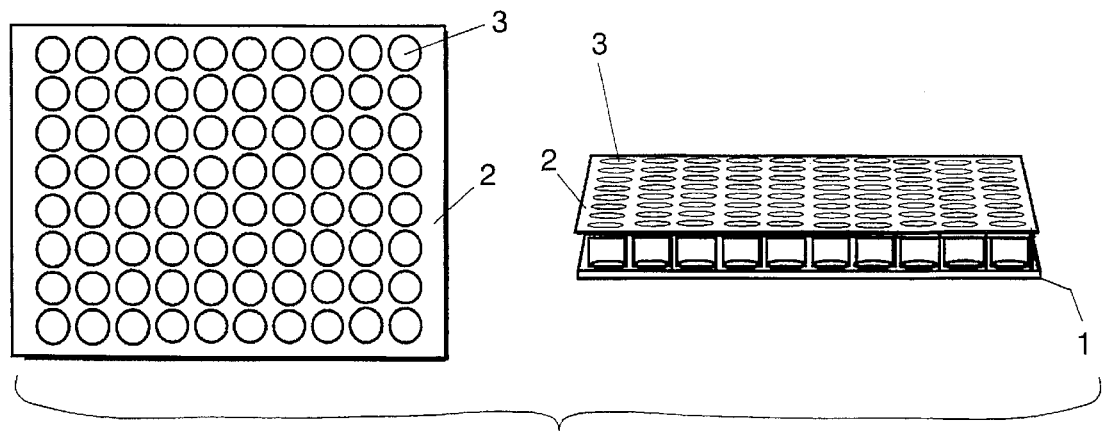
Figure 12B:
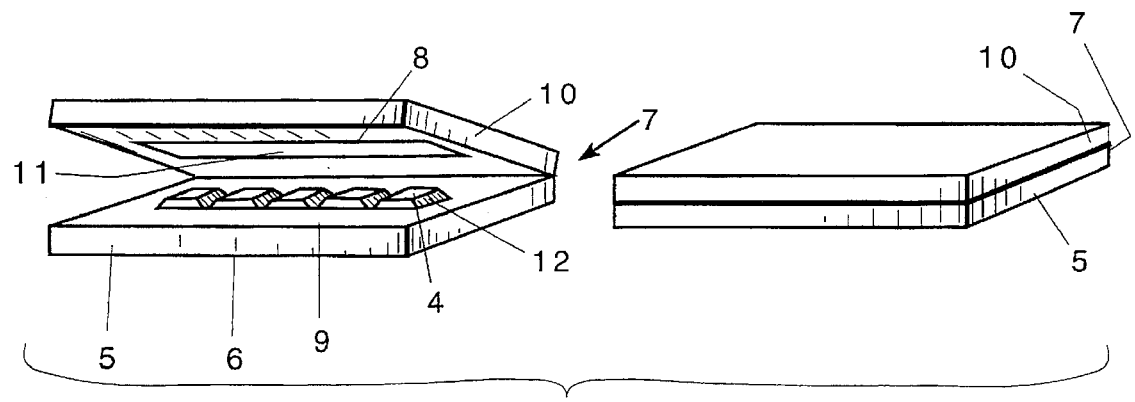
Figure 12C:
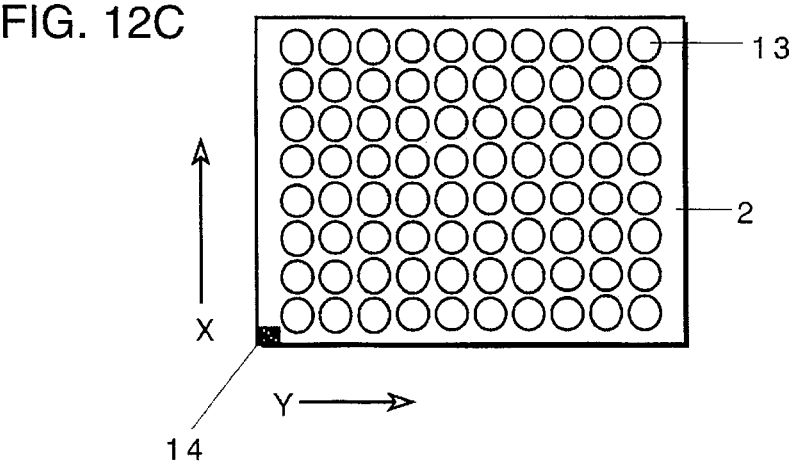

FIGS. 12A–C are diagrammatic representations of a three batch sampling concepts useful in this invention. The first device (FIG. 12A) includes an optically active, analyte reactive test surface #1 prepared as previously described. The test surface #1 is fused or glued to a plastic device #2 which will create individual sample wells #3. The final device will be configured and handled in precisely the same fashion as a 96 well microtiter plate. This configuration of the test surface #1 could be easily adapted to any commercially available microtiter based, handling system.

The second configuration for batch testing is a device very similar to the single use device and would be particularly useful in quick panel screening assays (see FIG. 12B). The device in configured to include a lid #10 which is hingedly attached by a hinge #7 to a bottom container #5. Bottom container #5 holds an absorbent #6 material to contain the excess sample and wash solution. Lid #10 contains a blotter #11 which is used to dry test surface #4 in the assay protocol. The test surfaces are mounted on a pedestal #12 to facilitate the washing process. Protective coverings #8 and #9 hold blotter #11 and absorbent #6 in place within the device The third concept is an optically active, analyte reactive test surface #1 which contains reactive areas represented by #13 (see FIG. 12C). The reactive area #13 may be created by spot coating, by selective inactivation of the receptive layer, or physical barriers between reactive areas. The samples are applied to the reactive areas (#2) and then the rinse solution and excess sample flows out through the drainage port #14.

In another configuration, the test surfaces can be made as a series of longitudinal strips with filter material on either or both longitudinal edges, and arranged to fit within a 96-well configuration.

Instrumentation

After the sample is contacted with the surface of a test device, an instrument can be used to detect analyte binding. One such instrument is the Sagax Ellipsometer (see, U.S. Pat. Nos. 4,332,476, 4,655,595, 4,647,207 and 4,558,012, which disclosures are incorporated in full herein and made a part hereof). Alternate instruments suited to this technology include traditional null ellipsometers, thin film analyzers (see FIG. 14A), profilometers, polarimeter, etc. If the interference film is included in the test surface construction, then a simple reflectometer (see FIG. 14B) is adequate for quantitation.

Figure 13:
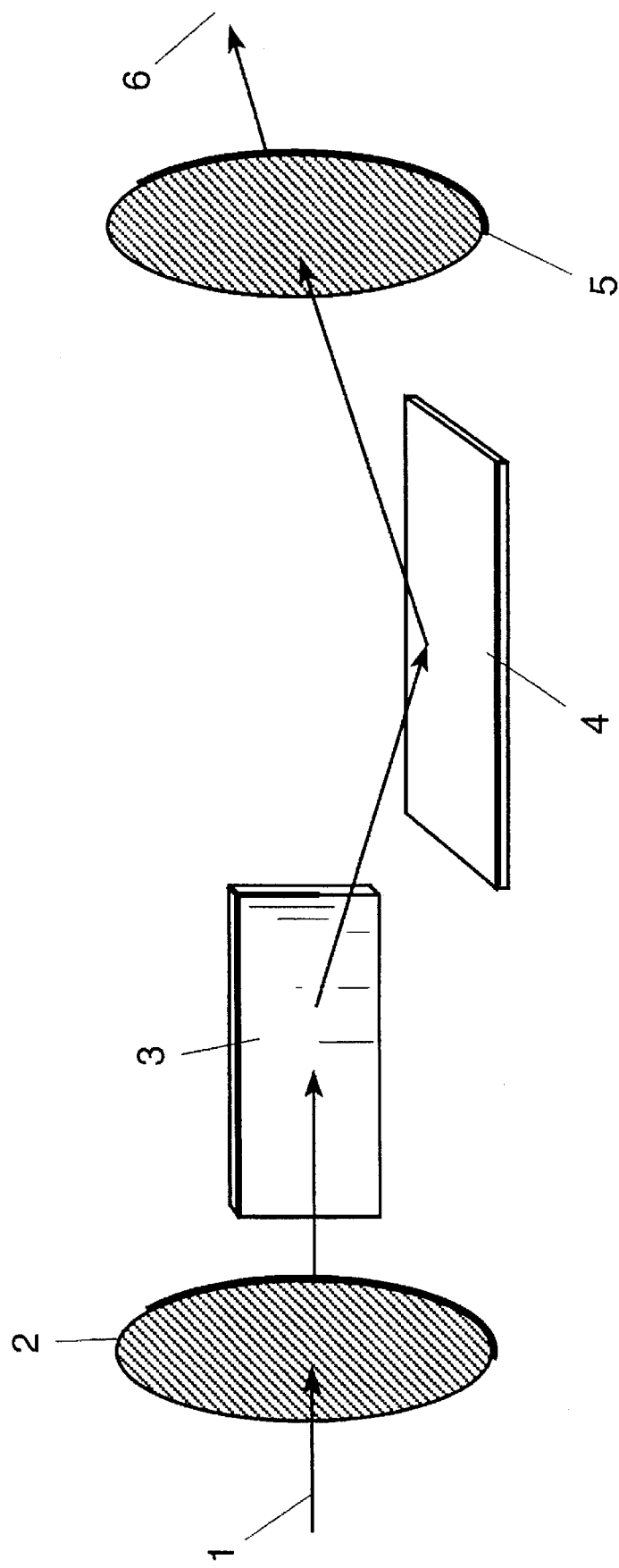
FIG. 13 is a diagrammatic representation of a prior art ellipsometer optical path.

Referring to FIG. 13, there is shown a prior art method for detecting interaction of a light with a test surface. In the prior art, two polarizers were provided to allow such detection. Specifically, #1 corresponds to the white light source used in this prior art instrument. A standard halogen lamp is used to generate the polychromatic light. The light is incident on the polarizer at position #2, and is then linearly polarized. The linearly polarized light then impinges on the reference surface #3 which is at 70° with respect to the test surface #4. The linearly polarized light is reflected from the reference surface (#3) as elliptically polarized light. The light then impinges the test surface (#4) and is reflected to the second polarizer at position #5. The interaction of the light with test surface (#4) inverts the s- and p-components of the elliptically polarized light. The polarizers at position #2 and #5 are matched and #5 is rotated 90° relative to #2. Light which is reflected from the test surface #4 which matches that reflected from the reference surface #3, will pass through polarizer #5 and be completely extinguished at the detector (#6). If there are any differences in the surface properties of surfaces #4 and #3, then some residual ellipticity will cause an increase in intensity to be measured at the detector #6.

Such an instrument which is useful for analysis of thin films and changes in film characteristics is the Comparison Ellipsometer described in U.S. Pat. Nos. 4,332,476, 4,655,595 and 4,647,207. The optical pathway of such instruments is shown in FIG. 13, as discussed above. This instrument can use a reference surface with a wedge of thicknesses across the surface. If thickness values are scribed onto the wedge, the thickness of a test surface may be determined relative to the wedge. The test surface thickness equals the wedge thickness at the point where light is extinguished at the detector.

The instrument operates on the basis of comparing the degree of elliptical polarization, caused by the reflection of plane polarized polychromatic light, between two surfaces. Incident polychromatic light is collimated and plane polarized. The polarized light is reflected at an oblique angle from the reference surface, which is a reflective substrate with similar or identical optical characteristics to that of the test piece. The reflected light is then elliptically polarized as a result of reflection. The elliptically polarized light then reflects from the test surface. The test surface and reference surface are arranged perpendicular to one another such that after reflection from the test surface, the light is once again plane polarized where the test and reference surfaces are optically identical. If their thickness and/or refractive indices are not identical, the light retains some elliptical character. The ellipticity is a function of the refractive index and the thickness differences. A second polarizer is then used to filter the light, and removes the plane polarized light corresponding to identical films. An increase in ellipticity will result in greater light transmission through the second polarizer. Thus, a change in thickness or refractive index is transformed into a change in light intensity which may then be measured using conventional techniques. By employing the Comparison Ellipsometer in this fashion, resolution to ±5 Å may be achieved. Unlike conventional ellipsometry, the Comparison Ellipsometer is designed to allow broad field measurements. This feature allows simultaneous measurement of the entire reaction zone. Therefore, measurement errors do not arise because of non-homogeneous binding or reaction patterns.

For the applications of this invention, a more useful reference surface is one which is uniform. When a test surface to be analyzed has all the components for colored signal generation for visual interpretation, the reference surface must also contain the optical thin film coating. This additional coating is not required for the instrumented analysis. To maximize the signal produced by a change in thickness or mass on the test surface, the reference standard should be approximately 50 to 100 Å thinner than the test surface, substrate, attachment layer, and receptive material. If these two surfaces are too closely matched, then a small change in thickness or mass will result in only a small increase in intensity relative to the original background intensity. The change in intensity for small thickness changes is dramatically increased when the background intensity is above a certain minimum or is sufficiently bright. With this reference surface all changes in thickness or mass cause a dramatic change in intensity of light measured by the detector relative to the test surface's initial reading. The change in intensity may reflect an increase in thickness or a decrease depending on the application, see Examples 8, 12, 13, 16, and 17. The instrumented reading protocols are given in Example 21.

For the analysis of specific binding reactions on a test surface, a number of modifications greatly improve the performance of the Comparison Ellipsometer. The original design relied on the observer's eye for inspection of the surface.

Figure 14A:
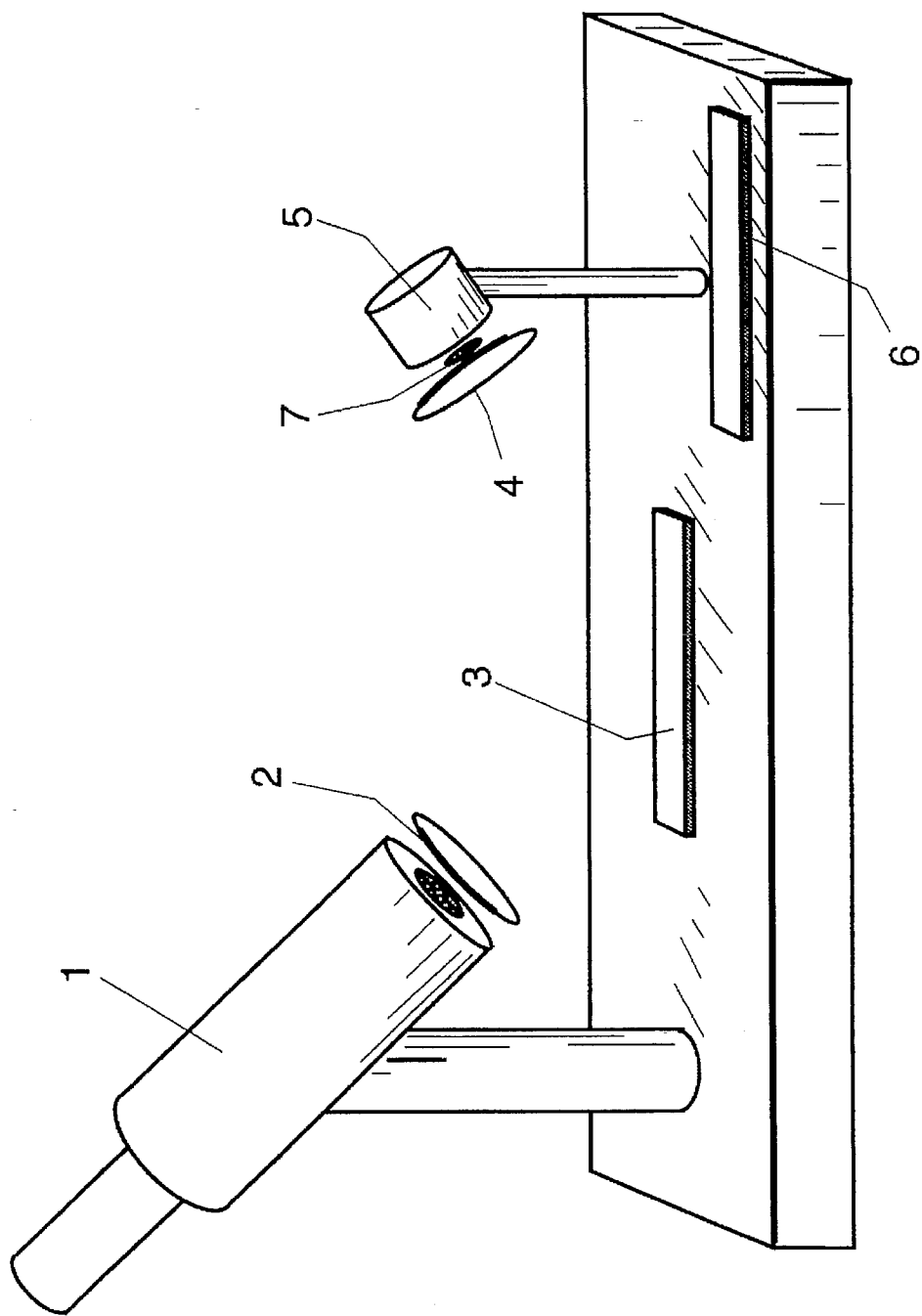
FIG. 14a is a diagrammatic representation of a thin film analyzer useful in the present invention which uses a monochromatic light source and a single photodiode or array.
Figure 14B:
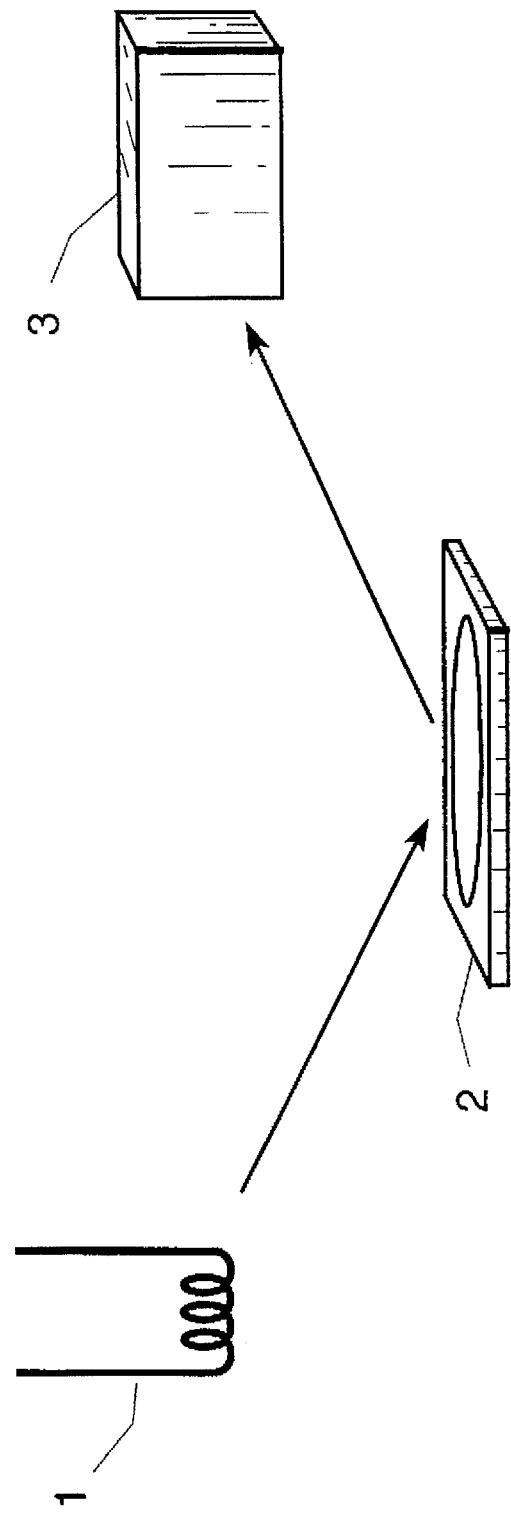
FIG. 14b is a diagrammatic representation of a polychromatic light source and a photomultiplier detector.

Referring to FIGS. 14A and 14B, there are shown two devices in which no polarizers are provided, and in which a thin film can be analyzed either with a single photodiode, an array, or a CCD detector array, or with a reflectometer a photomultiplier detector.

The detector may be mounted where the eyepiece is located in the original instrument. It may also be mounted at 90° to the side of the light path by incorporation of a partially silvered mirror or beamsplitter set at 45° to reflect a portion of light to a detector, and the rest to the eyepiece for visual alignment of samples. If the mirror is inserted into the optical path, the spot intensity reaching the detector will be only a fraction of the light available. If the detector is directly in the optical pathway without a mirror, 100% of the sample intensity reaches the detector. When a beamsplitter and eyepiece are included in the apparatus, if care is not taken, stray light can be introduced which degrades the optical signal incident on the detector.

A photodiode array may be programmed to dedicate individual photodiodes to measure the intensity of reaction zones or spots, while other photodiode arrays measure the background, or control zones. Simultaneous measurement of the spot intensity and the background intensity allows each reading to be accurately corrected for test surface background.

Either a linear array or a matrix array may be used. A linear array may only measure along one, pre-set axis of the sample spot depending on the size and resolution available in the arrays. The matrix array could measure the entire reacted spot plus background.

The instrument may also be modified to include a variable magnification function or a zoom to allow different spots to fill the photodiode without capturing any background signal.

Specifically, two such instruments are represented diagrammatically in FIGS. 14a and 14b. The thin film analyzer (FIG. 14a) uses a monochromatic light source #1. If the light is not sufficiently linearly polarized, then a polarizer at position #2 is used to polarize the light. Polarizer #2 must be positioned to allow the maximum intensity of light to pass through to the test surface #3. By off-setting the initial polarizer a component of light polarized perpendicular to the plane of incidence, in addition to the light polarized parallel to that plane, is allowed to interact with the surface. Light impinges the test surface #3 at an angle which is sufficiently removed from Brewster's angle, between 50 and 75 degrees off the normal. The polarizer/detector is set at the same angle from the normal as the incident light source relative to the test surface. The polarizer is set from 2° to 15° above the setting which aligns the polarizers for total extinction of light. Incident angles of 30° to 40° off the normal provide adequate resolution of very dilute samples, but may not provide sufficient range for all applications. The second polarizer, or analyzer polarizer, cannot adequately minimize the background signal when the light is incident on the surface at angles greater than 65°. However, the dynamic range is sufficient to allow for electronic reduction in the background signal. The light is reflected from the test surface #3 through the polarizer/analyzer combination at position #4 prior to being measured at the detector #5. The detector may be a single photodiode or a photodiode array. A blank test surface is placed in the sample position and used to align the second polarizer. The second polarizer should be positioned at an angle with respect to the first polarizer such that it is a few degrees off the minimum (maximum extinction of light through to the detector). Thus, the background of the test surface produces a low detectable signal, but the change in light intensity is now a function of the change in thickness. See Example 26.

The reflectometer (FIG. 14b) is a very simple instrument which allows measurement of a color change or a change in intensity. At position #1 a standard halogen light source is used. This will provide polychromatic light. The light source #1 is positioned relative to the test surface #2 such that the maximum intensity of the incident light impinges the test surface #2. The detector #3 may be a photomultiplier and the like. The angle with which the light impinges the test surface #2 determines the angle at which the detector #3 is placed relative to that surface #2.

Referring to FIG. 15, in one specific example, a semi-reflective mirror was introduced between the zoom and the ocular at 45°. Within the ocular, suitably positioned in the middle of the field and in focus was set a reticle of an ellipse. The reticle was selected to match an average sample spot size. On the optical path center line, reflected 90° from the principal axis, was set a mask which matches the size of the reticle. The distance from the center of the mirror to the reticle is the same as from the center of the mirror to the mask. The mirror was mounted by adjusting screws so that the image seen within the reticle would be identical to the image appearing within the mask. Behind the mask, a distance of a few millimeters, was mounted a photosensitive cell arranged to only read the light which passes through the mask and therefore from the selected image. The semi-reflective mirror is of a thickness such that a secondary image appears from the second surface. This is eliminated by using a suitably coated thin mylar membrane as the beamsplitter.

A constant light source, white light or monochromatic, is provided by using a power supply that has feedback capabilities. A photoresistor is mounted inside the original instrument's lamp house/heat sink which monitors the light output of the lamp. If the light output changes a corresponding resistance change occurs, thereby affecting the current/voltage sent to the lamp.

The power supply is set to deliver +15 $V_{DC}$ to the lamp while the photoresistor is disconnected. When the photoresistor is connected, it maintains the light output at the level that is produced with a +15 V source. A constant light source is required if the instrument is to be used for quantitation. The instrument may also be modified with a BNC port that will enable the output of the photodiode detector amplifier to output to an A/D converter board in a computer or other dedicated device. The dedicated device or computer reads the input signal, designates/names and stores the input, manipulates the named input, i.e., conducts statistical analyses, etc., and prints the input data and any other desired calculations derived from the input.

Specifically, FIG. 15 is a diagrammatic representation of a modification of the prior art instrument shown in FIG. 13. A constant power source is used at position #1. The power source supplies both the white light source #2 and the detector #12. The white light source is a standard halogen lamp and provides polychromatic light. As previously described the light passes through a polarizer at position #3 and is linearly polarized. Polarizer #6 is matched and crossed relative to the polarizer at position #3. The reference surface #4 and the test surface #5 are as previously discussed. In this instrument, when light passes through polarizer #6 it then impinges a beam splitter at position #7. This beam splitter splits the light such that a portion is received at the detector #12 and a portion is received at a CCD camera at position #11. CCD #11 allows the user to locate and position the test surface #5 in the center of the instrument's field of view. The light which is split to the detector impinges a mask at position #9. The mask is matched to the reticle at position #10 such that when the sample spot on the test surface #5 is precisely centered in the reticle #10, the light which passes through the mask #9 to the detector #12 is reflected only from the sample spot. A zoom at position #8 assists in the positioning of the sample spot relative to the reticle.

The optical path used for the comparison instruments described above are larger than desired for a number of applications. It is possible to reduce the optical path with the following modifications. Because light emitted from a laser source (gas laser or laserdiode), is already collimated and polarized, the collimating lens system can be simplified or eliminated. A linear polarizer is placed very close to the light source. This polarizer may not be necessary because the laser is often polarized. The reference surface is placed at 60°–70° relative to the sample surface. The planes of incidences of the reference and sample surfaces are orthogonal to each other. The analyzer polarizer is oriented so that maximum extinction occurs for two identical surfaces placed at the reference and sample positions. It is important that both polarizers are placed with their faces perpendicular to the light beam. Any suitably small detector and electronics may be used for signal collection, handling, and storage. For high accuracy, polarizers should supply greater than $10^5$ extinction, see FIG. 16. Polarizers are built into the face of the light source and detector and are not labeled on the figure.

The thin analyzer eliminates the reference surface requirements of the previous instrument and is easier to reduce in size. The comparison based instruments require that a specific reference surface be designed for each type of test surface to be used. This limits the range of optical substrates and optical thin films which are compatible with a given instrument, unless means for changing the reference surface is provided. This new instrument easily accommodates any combination of thin film and optical substrate using a simple adjustment of the analyzer. The instrument may provide better thickness resolution. This instrument and the modified Comparison Ellipsometer may be powered with a 9 V battery or other rechargeable power supply. This prototype supplies an increase in numerical aperture, image brightness and focus. This allows a much higher level of magnification to be used which is important for work with smaller spot sizes. Samples may also be applied much closer to one another than is possible with the Comparison Ellipsometer.

Specifically, FIG. 16 is a diagrammatic representation of an improvement in the prior art instrument of FIG. 13. In this case a monochromatic light source #1 is used. A compact laser is used. A polarizer is positioned immediately adjacent the light source at position #1. The lens system used in the prior art instrument to supply visual inspection of the test surface #4 in FIG. 13 is eliminated which allows a decrease in the total optical pathway to be achieved. The test surface rests and is positioned with the sample platform at position #2. Light impinges the reference surface #3 and is elliptically polarized as discussed for the prior art instrument of FIG. 13. The light reflects from the reference surface #3 to the test surface positioned on the sample platform #2. A small electronics control unit (#4) is incorporated to supply a constant power source and to control the detector #5. A single photolode is used as the detector #5. The dial at position #6 is used to move the sample platform #2 and controls the position of the test surface. The sample platform #2 has pre-determined stops which will align a sample spot with the detector #5. The sample spot is positioned and the detector #5 masked such that only signal from the sample spot is measured by the detector. A second polarizer is placed immediately in front of the detector #5.

Fluorescent Methods

A further instrumented embodiment that these optically active substrates, or solid supports, can address is a reflective fluorescence method. The fluorescence may be generated in an immunoassay, an enzyme assay, a nucleic acid assay in a homogeneous, heterogeneous, competitive, or direct format. Signal generation is not dependent on the film thickness in this method, however, the method does double the pathlength of the exciting incident light as well as improves the collection efficiency at the detector (see FIG. 17C). The optically active substrate, or solid support, may be any polished reflective material, such as a silicon wafer.

In standard fluorescence spectroscopy, the exciting light passes once through the sample, see FIG. 17A. When a reflective substrate is used excitation of the fluorescent species occurs at the point (17B) of incidence and at the reflection point. Generally, emission (fluorescence) is detected 90 degrees off the axis of excitation, even though fluorescent radiation is emitted in all directions, primarily to simplify the detector design. For example, with a point detector, excitation energy should not be allowed to strike the detector. Gratings are frequently used with the excitation source, and the maximum fluorescence may not be shifted far enough to be distinguished from the excitation wavelength. This is required to reduce the effects from the high intensity excitation source and scattering from the solution and the cell walls. With a reflective substrate, the detector and the incident light are at equal angles from the normal.

Attempts have been made to increase fluorescent assay sensitivity by increasing the number of passes of the exciting light through the sample. This approach requires more complicated optics for focussing, a high output light source, and large collection optics. This method also tends to increase the background, fluorescence from the cell and interfering or inherent biomolecules. An increase in sensitivity may also be achieved by increasing the sample volume and/or the optical pathlength. The method of the current invention provides an increase in sensitivity without the complications observed with these methods.

British patent GB 2 065 298 A describes a fluorescent assay which uses a reflective metal substrate generated by an evaporation process. The capture layer uses a specifically reactive biological particle for the binding of analyte and then a third biological species which is bound to the fluorescent label. The metal substrate is positioned to redirect the exciting particle toward a trap (multiple reflections) and away from the detector.

This patent positions the photon counting system a distance from the substrate to allow the exciting particles to be reflected by the metal surface toward a dark enclosure. The enclosure will absorb all the photons that hit it which reduces the noise at the detector, while more induced signal from the substrate will travel to the photon counting system due to the reflection. The analyte is reacted in a humid incubation.

For this approach, there must be nothing in the path of the exciting photon which starts from the light source and ends at the wall of the dark enclosure except the highly reflective metal surface and the biological particles. With the incident angle being equal to the reflecting angle and the signal detecting system being perpendicular to and at some distance away from the substrate, the exciting particle will not be scattered toward the detecting system.

The current invention relies on an attachment layer between the reflective substrate and the receptive, biological layer. This polymeric layer between the substrate and the biological layer does not impact the generation of the fluorescent signal. The attachment layer may be selected from any of the following chemicals: dendrimers, star polymers, molecular self-assembling polymers, polymeric siloxanes, and film forming latexes. The method for production of these surfaces is described in Example 5. The reflective substrate or support (optically active surface) may be selected from monocrystalline silicon, glass/amorphous silicon composite, a metal, a ceramic, polycrystalline silicon, a plastic/amorphous silicon composite, and composites of these materials. Methods for the production of these materials is described above. This method doubles the excitation pathlength without doubling the volume of sample. In addition, coating the reflective substrate with a material anti-reflective to the exciting light eliminates the noise frequently associated with fluorescent methods but still allows excitation because extinction occurs at the air/film interface only. Suitable materials include silicon nitride, silicon/silicon dioxide composites, silicon oxynitride, titanium dioxide, titanates, diamond, oxides of zirconium, and silicon carbide. The material and the thickness of the material are selected to suppress light of the exciting wavelength. The exciting wavelength selected is dependent on the specific dye (fluorophore) or label used. These materials are produced as described above. Steeper angles of incident excitation help reduce the amount of exciting light which reaches the detector.

Any number of fluorescent molecules could be utilized in this embodiment. Fluorescent molecules such as xanthene dyes which includes fluoresceins, rhodamines, and rosamines are suited to this application. In addition the amino and carboxylic acid or isothiocyanate substitutes of these dyes are also suitable. Napthylamines such as 1-dimethylaminonapthyl-5-sulfonate, 1-anilino-8-napthalene sulfonate, and 2-p-toluidinyl-6-napthelene sulfonate are also useful. Conjugation protocols for these compounds to biological molecules are well known to those skilled in the art. The label may be attached to a secondary antibody, to an enzyme substrate, to a nucleic acid probe, or any suitably selective and specific receptive material for the analyte of interest.

In the current invention, the optically active or reflective support, with or without the optical coating or AR film, would be coated with a suitable polymer. The polymer layer would then be coated with a receptive material specific to the analyte of interest, i.e., an antibody. The biologically reactive, reflective substrate would be contacted with a sample suspected of containing the analyte of interest and incubated for a period of time sufficient to bind the analyte to the surface. The analyte may be mixed with the secondary receptive material labeled with the fluorescent material simultaneous with contact to the surface or sequentially. In either case, the label is then immobilized to the surface through the analyte bridge. The immobilized label is exposed to the exciting light source and the detector will measure the level of fluorescence. The amount of fluorescence may be measured directly, inversely, or indirectly related to the concentration of the analyte of interest. Similar schemes for detection of enzyme activity or nucleic acids maybe readily derised by those skilled in the art. The light source and the detector can be selected from any combination of standard fluorescent optical components.

Analytes

Streptococcus

Group B Streptococcus (GBS), *Streptococcus agalactiae*, is the leading cause of neonatal and maternal morbidity and mortality. Neonatal infections include sepsis and meningitis, while post-partum the organism causes endometritis, chorioamnionitis, and sepsis. For the neonate, the early-onset disease occurs between birth and the following week. The disease is characterized by respiratory distress, sepsis, and shock. There are between 1.9 to 3.7 cases per 1,000 live births in the U.S. alone, with a mortality rate of 26% to 50%, and 30% of the infected infants developing meningitis. Of the latter group, 50% will suffer permanent neurological damage. Infection with GBS accounts for approximately 2,000 neonatal deaths per year and is estimated to cost the U.S. alone over $500 million per year in health care. Direct correlation of maternal cervical/vaginal carriage of GBS and infant infection has been demonstrated.

GBS also causes a late onset disease that occurs within the first 3 months following birth. The illnesses in these cases are characterized by central nervous system disorders, meningitis, and bacteremia. There is an approximately 20% mortality rate for infants with these diseases.

Maternal colonization is primarily cervical/vaginal and anorectal. Between 5% and 30% of pregnant women will be colonized with GBS. Maternal colonization may account for preterm delivery, prolonged labor, premature membrane rupture, intrapartum fever, low birth weights, as well as the early-onset diseases. Treatment of the mother, pre-delivery, greatly improves the neonatal outcome and can eliminate the vertical transmission of GBS. However, diagnosis of maternal GBS colonization and subsequent treatment may not eliminate vertical transmission if the diagnosis/therapeutic program is to early in the pregnancy due to frequent recolonization of the mother. Early diagnosis does identify neonates that may be at risk for GBS infection. But there is a documented need for the rapid, sensitive and accurate diagnosis of GBS at the time of delivery. If such a diagnostic tool were available, prophylactic treatment of the mother could begin at the onset of delivery and for the infant at birth. This has been demonstrated to singificantly reduce the risk to the neonate.

GBS consists of 5 serotypes. These are designated Ia, Ib, Ic, II, and III. All 5 serotypes have been implicated in clinical infections. All 5 serotypes contain a group specific polysaccharide which is unique, in addition, they also contain antigens which uniquely identify the serotype. As the group specific polysaccharide identifies all the serotypes, this antigen has been the focus of immunological methods for the identification of GBS. The "gold standard" for GBS diagnosis remains culture identification. This process can require between 24 and 72 hours for accurate identification of GBS. High risk pregnancies frequently complete delivery long before the culture results are available.

There are a number of different immunological tests commercially available for the detection of GBS. Clinical evaluations of these methods demonstrate clinical sensitivities that range from 12% to 92.3%, with an average clinical sensitivity of 50% to 60%. Analytical sensitivities reported range from $7.6 \times 10^5$ to $2.1 \times 10^7$ cells. While these methods provide a rapid diagnosis, they do not have the required sensitivity to address the clinical need for timely identification of GBS.

For example, WO 9219969, describes an assay for GBS where the solid support is coated with a monoclonal antibody which specifically interacts with one epitope of the group B specific polysaccharide, the trirhamanose epitope. A polyclonal antibody specific to a monorhamnose epitope is conjugated to a signal generating label. The analytical sensitivity of the method is set at $3 \times 10^4$ cells. Sensitivity is only obtained through the stringent selectivity of the capture agent. The method concentrates only on the dominant epitopes of GBS. The "antigen capture agent has an affinity for specifically binding to trirhamnose epitope of GBS polysaccharide antigen" and this antigen capture agent is further characterized as "being able to interact with the trirhamnose epitope in an exclusive or at least dominant fashion such that any interaction between this capture agent and other components of group B streptococcus polysaccharide antigen is at the very least low or negligible (i.e., the interaction with the trirhamnose epitope is specific enough for the purposes of detection and/or diagnosis of GBS polysaccharide antigen or GBS infection)". The assay requires that the swab be placed in a receptacle coated with the antigen capture agent. The receptacle has a very high area/volume ratio. Antigen is extracted from the swab using an acid extraction protocol requiring 5 to 20 minutes. Buffer containing Tris and Tween is then added and the swab removed. An antigen marker agent is added and the mixture incubated for an additional 10 to 15 minutes. The receptacle is then thoroughly washed, and a substrate added for 10 to 20 minutes. The reaction is then stopped and the result read by spectrophotometry.

The method for detection of GBS described in the current invention achieves the sensitivity required in under 30 minutes. The test result is easy to interpret and is suited to bedside or delivery room use. The optical test surface of this invention provides improved sensitivity due to the unique attachment layer and works well with any group specific polyclonal or monoclonal antibody. The antibodies do not need to exhibit different epitope specificity to achieve the clinical sensitivity needed. Antibody preparations which are a combination of varying specificities and affinities for the GBS antigen work well on both sides of a sandwich format. However, antibodies with differing epitope specificities are useful in the current invention.

Chalmydia

*Chlamydia trachomatis* is an obligate intracellular organism which must be cultured in living cells, i.e., tissue culture. Chlamydia has 15 serovars and primarily causes human ocular and genital diseases such as trachoma, conjunctivitis, lymphogranuloma, venereum, nongonococcal urethritis, and proctitis. There are approximately 3–4 million cases of Chlamydia in the U.S. annually. Only very specialized laboratories can successfully culture Chlamydia but the yields are low and contamination problems are high. Storage conditions effect the viability of the organism for culture. The recommended culture protocol involves inoculating cycloheximide treated McCoy cells, a blind passage, and fluorescent staining of the inclusion bodies. Vortexing and sonication of the sample prior to inoculation increases the positive culture yield. Sampling should include cells and mucus surrounding the sampling site.

In addition to culture techniques a number of direct immunofluorescence and ELISA methods have been developed. These techniques provide inadequate sensitivity to detect patients with low levels of Chlamydia infection or for individuals that are asymptomatic. An overall sensitivity of 44% relative to culture has been reported for samples containing less than 100 IFU, inclusion forming units. Available methods demonstrate a sensitivity of 82% for samples with greater than 100 IFU.

Many gram negative bacteria also produce organism specific lipopolysaccharides (LPS) similar to the one produced by Chlamydia. Detection and identification of the organism may be made based on the immunological reactions of this antigen. Organism specific polysaccharides may also be useful. Gram negative bacteria include but are not limited to *Chlamydia psittaci, E. coli, Pseudomonas fluorescence, Azotobacter vinelandii, Aerobacter aerogenes, Neisseria gonorrhoea, Treponema pallidus, Micrococcus pyogenes*, Shigella, Hydrogenomonas species, Salmonella, *Hemophilus influenza*, Campylobacter, Heliobacter, and Legionella.

U.S. Pat. No. 4,497,899 describes an assay based on the non-specific adsorption of antigen to a bare solid support such as silica, silicone, glass, metals, or plastic beads. There is no chemical or immunological binding of the antigen to the solid support. The assay protocol involves mixing the beads with sample which has been lysed to liberate the antigen. Following adsorption of the antigen to the beads, the beads are rinsed and transferred to a new carrier. An antibody specific to the Chlamydia antigen is added and incubated for a period of time, and then the beads are rinsed. Another antibody specific to the anti-Chlamydia antibody which is conjugated to the signal generating label is then mixed with the bead and incubated, followed by a rinse step, and then incubation with the substrate.

U.S. Pat. No. 4,497,900 describes an assay for *Neisseria gonorrhoea* using a bare solid support for non-specific antigen adsorption. The solid support is a bare, untreated, uncoated support preferably of a hydrocarbon polymer, polystyrene, silica, silicone, glass, or metals.

U.S. Pat. No. 4,959,303 describes a method for the detection of gram negative bacteria. The solid support used is free of any specific binding proteins, and is essentially protein free. The solid support is a bare, hydrophobic support which may possess a positive charge. The assay protocol requires that the antigen be mixed with an anti-Chlamydia antibody which is non-specifically captured on the surface. An antibody specific to the anti-Chlamydia antibody and is conjugated to the signal generator is then added, followed by substrate, and then detection. The support maybe any bibulous, non-porous water insoluble material.

U.S. Pat. No. 5,030,561 modifies the above approaches by using an amidine modified latex particle or polystyrene as the solid support. The antigen adheres to the support non-specifically and the particles are used for separation of the solid phase from the liquid phase through filtration. The membranes used in the filtration process must be washed with surfactant and casein prior to their use in the assay. Substrate visualization occurs at the membrane.

U.S. Pat. No. 5,047,325 details a method for the detection of Chlamydial and Gonococcal antigens using a bare or coated solid support which is positively charged. Suitable solid supports include glass, cellulose, and certain polymers. The positive charge is preferably a quaternary salt which will maintain its charge over a wide pH range. The support provides an additional source of non-specific antibody capture which must be eliminated by washing the surface with a cationic surfactant. Samples must be pre-filtered to remove cell debris.

U.S. Pat. No. 5,075,220 uses a polymeric support with cationic surface groups to assist in an ionic interaction of the LPS antigen with the solid support. The support should be free of any antibody or other biological compound prior to reaction with the antigen.

The Chlamydia assay of this invention uses a solid support coated with a polymeric siloxane which creates a hydrophobic surface capable of non-specifically capturing LPS or similar antigens. This approach will work for identification of any LPS source. Surprisingly, it has been found that the best, most uniform reaction is observed when a low amount of non-specific biological material, either antibody or other protein, is coated onto the hydrophobic surface prior to antigen capture. This additional coating process may also be of use in assays which use EIA, FIA, or RIA detection techniques. In the method of this invention, the non-specific biological layer promotes uniform adhesion of the precipitating substrate system. Any system which relies on the combination of a solid support, particularly a hydrophobic support, with a precipitating substrate system could benefit from this observation.

RSV

Respiratory Syncytial Virus (RSV), a myxovirus, is associated with severe lower respiratory tract illness in infants and children. In adults, RSV usually causes a mild, afebrile, upper respiratory tract infection. In the first six months of childhood, the organism is responsible for 32 to 75% of all bronchiolitis and 3 to 39% of pneumonia. These illnesses are often life threatening. The organism has also been associated with other types of acute febrile respiratory diseases, such as bronchitis and pharyngitis. The organism may be detected in nasal/pharyngeal secretions by culturing the sample prior to any freezing or exposure to elevated temperatures. The sample is used to inoculate HeLa or Hep2 cells and requires 3 to 14 days to obtain a result. RSV outbreaks occur in late fall/early winter and late winter/early spring and last 3 to 5 months per episode.

An early viral diagnosis allows physicians to infer patient prognosis and confirms the etiology of respiratory diseases. Three types of diagnostics have been used for confirmation of viral illness. First, culture isolation followed by a confirmation protocol. Second, serological assays for the detection of host response to the viral infection, and third, direct viral antigen detection.

Culture methods for RSV involve collection of a specimen and mixing the specimen with glass beads. Tracheal secretions and bronchoalveolar lavage specimens are routinely used. The beads are used to disrupt the specimen cells by sonication or vortexing to disperse the virus into the transport media. An aliquot of this is used to inoculate the cell cultures. Confirmation tests used include complement fixation and neutralization.

Serological assays rely on host response to the virus, i.e., rely on IgG production. However, the IgG may not be produced for two or more weeks and may persist for months to years following infection which complicates diagnosis. Direct antigen detection methods are more diagnostic of active infection, but for RSV are significantly less sensitive than culture/confirmation techniques. Direct detection methods have included immunofluorescence, electron microscopy, ELISA, and culture.

HIV

The Human Immunodeficiency Virus (HIV) has several characteristic markers including gp41, gp160, gp120, p66, p24, and p18. The p24 peptide is one of 4 nucleocapsid proteins comprising the core of HIV-I and has a molecular weight of 24,000 daltons. The selective infectivity of the HIV virus is accounted for by the gp120 antigen, while gp41 is required for viral entry into the host cell. Current screening assays rely on detection of host response, i.e., antibody production, to one or more of these markers. Existing immunoassay methods do not provide sufficient sensitivity for direct antigen detection.

Currently, final confirmation of HIV infection is based on Western (immunoblot) blotting techniques. These tests are costly and technically demanding, as well as difficult to interpret. Performance of this method under field conditions is usually inferior to that of reference laboratories. Western blots are designed to detect one or more of the viral core gag proteins p17, p24, or p55; one or more of the polymerase proteins p31, p51, or p66; and one or more of the envelope proteins gp41, gp120, or gp160. The Red Cross requires three positive bands, one in each group. The CDC recommends at least 2 positive bands including p24, gp41, and gp160/120, while the FDA recommends that p24, p31, gp41, and/or gp120/160 be positive to report a positive result.

The current invention provides a suitable optical platform for the detection of host response to one or more of the HIV specific antigens. Antigens may be presented on the surface in combination or individually.

Hepatitis Virus

Clinically, the various forms of viral hepatitis are difficult to differentiate. Therefore, serological tests are required for the diagnosis of causative agent. Five separate viruses have been associated with hepatitis. They are designated A, B, C, D, and E. Originally Hepatitis C was designated non-A, non-B. Recently, a non-A, non-B like hepatitis has been postulated. Hepatitis A and E are transmitted by the fecal/oral route and cause acute infections. Hepatitis B, C, and D are transmitted by the parenteral route and cause both acute and chronic infections. HCV is responsible for most post-transfusion hepatitis. Many HBV infected individuals are asymptomatic and are infective. HBV infection has been linked with liver cirrhosis and cancer. A review of the serological diagnosis of hepatitis is presented in Postgraduate Medicine, volume 92, pp. 55–68, 1992.

Each form of hepatitis possesses (Ags) antigens unique to that form of the virus; HAV has the HAVAg; HBV has surface antigen (HBsAg), core antigen (HBcAg), and an internal component of the nucleocapsid (HBeAg); HCV has C100, 5-1-1, C22-3 (core), C33c (core), with the N-terminal of the core peptide being the major antigenic region of the core antigen; HDV has the delta antigen and will frequently test positive for HBsAg; and HEV has not been well characterized. The form of hepatitis may be determined based on antigen detection or host antibody response. Because of the sensitivity required for direct antigen detection, current diagnostic assays detect antibody response to specific antigen/s. Host response may produce IgM and/or IgG and differentiation of the antibody response may be required to establish the active state of infection. For example, IgM anti-HAV indicates an acute infection, while IgG anti-HAV indicates previous infection.

The current invention provides a useful platform detection technology for diagnosis of hepatitis. A combination of antigens can be immobilized on the test surface to detect host response to those antigens. The surface panel can detect a combination of antigens specific to one hepatitis virus, e.g., HBV, where the surface can be coated with one or more of the following: surface antigen, core antigen, or the e antigen. Or the panel can be coated with one or more antigens which discriminate between HAV, HBV, HCV, HDV, and HEV using a single sample. Such a screening test can be developed in either the visual, qualitative format or in a fully automated, instrumented format. Antibody detection can be specifically tailored for IgG, IgM, or both.

The following examples illustrate various procedures by which test devices of this invention can be optimized. They also provide examples of particularly useful combinations of each surface layer described above for use with instruments or eye-read results. Those in the art will recognize that these procedures can be used to optimize equivalent test devices to produce those useful in this invention.

EXAMPLE 1

Diffuse Surface

Silicon wafers lapped with varying particle sizes to produce varying levels of diffuse refection, were coated with silicon nitride to a thickness of 500 Å and refractive index of 2.0 to produce an AR wafer. This produces a gold interference color. The wafers were initially inspected for the amount of reflectivity observed, or for the remaining specular characteristics. These wafers were then coated with an aminosilane as described below, and then antibody coated with an anti-Strep A polyclonal antibody.

Test surfaces were chemically activated by application of N-(2-aminoethyl)-3-aminopropyltrimethoxysilane by the following procedure:

1. The AR wafers were oxygen plasma etched for five minutes in a vacuum at 0.7 Torr oxygen pressure with a plate current of 175 D.C. milliamperes and 250 RF watts.

2. The wafers were placed in a quartz rack and inserted into a vacuum desiccator with a vessel containing 5 microliters of N-(2-aminoethyl)-3-aminopropyltrimethoxysilane. The vacuum was evacuated to 0.06 Torr for 30 minutes. The temperature of the desiccator was raised to 100 degrees over the course of one hour to complete the vapor phase deposition of the aminosilane.

3. 20 micrograms/ml of a polyclonal anti-Strep A preparation in 20 mls of PBS (phosphate buffered saline), 10 mM potassium phosphate, 0.8% NaCl, at pH 7.2), and 1% by volume glutaraldehyde were combined to form the receptive material solution. The wafers were placed in a petri dish and the receptive material solution was added.

4. The wafers were incubated at room temperature (about 20° C.) in an agitation bath for 15 hours.

5. Following incubation, the wafers were rinsed with deionized water to remove the unbound antibody.

6. The surface was incubated in a stabilizing solution and incubated for one hour in an agitation bath. The stabilizing solution was made of 2 ug/ml acid hydrolyzed casein, 1% (v/v) glycerol and 2% (w/v) sucrose in PBS.

7. Following the stabilizing process, the surface was rinsed with deionized water and then dried under a stream of nitrogen.

The wafers were then reacted with samples containing varying levels of Strep Group A antigen and a latex secondary reagent, described in Examples 14 and 15, by incubation for 2 minutes at room temperature. The slides were rinsed with deionized water and dried under a stream of nitrogen. No difference was observed in the amount of silane incorporated or antibody attached.

The results are shown in Tables 1 and 2, and demonstrate that suitably non-specular surfaces allow viewing at any angle and with a higher sensitivity than a specular surface.

TABLE 1

| Lap Particle Size | Average Particle Size | Dek-tak ® Separation | Dek-tak ® RMS | Comments |
| --- | --- | --- | --- | --- |
| 10–20 micron | 15 micron | 20 micron | 2995 | Diffuse, no angle dependence, color clear at all viewing angles |
| 20–40 micron | 30 micron | N/A | N/A | Diffuse, minimal specular character, low angle dependence, color constant at most viewing angles |
| 40–60 micron | 50 micron | N/A | N/A | Less diffuse, more specular character, more viewing angle dependence, color starting to show angle dependence |
| 80–100 micron | 90 micron | 40 micron | 4779 | Slightly diffuse, very specular, strong angle dependence, color varies with viewing |

TABLE 2

Visual Interpretation of a Strep A Assay on Different Lapped Wafer Surfaces

| Wafer | Concentration of Strep Group A Antigen | | | | | | | | |
| --- | --- | --- | --- | --- | --- | --- | --- | --- | --- |
|  | 0.000 | 0.008 | 0.016 | 0.032 | 0.064 | 0.128 | 0.250 | 0.500 | 1.000 |
| 15 micron | — | Trace | + | ++ | ++ | +++ | +++ | ++++ | ++++ |
| 30 micron | — | — | Trace | + | ++ | ++ | ++ | +++ | +++ |
| 50 micron | — | — | Trace | Trace | + | ++ | ++ | ++ | +++ |
| 90 micron | — | — | — | — | — | + | + | ++ | +++ |

EXAMPLE 2

Glass Substrate

A four inch diameter sodium borosilicate glass was coated with a thin film, 10–50 Å, of aluminum (chromium can also be used) to effectively increase the reflectivity of the glass and block back surface reflections. This material was then coated with amorphous silicon by a thermal deposition process, as described above, and then with a layer of silicon nitride, approximately 500 ±3% Å in thickness.

The surface was prepared for antibody coating as described in Example 11 below. In this example, a polyclonal antibody to Streptococcus Group A (GAS) was used to coat the surface. Specifically, 100 μl samples of diluted or undiluted GAS antigen was mixed with 50 μl anti-GAS surface activator particle, and assayed as described in Example 11. A comparison of this surface to a silicon nitride coating on a silicon wafer using the GAS model assay was conducted. The results are shown in Table 3 and demonstrate that glass provides as useful a substrate as does silicon.

TABLE 3

| FOLD ANTIGEN DILUTION | GLASS SUBSTRATE | SILICON SUBSTRATE |
| --- | --- | --- |
| 0.0 | – | – |
| 1:256 | +/– | – |
| 1:128 | + | + |

TABLE 3-continued

| FOLD ANTIGEN DILUTION | GLASS SUBSTRATE | SILICON SUBSTRATE |
| --- | --- | --- |
| 1:64 | + | + |
| 1:32 | ++ | ++ |
| 1:16 | ++ | ++ |
| 1:8 | +++ | +++ |
| 1:4 | +++ | +++ |
| 1:2 | +++ | +++ |
| DIRECT | +++ | +++ |

EXAMPLE 3

Construction of an AR Test Surface

An optical substrate, for this example monocrystalline silicon, was coated with a thicker layer (for example 750 to 800 Å) of material such as silicon nitride which approximates the square root dependence required for an AR film. Thickness was then selectively removed by a chemical etching technique, described above, creating approximately 50 Å steps across the substrate. This process produces a wedge of interference colors across the surface of the substrate (see FIG. 3). The substrate was then coated with the attachment layer and receptive material. Assays were performed using negative, low positive, and intermediate positive samples.

Any combination of attachment layer, receptive material, and assay protocol may be used in this analysis. The specific example used a wedge of silicon nitride on silicon which was coated with T-structure siloxane, as described in Example 5 below. The siloxane coated AR film was coated with a polyclonal anti-Strep A antibody as described in Example 11. The assay protocol followed was as described in Example 19. Samples were placed in the center of each wedge (different thickness). After completion of this assay the entire substrate was examined for the selection of the wedge or wedges which provide: 1) the cleanest negative response—the least detectable non-specific binding, 2) the best sensitivity, and 3) the best visual contrast. Once a 50 Å range of thicknesses was selected, greater resolution can be achieved by uniformly coating a substrate to the maximum thickness selected in the first experiment (for example 550 Å), and then etching this surface in 10 Å steps. This method rapidly allows the selection of the required optical thickness which provides the best "apparent" color change in combination with the biological materials.

EXAMPLE 4

Preparation of $TiO_2$ Optical Coating

All measurements are based on the volume of material used. The organotitanates may be purchased from Dupont, of particular utility is Tyzor TPT (tetra isopropyltitanate) but tetra n-butyltitanate may be substituted. One ml of TPT was mixed with three mls of glacial acetic acid, 3 mls alcohol, 3 mls deionized water, and 10 μl of 3M's FC171 fluorosurfactant. Isopropanol, t-amyl alcohol, ethanol or acetone may be used with water for this application. Ethanol should be avoided as it leads to precipitation of the titanium.

Three to five hundred microliters of this mixture was applied to an optical substrate and a uniform film produced by a static spin coating technique. The film thickness should be 495 Å±15 Å. The film was cured to the substrate by heating it to 250° C. for two hours or microwaving at 400 watts of power for two minutes. The optical substrate used in this example was a monocrystalline silicon wafer. The acceptable temperature limits will also be dependent on the type of optical substrate used. Plastic will not tolerate the 250° C. cure, but glass will. The curing conditions selected here generate a film with a refractive index of 2.0 (±3%) which is adequate for this application.

Caution must be used to ensure that the optical substrate is clean, i.e., particle free, and that the coating solution is particle free. Particulates introduce coating defects in the film during the spin coating application process.

EXAMPLE 5

Production of Attachment Layers

The designations given here for various attachment layer materials will be used throughout.

Attachment layer materials:

1: PEI-(Trimethoxysilylpropyl) polyethyleneimine
2: PEI/DMDCS-PEI+DimethylDichlorosilane
3: Polystyrene
4: MSA—Starburst; 5th generation
5: T-Polymer-Aminoalkyl T-structure branch point polydimethyl siloxane
6: TC7A—film forming latex
7: DMDPS—Dimethyldiphenyl siloxane copolymer
8: Mercapto—Mercaptopropylmethyldimethyl-siloxane copolymer
9: BAS—N-(2-Aminoethyl-3-aminopropyl) trimethoxysilane
10: PBD—Triethoxysilyl modified polybutadiene
11: PAPDS—(methylphenyl) methyldodecylmethylaminopropyl-methyl siloxane These chemicals were used to form attachment layers as follows:

1: PEI (Petrarch; Bristol, Pa.)

A 1:500 dilution of the stock silane was made in methanol. A 300 microliter sample of this solution was placed on a 100 mm virgin test silicon wafer by micropipette, although automated aerosol or spray delivery systems are equally useful, while the wafer was spinning at 7,000 rpm on a photoresist spin-coater. Spin coating can rapidly process a large number of substrates and is readily automated. While spin coating is detailed here, it is not the intention to limit this invention to this type of attachment layer production. Alternate solution based or vacuum based (where appropriate) depositions could be easily designed by those skilled in the art. PEI coated substrates were cured at 100° C. under 0.1 mm Hg for 60 minutes. A final attachment layer of 80 Å as measured by conventional ellipsometry is generally preferred, but other thicknesses have been utilized.

2: PEI/DMDCS; DMDCS (Sigma Chemical Co., St. Louis, Mo.)

A PEI coated substrate may be further processed by treatment with DMDCS. This creates branch points along the linear PEI chain and causes the surface to perform more as a T-polymer coated surface. A 100 milliliter stock of 2% DMDCS was prepared in 1,1,1-trichloroethane (v/v). The PEI coated substrate was submerged in the solution for 60 minutes at 25° C. The substrate was removed from the DMDCS coating solution and rinsed with 95% ethanol and finally dried under a stream of nitrogen. A final attachment layer of 200 Å as measured by conventional ellipsometry is generally preferred, however other thicknesses are possible.

3: Polystyrene (Becton Dickinson, Oxnard, Calif.)

Approximately 0.05 g of a polystyrene was dissolved in 2 milliliters of toluene. A solution was applied by the spin coating technique described above. Substrates were cured for 60 minutes at 25° C. prior to utilization. A final attachment layer of 200 Å is generally preferred, however other thicknesses are possible.

4: MSA-Starburst polymers (Polysciences, Warrington, Pa.)

A 1:4 dilution of the 5th generation Starburst (0.5% solids) was prepared in methanol. A 200 microliter sample of this solution was applied to the substrate using the spin coating method at a spin rate of 3500 rpm. This attachment layer was cured for 120 minutes at 25° C. A final layer of 40 Å is generally preferred, however other thicknesses are possible.

5: T-Polymer (Petrarch, Bristol, Pa.)

A 1:300 (v/v) dilution of the T-polymer was prepared in 2-methyl-2-butanol. The attachment layer was applied to the substrate by the spin coating method and was cured for 24 hours at 140° C. prior to use. A final layer of 100–160 Å is generally preferred.

6: TC7A (Seradyn, Indianapolis, Ind.)

The 30% stock solution was diluted to a 0.5% solid in methanol. A 300 microliter sample is applied to the substrate using the spin coating technique and is cured at 37° C. for 120 minutes prior to use. A final thickness of this material is preferred to be 240 Å.

7: DMDPS (Petrarch)

A 1:100 (v/v) stock solution of the siloxane in toluene was prepared and applied utilizing the spin coating technique and curing protocol described for the T-polymer. A preferred final thickness is 200 Å.

8: Mercapto (Petrarch)

A 1:300 (v/v) stock solution of the siloxane was prepared in toluene. The coating and curing protocol were as described for PEI. A preferred final thickness is 200 Å.

9: BAS (Petrarch)

A 1:100 (v/v) solution of silane was prepared in toluene. A 200 microliter sample was used in the spin coating protocol. The wafer was cured for 2 hours under 0.1 mm Hg at 140° C. A preferred final thickness is 30 Å.

10: PBD (Petrarch)

A 27.5 microliter volume of the stock silane was mixed with 3275 microliters of toluene. The spin coating volume was 300 microliters of this mixture and wafers were cured for 60 minutes at 120° C. A preferred final thickness is 100 Å.

11: PAPDS (Petrarch)

A spin coating volume of 200 microliters of 1:100 (v/v) of siloxane in toluene was used and wafers were cured for 120 minutes at 100° C. prior to use. A preferred final thickness is 200 Å.

The above-noted concentrations, volumes, weights, spin coating speed, buffers, incubation time and conditions, and all other reagents or processes described throughout these examples are intended to describe preferred embodiments only, and are not limiting in this invention.

EXAMPLE 6

Comparison of Attachment Layer Materials for Antigens

A system was designed for the analysis of attachment layer material efficiency in attaching an antibody as receptive material to a monocrystalline silicon substrate. This procedure can be used for optimization of other systems of this invention. Achieving a dense, reactive layer of antibody has been demonstrated to be more difficult than other layers of receptive materials due to more stringent orientation requirements. An ELISA system was designed for evaluation of an attachment layer. A monoclonal anti-horseradish peroxidase (HRP) was bound to an attachment layer as the test receptive material, then varying levels of horseradish peroxidase (HRP) were placed on the surface to produce a standard curve. Microtiter wells were antibody coated under the same conditions as a control.

All surfaces were antibody coated from a solution of 0.05M PBS, pH 7.4 containing 20 µg/ml of the monoclonal anti-HRP (Sigma Chemical Co., St. Louis, Mo.) for 16 hours at 25° C. The coated substrates were submerged in the coating solution. Peroxidase (Sigma Chemical Co., St. Louis, Mo.) concentrations were allowed to react with the test surface or the microtiter wells for 30 minutes at 37° C. and then unbound peroxidase was removed by rinsing with deionized water. TMB (Kirkegaard and Perry) substrate was then added to all test surfaces and allowed to react for 2 minutes at 25° C. for color development. Fluid from each spot on the test surface was transferred to an uncoated microtiter well containing stopping reagent and the optical density at 450 nm recorded. Stopping reagent was added directly to the microtiter wells of the comparison plate and it was similarly read.

The results of this study are presented in Table 4. Surfaces were evaluated in terms of sensitivity (resolution of low concentrations relative to the negative control) and dynamic range. For control purposes each attachment layer was also coated with rabbit IgG and then evaluated in the peroxidase assay. Insignificant interaction of peroxidase with all rabbit IgG coated attachment materials was observed. The raw silicon substrate was also examined under similar conditions, and found to exhibit very little active receptive material binding to the surface. (Data is reported as optical density measured at 450 nm.)

TABLE 4

| Test Surface | PEROXIDASE CONCENTRATION (ng/ml) | | | | | | | |
|---|---|---|---|---|---|---|---|---|
| | 0.0 | 15.6 | 31.25 | 62.5 | 125.0 | 250.0 | 500.0 | 1000.0 |
| Nunc* | 0.005 | 0.634 | 0.646 | 0.863 | 0.876 | 1.252 | 1.561 | 1.413 |
| Dynatech* | 0.017 | 0.161 | 0.150 | 0.279 | 0.662 | 1.173 | 1.465 | 1.598 |
| PEI/-DMDCS | 0.007 | 0.136 | 0.264 | 0.371 | 0.428 | 0.714 | 1.118 | 1.493 |
| T-Polymer[a] | 0.030 | 0.076 | 0.107 | 0.111 | 0.276 | 0.498 | 0.730 | 0.850 |
| T-Polymer[b] | 0.015 | 0.137 | 0.328 | 0.365 | 0.473 | 0.682 | 0.946 | 0.810 |
| MSA | 0.003 | 0.037 | 0.100 | 0.166 | 0.305 | 0.373 | 0.511 | 0.428 |
| PEI[d] | 0.008 | 0.175 | 0.238 | 0.636 | 0.651 | 0.702 | 0.817 | 0.743 |
| TC7[c] | 0.016 | 0.065 | 0.109 | 0.159 | 0.179 | 0.399 | 0.324 | 0.215 |
| MERCAPTO | 0.000 | 0.259 | 0.514 | 0.658 | 0.881 | 0.957 | 1.143 | 1.558 |
| DMDPS | 0.015 | 0.039 | 0.036 | 0.166 | 0.100 | 0.152 | 0.259 | 0.442 |
| Polystyrene | 0.000 | 0.248 | 0.343 | 0.444 | 0.631 | 0.756 | 0.795 | 0.878 |
| BAS[d] | 0.002 | 0.008 | 0.012 | 0.026 | 0.055 | 0.100 | 0.120 | 0.210 |
| PBD | 0.011 | 0.013 | 0.047 | 0.041 | 0.072 | 0.108 | 0.124 | 0.143 |
| PAPDS | 0.004 | 0.314 | 0.559 | 0.515 | 0.790 | 0.822 | 1.259 | 1.186 |

[a]T-Polymer was applied to the substrate to a final thickness of 240Å.
[b]T-Polymer was applied to the substrate to a final thickness of 55Å.
[c]TC7A was applied to a final thickness of 246Å.
*Microtiter wells from these suppliers were used for comparison to the optical test surfaces.

This study clearly demonstrates the utility of a siloxane as an attachment layer on a thin film substrate relative to treating such substrates with PEI or BAS. There is also variability in the utility of the individual siloxanes, suggesting the functional groups of the siloxane may influence the reactivity of the receptive material. The molecular self-assembling polymers also show enhanced performance as an attachment layer relative to BAS, but are not as useful as the siloxane materials. While the TC7A surface activator performed poorly in this assay system it has marked utility in subsequent examples.

EXAMPLE 7

Comparison of Attachment Layer Materials for Antibodies

For this analysis, varying attachment layers were coated by immersion in a solution of 20 µg/ml of rabbit IgG (Sigma Chemical Co., St. Louis, Mo.) in 0.05M PBS, pH 7.4 for 16 hours at 25° C. Different levels of HRP labeled goat anti-(whole molecule) rabbit IgG antibody (Sigma Chemical Co., St. Louis, Mo.) were allowed to incubate with the test surface for 15 minutes at 37° C. Unbound material was removed by rinsing with deionized water. The TMB substrate solution was applied to the surface and allowed to react for 2 minutes at 25° C., and then the solution transferred to an uncoated microtiter well, containing stopping solution. (The optical density of these samples was measured at 450 nm.) The results are shown in Table 5.

TABLE 5

Goat Anti-Rabbit-HRP Concentration (ng/ml)

| Test Surface | 0.0 | 15.6 | 31.25 | 62.5 | 125.0 | 250.0 | 500.0 | 1000.0 |
|---|---|---|---|---|---|---|---|---|
| PEI-DMDCS | 0.010 | 0.035 | 0.085 | 0.123 | 0.290 | 0.289 | 0.469 | 0.572 |
| T-Polymer[a] | 0.015 | 0.060 | 0.061 | 0.136 | 0.424 | 0.437 | 0.585 | 0.715 |
| MSA | 0.073 | 0.019 | 0.033 | 0.085 | 0.153 | 0.227 | 0.616 | 0.799 |
| Raw Silicon[b] | 0.000 | 0.000 | 0.001 | 0.012 | 0.026 | 0.037 | 0.128 | 0.280 |

[a]T-Polymer was applied to the substrate to a final thickness of 53Å.
[b]Raw silicon is substrate material alone.

In this study the various test surfaces were used to demonstrate the utility of the system in the detection of an antibody capture. In this case the siloxane attachment layer and the molecular self-assembling attachment layer performed equally well. The substrate without the addition of an attachment layer demonstrated very little available or reactive receptive material, demonstrating the need for an attachment layer.

EXAMPLE 8

Competitive Assay Format

DNP is a small molecule, not atypical of the molecular range exhibited by therapeutic drugs, drugs of abuse, pesticide residues, or organic residues. It is often desirable to assay small molecules such as these using a competitive assay format.

This example describes the method and results of an assay quantitating the concentration of DNP in the sample. The surface was coated with either the hapten or a carrier which was conjugated with the hapten. The hapten may be directly immobilized to the surface if appropriate chemistries are available, or passively attached to the surface. The same options apply to the hapten/carrier conjugate.

Test samples were mixed with a material which will react not only with the free hapten in the test sample, but also with the immobilized hapten. One of the most commonly used reactive materials is an antibody specific to the hapten. Any highly specific binding reagent could be substituted for the antibody. The extent of capture of this reagent is inversely proportional to the concentration of free hapten in the original test sample. The test may be designed to produce quantitative or qualitative results.

Materials and reagents were prepared as follows:

1. Monocrystalline silicon wafers, 4 inches in diameter, n=4.02, virgin test quality, polished on one side, 1-0-0 crystal orientation, were coated with silicon monoxide to a final thickness of 550 (±10) Å and a refractive index of 2.0 (±0.05). The thin film interference color produced by this material is gold. The silicon monoxide was applied to the wafers by a standard chemical vapor deposition technique.

2. The wafers were activated with the bis-aminosilane vapor coating process described in Example 1.

3. These amine derivatized surfaces were placed in 30 mls of solution containing phosphate buffered saline (PBS), pH=7.2 and 5 mg/ml DNP conjugated to human serum albumin (HSA) (DNP-HSA) in a Falcon 100 mm Tissue Culture Dish. Wafers were coated at 37° C. (±2° C.), 98% humidity until 40 Å of DNP-HSA was deposited on the surface (approximately 30 minutes). A Gaertner Ellipsometer was used for all thickness determinations. The wafers were removed from the coating solution, rinsed with deionized water, and dried under a stream of nitrogen.

4. Goat anti-DNP was mixed in PBS to a concentration of 1.2 mg/ml. DNP was dissolved into water. Antibody and DNP were mixed 1:1. A 20 µl sample of the mixture was applied to the coated surface and incubated for 10 minutes at room temperature. Unbound materials were rinsed from the surface with deionized water and the surface dried under a stream of nitrogen. The slide was visually examined and, in addition, the change in mass at the surface measured by a change in light intensity using a modified Sagax Comparison Ellipsometer, see FIG. 15. Reading protocol is given in Example 21. Visual examination gives a semi-quantitative estimation of the concentration when a sample is compared to a standard curve.

The results are shown in Table 6.

TABLE 6

| Concentration of DNP Added in ng/ml | Relative Ellipsometric Intensity | Visual |
|---|---|---|
| 0.0 | 53.2 | ++ |
| 0.031 | 40.4 | + |
| 0.062 | 34.0 | + |
| 0.125 | 27.4 | +/− |
| 0.500 | 26.6 | +/− |
| 1.000 | 23.3 | +/− |
| 100.0 | 15.0 | − |

EXAMPLE 9

Small Molecule Detection

A 4-inch monocrystalline silicon wafer with an index of refraction of 4.02 at a specified wavelength was coated with silicon oxynitride. The refractive index of this coating of silicon oxynitride was 1.98 with a thickness of approximately 540 Å.

The wafer was then chemically activated by application of approximately 50 ±2 Å of (N-trimethoxysilylpropyl) polyethyleneimine (Petrach Systems, Bristol, Pa.) using standard wafer spin coating techniques designed for application of photoresist. The wafer was cured in an oven at 140° C. for a period of 2 ±0.1 hours.

A fresh 1% solution of a small analyte, trinitrobenzene sulfonic acid (TNBS), was prepared in deionized water. A 25 µl drop of deionized water (control) and of the TNBS solution was placed on the surface of the amine coated wafer. The drops were allowed to react with the surface for five seconds. The surface was rinsed with water and dried with a stream of pressurized air. Upon visual inspection under polychromatic light the area contacted with the TNBS is a red-purple color.

The change in thickness on the surface caused by TNBS binding is approximately 20 Å. This was sufficient to produce a visually discernable color change in the area where the TNBS bound.

EXAMPLE 10

Enzyme Detection

A 4-inch monocrystalline silicon wafer was coated with an AR film of 525 ±3% Å silicon nitride (refractive index 1.97 ±0.05).

The deep gold colored wafer was coated with approximately 100 ±2 Å of aminoalkyl-(t-structured)-polysiloxane (Petrarch Systems, Bristol, Pa.). The gold colored wafer was cured for two hours at 140° C. The wafer takes on a very slight purple tint.

The siloxane coated wafer was placed in a phosphate buffer containing acid soluble collagen. The collagen solution was prepared in the following manner. Acid soluble collagen type I from calf skin (Sigma Chemical, St. Louis, Mo.) was dissolved in 1 molar acetic acid adjusted to pH 4 at a concentration of 5 mg/ml. Then, a 0.1 molar phosphate buffered saline, pH 6.8, containing 20 ug/ml of the acid dissolved collagen was prepared. This solution was used to coat the wafer for a period of two hours at room temperature. Thirty mls of solution were placed in a Falcon Tissue Culture Dish and the wafer submerged in the solution. The wafer was rinsed with water and dried with a stream of pressurized air. The wafer had a dark purple/blue color. Solutions of collagenase enzyme (Boehringer-Mannheim) in a 0.1 molar Tris-Hcl buffer, pH 7.2, containing 50 mM calcium ion were prepared with 0 to 1 units of activity per ml of solution to evaluate the collagen coated wafer. One unit is equal to the amount of enzyme that hydrolyses 1 µmole of FALGPA per minute at 25° C. In this system the enzyme will degrade the collagen on the wafer surface and cause a thickness decrease. The thickness decrease is opposite of the other examples described in this invention, which involve color change due to thickness increases.

A 25 µl drop of collagenase enzyme at a concentration of 0.5 units/ml was allowed to react with the collagen coated wafer for five minutes. The wafer was washed with deionized water and dried with a pressurized air stream. Upon visual inspection areas contacted with the enzyme had a gold appearance while the background remained dark red to purple. The results are shown in Table 7.

TABLE 7

| Collagenase Concentration | Visual | Color |
|---|---|---|
| 0.0 µ/ml | – | purple/blue |
| 0.1 µ/ml | + | purple |
| 0.2 µ/ml | + | purple |
| 0.5 µ/ml | ++ | pale purple |
| 0.8 µ/ml | ++ | pale purple |
| 1 µ/ml | +++ | gold |

EXAMPLE 11

Attachment Layer Evaluation

A silicon substrate was prepared by processing diamond sawed wafers from a monocrystalline silicon ingot in a series of steps known to those skilled in the art as lapping. Sawed wafers were lapped with an abrasive material, etched to a more uniform surface profile with acid or caustic solutions, then further lapped to a progressively finer level of surface roughness. For this application, an abrasive preparation of 12–21 micron aluminum oxide particles with a mean size of 15 microns was used to produce a diffusely reflective substrate. For this particular study, the substrate prepared as described above was coated with silicon nitride to a final thickness of 550 Å. While this is the combination of materials described, any AR material at varying thicknesses may be used within this invention. The test surface was then treated with a number of the attachment layer materials as described in Example 5.

These test surfaces were coated in solution with 20 µg/ml of a rabbit anti-Streptococcus Group A (Strep A) antibody in 0.1M HEPES, pH 6.0 for 60 minutes at 25° C. The test surfaces were reacted by placing a 10 microliter spot of a control solution either free of or containing Strep A antigen and a latex mass enhancing reagent (see, Example 14) and incubating for 2 minutes at room temperature. Test surfaces were then rinsed with deionized water and dried under a stream of nitrogen.

The negative control was prepared by mixing 1 part 2M $NaNO_2$ with 1 part 2M acetic acid and neutralizing with 0.66N NaOH. The positive control, a commercially available buffer-based preparation of extracted antigen from cultured Strep A cells was diluted in the extraction media prior to use. Samples were mixed 1:2 with a secondary latex reagent prior to application to the test surface. Results in Table 8 are reported as the highest dilution of positive control capable of being visualized above a negative control.

TABLE 8

| Test Surface | Highest Detectable Dilution |
|---|---|
| T-Polymer | 1:256 |
| TC7A | 1:8 |
| BAS | No visual response |
| PEI | No visual response |
| PEI/DMDCS | 1:16 |
| DPhDMS | No visual response |
| MSA | 1:64 |

This study was designed to demonstrate the utility of the attachment layers in an antigen capture assay where the result is a visual signal on a diffusely reflecting substrate. In this case BAS and PEI, demonstrate little functional receptive material binding. The various siloxanes demonstrate varying ability to adhere the receptive material. The best assay performance is obtained with the T-polymer siloxane. Both the molecular self-assembling attachment layer and the surface activator, TC7A, show some utility in this assay system.

EXAMPLE 12

Instrumented Assay

The monocrystalline silicon substrate used in this example is a polished wafer surface. The attachment layers were applied as in Example 5 and antibody was applied as in Example 11. The assay was conducted as described in Example 11. The positive control used contained a dilution of the Strep Group A antigen. Once dried, the reacted test surfaces were examined with the Sagax Comparison Ellipsometer and the photometric analysis of the reflected light intensity was recorded in terms of a millivolt reading (see, Table 9).

TABLE 9

| Test Surface | Negative Control (mV) | Positive Control (MV) |
|---|---|---|
| PEI | 36.0 | 133.0 |
| PBD | 21.2 | 37.7 |
| TC7A | 0.0 | 56.0 |
| T-Polymer | 15.5 | 286.4 |
| MSA | 0.0 | 136.0 |

All attachment materials tested are useful in this assay, with PEI, MSA, and T-polymer providing optimum results.

EXAMPLE 13

Collagenase Activity

A TC7A test surface was prepared as in Example 5, the monocrystalline silicon wafer was coated directly. The test surface was submerged in a solution of 0.1M Tris-HCl, pH 9.0, containing 4.9 ug/ml of human collagen Type 1 (Sigma Chemical Co., St. Louis, Mo.). The test surface was coated for 60 minutes at 25° C. Test surfaces were rinsed with deionized water and dried under a stream of nitrogen prior to use. A 143 Å layer of immobilized collagen was produced. Varying dilutions of collagenase (Boehringer-Mannheim, Indianapolis, Ind.) were prepared in a buffer containing 0.005M $CaCl_2$ and 0.1M Tris-HCl, pH 7.6. Five microliter spots of the varying concentrations of collagenase were applied to the test surface and incubated for 5 minutes at room temperature.

Reacted surfaces were rinsed with deionized water and dried under a stream of nitrogen. Reacted surfaces were examined with the Sagax Comparison Ellipsometer and reflected light intensity recorded. In this example the receptive material layer is degraded by the collagenase and holes are produced in the receptive material to give a progressively more negative signal as a function of increasing activity or concentration of collagenase. Collagenase activity is reported in units $\times 10^3$/ml. Activity was measured as light intensity in millivolts (see, Table 10).

TABLE 10

| Collagenase | Run #1 | Run #2 | Run #3 | Average | S.D. | % CV |
|---|---|---|---|---|---|---|
| 0.0 | −15 | −1 | 2 | −4.7 | 9.0 | 200.0 |
| 100.0 | 60 | 55 | 68 | 61.0 | 9.6 | 10.8 |
| 200.0 | 125 | 93 | 108 | 108.7 | 16.0 | 14.7 |
| 300.0 | 181 | 118 | 188 | 162.3 | 38.6 | 23.4 |
| 500.0 | 271 | 228 | 228 | 240.0 | 27.1 | 11.3 |

This study was designed to demonstrate the production of a test surface for the detection of an enzyme activity. While the demonstrated activity is degradative in this case, the production of a system to measure enzyme activity in terms of a synthetic activity can also be envisioned. In this case, the TC7A attachment layer demonstrated nearly a 3 fold increase in acceptance of receptive material relative to the T-polymer siloxane (results not shown).

EXAMPLE 14

Mass Enhancement

This example demonstrates use of mass-labelled antibody and selection of an appropriate mass-providing reagent. Such selection can be used for determination of optimum mass labels for other systems of this invention.

Surface Activator particles were purchased from Bangs Laboratories, Carmel, Ind.; Amide Particles: Lot Numbers L910108A (SA7-015/758) or L901015J (B7-015FF/181); or Carboxylate Particles: Lot Number L9004108 (SA1-015/787). TC3, TC3X, TC7, and TC7X are similar film-forming particles which were purchased from Seradyn, Inc, Indianapolis, Ind. All of the TC designated preparations were carboxylic acid containing styrene-butadiene copolymers. Of these preparations only the TC7 particles were extensively examined. The TC3 preparations produce a very opalescent film and were not used. Seradyn particles examined were TC-7A Product Number CML, Lot Number 1K30; TC-7X Lot Number 1M92, TC-7 Lot Number 1V18 (F040690), TC-3X Lot Number 1R35, and TC-3 Lot Number 1J44. The surface activator preparations offer more flexibility in the chemistries of immobilization as both carboxylate and amide particles are available. The amide particles are readily converted to the hydrazide particle as described in U.S. Pat. No. 4,421,896.

In this study, monocrystalline silicon, virgin test wafers were used directly. These wafers were coated with a T-polymer siloxane (Petrarch Systems, Bristol, Pa., Catalog Number PS401, Lot Number) by application of 300 microliters of 1:300 (v/v) dilution in 2-methyl-2-butanol of the stock siloxane using a spin coating device. The T-polymer was cured to the surface of the wafer by a heat treatment for 120 minutes at 120° C. The activated substrates were placed in a solution containing 20 micrograms/ml of a rabbit polyclonal antibody to Streptococcus Group A in 0.1M HEPES buffer, pH 6.0. Wafers were submerged in the antibody solution for 60 minutes at 25° C., removed, rinsed with deionized water, and dried under a stream of nitrogen. A thickness or optical density change is directly observed by examining a reacted wafer with the Sagax Comparison Ellipsometer.

Table 11 summarizes the results obtained with variously coated film-forming particles. Table 11 indicates the antibody concentration, particle concentration, and the addition of any blocking materials if necessary. The antibody used for coating of the film-forming particles was the same as that used as the receptive material on the ellipsometric wafer. Antibody was coated to the surface of the particle by incubation of the mixtures at 25° C. for 16 hours. TC7 preparations were examined as dilutions of the stock solutions, dialyzed against water and treated with a mixed bed resin prior to reaction with antibody.

TABLE 11

| Amplifier | % Solid | Antibody Concentration | A:S* Ratio | Blocker | Values Neg | Values Pos |
|---|---|---|---|---|---|---|
| TC7 | 3 | 150 | 1:1 | — | 45 | 60 |
| TC7 (dialyzed) | 3 | 115 | 1:1 | — | 45 | 45 |
| TC7 | 3 | 7.7 | 1:1 | — | 98 | 110 |
| TC7 (Ion Exchange) | 3 | 115 | 1:1 | — | 43 | 50 |
| TC7 | 3 | 150 | 1:1 | 0.005% DS | 63 | 60 |
| SA:COOH | 3 | 150 | 1:1 | — | 145 | 181 |
| SA:COOH | 3 | 150 | 1:1 | — | 143 | 180 |
| SA:COOH | 1 | 150 | 1:1 | — | 74 | 80 |
| SA:COOH | 3 | 150 | 1:1 | Casein 1.5 15 µg/ml | 50 | 50 |
| SA:COOH | 3 | 7.7 | 1:1 | — | 132 | 150 |
| SA:COOH | 1 | 7.7 | 1:1 | — | 87 | 97 |
| SA:COOH | 3 | 150 | 2:1 | — | 122 | 147 |
| SA:COOH | 3 | 150 | 1:4 | — | 42 | 51 |

TABLE 11-continued

| Amplifier | % Solid | Antibody Concentration | A:S* Ratio | Blocker | Values Neg | Pos |
|---|---|---|---|---|---|---|
| SA:COOH | 2 | 150 | 1:1 | — | 47 | 58 |
| SA:COOH | 2 | 150 | 1:4 | — | 55 | 61 |
| SA:COOH | 2 | 150 | 1:2 | — | 34 | 68 |
| SA:COOH/H$_2$O | 7 | 150 | 1:1 | — | 56 | 60 |
| SA:COOH/H$_2$O | 7 | 200 | 1:1 | — | 56 | 63 |
| SA:COOH/EDC/H$_2$O | 7 | 150 | 1:1 | — | 38 | 42 |
| SA:COOH/EDC/H$_2$O | 7 | 200 | 1:4 | — | 48 | 51 |
| SA:COOH-Surfactant | 1 | 150 | 1:1 | — | 122 | 82 |
| SA:COOH-Surfactant | 1 | 150 | 1:10 | — | 85 | 90 |
| SA:COOH-Surfactant | 20 | 370 | 1:1 | — | 283 | 150 |
| SA:COOH-Surfactant | 20 | 370 | 1:4 | — | 280 | 231 |
| SA:COOH-Surfactant | 20 | 370 | 1:1 | 1.1 1% BSA | 213 | 133 |
| SA:COOH-Surfactant | 5 | 150 | 1:1 | — | 117 | 91 |
| SA:N=N/Glut H$_2$O | 4 | 150 | 1:1 | — | 55 | 101 |
| SA:N=NH | 10 | 150 | 1:4 | — | 281 | 135 |
| SA:N=NH | 10 | 150 | 1:10 | — | 242 | 111 |
| SA:N=NH Bicine | 3 | 150 | 1:1 | — | 19 | 25 |
| SA:N=NH H$_2$O | 4 | 150 | 1:2 | — | 41 | 63 |
| SA:N=NH H$_2$O | 10 | 150 | 1:1 | — | 125 | 217 |
| SA:CONH$_2$ | 3 | 150 | 1:4 | — | 66 | 55 |
| SA:CONH$_2$ | 10 | 150 | 1:4 | — | 66 | 63 |
| SA:N=NH$^a$ | 3 | 300 | 1:2 | — | 0 | 613 |
| SA:CONH$_2^a$ | 3 | 300 | 1:2 | — | 0 | 320 |

*Amplifier to Sample Ratio.
$^a$The final concentration of hydrazide in this particle preparation was 3 M and antibody was coated to the particle in 50 mM MES, pH = 6.0 and at 56° C. for 30 minutes.

Covalent attachment of the antibody was examined with the carboxylate particles by the addition of a 1% final concentration (w/v) of a carbodiimide (1-cyclohexyl-3-(2-morpholino-ethylcarbodiimide metho-p-toluenesulfonate; Aldrich Chemical, Co., Milwaukee, Wis., Catalog Number C10, 640-2, Lot Number 09915PW). The carbodiimide was added prior to the addition of the antibody. Hydrazide treated amide particles may be treated with a final concentration of 0.05% glutaraldehyde immediately before the addition of antibody to provide covalent attachment of the antibody onto the surface of the particle. Particles were coated with antibody in a 0.01M phosphate buffered saline at pH 7.2 unless otherwise denoted.

The Strep A antigen preparation used for the production of the positive control was commercially available. This antigen was diluted into a mixture of one part 2M NaNO$_2$, one part 2M Acetic Acid, and one part 0.66N NaOH to a 1:600 dilution level. The same preparation minus the antigen was used as the negative control. The amplifying reagent was mixed in varying ratios, as designated in Table 11, with the positive and negative controls and five microliters were applied to the surface of the antibody coated wafer. The samples were incubated for 2 minutes at 25° C., rinsed, and then dried under a stream of nitrogen. Reacted wafers were examined with the modified Sagax Ellipsometer and the thickness was recorded as a change in intensity, measured in millivolts.

These data demonstrate that an extremely high particle density in the amplifying reagent introduces a non-specific association of that reagent with the test surface. Addition of ancillary proteins or surfactant do not improve the performance of the antibody coated particles. The TC-7 particles being slightly more rigid than the Surface Activators do not perform as well for this particular application, however, in comparison with some other latex preparations the TC-7 particles demonstrate significant reactivity. Increased temperature appears to improve the level of antibody incorporation into the particle and thus reduces the level of free antibody. While free antibody was not removed from these particles, it may be advantageous to remove unassociated antibody by a technique such as ultra-filtration. The hydrazide derivatized amide particles appear to provide the best overall reactivity although the amide particles also perform well. The surface activator carboxylate particles do not perform as well as the amide particles.

EXAMPLE 15

Latex

In this study the amplifying film-forming particles were prepared as in Example 14, and the assay was conducted as described there. The substrate employed was a monocrystalline silicon wafer which was lapped with 12–20 micron aluminum oxide particles, mean particle size 15 microns, to create a rough textured surface using a process well known to those skilled in the semi-conductor industry. This substrate was coated with a thin film of silicon nitride. A silicon nitride film of 350 to 550 Å is standard for this application, however, any film thickness can be utilized. The T-polymer treatment of the optical slide was as described in Examples 5 and 14.

The results are shown in Table 12. The visual results differ from those observations made in the ellipsometric system. A very high particle density provides a clean negative result, but does not produce a strong positive visual signal. A higher level of antibody incorporated into the particle produces a stronger signal than does a lower level of antibody, as observed with the instrumented assay. This study suggests that insufficient antibody coverage of the particle allows non-specific association of the latex particle with the test surface. Once optimized, however, the positive and negative results are readily detectable and distinguishable.

TABLE 12

| Amplifier | % Solid | Antibody Concentration | A:S* Ratio | Visual Response Neg | Visual Response Pos |
|---|---|---|---|---|---|
| SA:N=NH H$_2$O | 10 | 150 | 1:1 | − | + |
| SA:N=NH H$_2$O | 10 | 150 | 1:1 | − | + |
| SA:N=NH H$_2$O | 10 | 150 | 1:2 | − | + |
| SA:N=NH H$_2$O | 10 | 150 | 1:3 | − | + |
| SA:N=NH H$_2$O | 10 | 150 | 1:4 | − | ++ |
| SA:N=NH H$_2$O | 10 | 150 | 1:5 | − | +/− |
| SA:N=NH H$_2$O | 3 | 150 | 1:1 | +/− | ++ |
| SA:N=NH H$_2$O | 3 | 150 | 1:5 | +/− | + |
| SA:N=NH$^a$ | 3 | 300 | 1:2 | − | +++ |
| SA:CONH$_2^a$ | 3 | 300 | 1:2 | − | ++ |

*Amplifier to Sample Ratio.
$^a$Final hydrazide concentration is 3 M and antibody is added to the particles in 50 mM MES, pH = 6.0 at 50° C. for 30 minutes. A 2.5 M MOPS was used as the neutralizer in these experiments to provide a final pH of 8.0.

EXAMPLE 16

Enzyme Amplification

Horseradish peroxidase (Sigma grade VI) was chemically coupled to immunoglobulins purified by caprylic acid precipitation from pooled high titer sera from rabbits previously injected with suspensions of cells from cultures of *Neisseria meningitidis* A, C, Y, W$_{135}$. The coupling was done using the reagent S-acetyl thioacetic acid N-hydroxysuccinimide ester and methods described in Analytical Biochemistry 132 (1983) 68–73. The resultant conjugate contained peroxidase (104 μM) and immunoglobulin (35 μM) in a buffer of MOPS, 50 mM, pH 7.0. The peroxidase-immunoglobulin conjugate was diluted in MOPS buffer together with casein (5 mg/ml) and mixed with an equal volume of a dilution of a cell-free filtrate from a culture of *Neisseria meningitidis* organisms.

The mixture (25 μl) was pipetted to the surface of a silicon wafer coated with layers of silicon nitride, t-polymer siloxane, and purified immunoglobulin from the same rabbit antibody preparation to *Neisseria meningitidis*. Antibody was coated to the T-polymer/silicon wafer from a solution containing 10 μg/ml of antibody in 50 mM MOPS, pH 7.0. The wafer remained in the antibody for 1 hour at ambient temperature, was rinsed with deionized water, and dried under a stream of nitrogen. The antibody coated substrate was further treated by incubating the coated substrate in 0.5 mg/ml hydrolyzed casein in 50 mM MOPS pH=7.0 for 1 hour at ambient temperature followed by rinsing and drying.

Sample was mixed 1 part with 1 part of conjugate. Ten microliters was applied to the test surface. After 2 minutes the sample was washed off with water and the wafer was dried with a stream of nitrogen or blotted with a filter device. TMBlue precipitating substrate (TMBlue is a commercially available product, trademarked by Transgenic Sciences, Inc. and disclosed in U.S. Pat. No. 5,013,646) was applied to the same area of the wafer and allowed to stand for 5 minutes. The wafer was washed and dried. A purple spot was visible where the reaction had occurred. This resulting precipitate was then read by eye and ellipsometer to confirm the presence of *N. meningitidis*. A 1:20,000 dilution of the antigen is clearly resolved from the negative by eye (see, Table 13).

TABLE 13

| *N. Meningitidis* Results | | |
|---|---|---|
| Fold Dilution* | Visual Score | Ellipsometric mVolts |
| 0 | – | 64.2 |
| 1:10,000 | + | 152.0 |
| 1:5,000 | +++ | 238.5 |
| 1:2,500 | +++ | 395.7 |
| 1:1,000 | ++++ | 635.0 |

*Dilution of the stock antigen preparation into 50 mM MOPS.

A test kit can be formed based on the above assay. This kit contains all the components necessary to perform up to 50 optical immunoassay rapid tests. The kit features a solid support test station which is designed to facilitate the proper washing and drying steps required. A slide, which may include from one to five (or more) unreacted test surfaces specific for the conjugated analyte of interest, is placed on the test station. Upon completion of the first reaction, the slide is tilted forward away from the operator. The test surface(s) is vigorously rinsed with wash solution which drains from the tilted surface into the reservoir below. (The reservoir contains a solid absorbent block of cellulose acetate treated with a biocide.) The slide is then returned to a level position, and a piece of absorbent paper is placed directly onto the test surface. Several seconds contact time is allowed for full wicking. The absorbent papers are provided as pads of individual tear-off sheets conveniently located on the front of the test kit, but the wash/dry process can be effected by alternate means, such as capillary action. In addition, a solution of an enzyme-labeled substance, an enzyme-labeled antibody which is specific to an analyte of interest (such as an antigen), is provided, suitably buffered and diluted. Finally, precipitating means, such as a container of commercially available TMBlue liquid, is provided in a convenient volume so that one to three drops or more can be applied dropwise to cause the enzymatically produced mass change to precipitate before washing. The second incubation is started by adding substrate to the surface and the wash/dry process is repeated to complete the test.

Two different types of silicon wafers were used; one a gold colored silicon nitride-coated wafer and the other was a silver-colored silicon wafer without a nitride coating. One possibility is that the visual color which is observed with the peroxidase/precipitating substrate system on the silicon nitride is strictly due to the absorbance of the dye precipitated on the surface. If this is the case and the precipitated dye is not behaving as a thin film, then the silver-colored silicon wafer will produce a visual signal which is the deep blue of the TMBlue only.

T-polymer coated wafers were treated with antibodies for five separate tests; *N. meningitidis* A, C, Y, $W_{135}$; *N. meningitidis B; Streptococcus B; H. influenza B*; and *Streptococcus pneumoniae*. The first reagent produced for each test was wafers, gold and silver, coated with the attachment layer (T-polymeric siloxane) as previously described. All five antibodies were coated to these types of wafers at a 10 μg/ml concentration of antibody in 50 mM MOPS, pH 7.0 by immersing wafers in the appropriate solution for one hour at ambient temperature. Wafers were rinsed, dried, and blocked as described in Example 1.

The second reagent required utilized the same five antibody preparations for the production of antibody-horseradish peroxidase conjugates using the method described above. The stock conjugate preparations are used to produce working conjugate by dilution in 50 mM MOPS, pH 7.0, containing 5 mg/ml casein, to a final conjugate ratio of 1:100. One part of the working conjugate solution is mixed with one part of a standard antigen preparation, and a 20 µl sample applied to the appropriate antibody coated wafers.

A rapid protocol was employed using a 2 minute incubation followed by a wash, dry then a 5 minute substrate incubation to permit the build-up of product on the wafer film formation is responsible for the generation of the observed color effect.

Table 14 represents the results obtained from a comparison of the mass enhanced assay to the latex agglutination assays manufactured by Wellcome Diagnostics for a whole range of bacterial antigen assays.

TABLE 14

| Sensitivity Comparison of OIA with Latex Agglutination | | | | |
|---|---|---|---|---|
| Organism | Source of Antigen | Latex 1 + Reaction[a] | OIA[b] | OIA/Latex* |
| N. meningitidis A,C,Y,$W_{135}$ | Cell supernate | 4K | 20K | 5 |
| N. meningitidis B | Kit positive diluted in Cerebral Spinal Fluid | 8 | 32 | 4 |
|  | Kit positive diluted in buffer | 20 | 160 | 8 |
|  | Cell supernate | 25K | 200K | 8 |
| H. influenza B | Kit positive | 10 | 80 | 8 |
| Streptococcus B | Kit positive | 10 | 50 | 5 |
|  | Pronase extract of cell suspension | 10K | 40K | 4 |
| S. pneumoniae | Kit positive | 100 | Neg. | — |
|  | Type 4 polysaccharide | 200 | 400 | 2 |
|  | Type 9 polysaccharide | 50 | 50 | 1 |
|  | Type 12 polysaccharide | 50 | 10 | 0.2 |
| Streptococcus A | Positive Antigen | 80 | 1600 | 20 |

[a]Latex Agglutination Assay; commercially available.
[b]Mass Enhance Catalytic
*Represents relative increase in sensitivity achieved with OIA compared to latex agglutination.
NOTES:
1) For OIA, the dilution is the last dilution giving a visibly positive result.
2) Cell supernates noted here are the supernatants removed after overnight +4° C. standing of a heavy cell suspension made in 0.5% formalin in saline. They have a high content of the polysaccharide, hence require considerable dilution.
3) Latex tests were done with commercially available products which had not expired.

surface. Following a wash and blot dry, the sample was read with both the naked eye and an ellipsometer. Purple colored spots, strikingly visible, developed on the gold, silicon nitride-coated wafer, and grey spots were seen using the silver-colored silicon wafer without nitride coating. On the silicon nitride coated surface a very strong positive produced a white interference color. The thickness increase could be readily measured using the ellipsometer. The visible color produced, in all cases, on the silver wafers, indicate that the precipitated product behaves as a true thin film and produces an interference effect even in the absence of an AR coating. The color developed is not dependent on the dye's absorbance characteristics.

Further evidence that the chromogen does not contribute to the generation of the observed visual response was gained with the following experiment. Treatment of the TMB/$H_2O_2$ product with a stopping reagent, $H_2SO_4$, produces a yellow precipitate. If the visual response observed with the optical supports under investigation here is solely due to the chromogen, then the treatment of the surface precipitate with stopping reagent should yield a yellow-colored spot. Treatment of the immobilized surface precipitate with sulfuric acid does not modify the strong purple or blue spot produced on the silicon nitride coated wafer. Therefore, the resultant signal is entirely dependent on the formation of a thin film. Additional verification was obtained by using a strip of adhesive to remove the precipitate from the surface of the silicon nitride. The precipitate removed with the adhesive was a pale grey/blue with no red component. The observed interference effect exhibits a bright purple/blue color with a strong red component. This re-enforces the idea that thin The results shown in Table 15a and 15b are a comparison of the catalytic mass enhanced method and an Enzyme-Linked Immunoadsorbant Assay (ELISA). The data demonstrate an enhanced performance of the enzyme amplified assay for Meningitidis A, C, Y, $W_{135}$ relative to the ELISA, using TMB as a substrate. Production of the ELISA test surface and the optical test surface are described below.

There are two major differences between these techniques. First, the method of this invention utilizes a polished silicon wafer for solid phase adsorption of the antibody while ELISA utilizes a clear polystyrene microtiter plate. Second, and more important, the substrates used to develop the reaction for this catalytic method produce an insoluble product that deposits on the surface of the polished silicon wafer, while the substrate for ELISA produces a colored solution in the wells of the microtiter plate. It is because of this important difference that the results obtained with this catalytic method are more sensitive. The ELISA depends on a visible color to be produced from the chromogen, while the device of this invention depends only on a thin layer of chromogen to be deposited on the device.

Specifically, one surface is a polished silicon wafer (OIA) and the other surface, a clear polystyrene, microtiter plate (ELISA). Both surfaces received a 10 µg/ml antibody solution for 1 hour at room temperature, a deionized water rinse, and a 0.5 mg/ml casein blocking solution for 10 minutes at room temperature, and a final deionized water rinse.

In the assay, antigen dilutions where: 1:5,000; 1:10,000; 1:20,000; 1:40,000; 1:80,000; and 1:160,000; and the conjugate solution was a 1:100 dilution of HRP labeled antibody containing 5 mg/ml casein and 50 mM MOPSO, pH 7.0.

One part of each antigen dilution was combined with one part conjugate solution immediately before use and applied to each surface. This was allowed to react for 2 minutes at room temperature, then each surface was rinsed with deionized water. Substrate was then added to each surface. The silicon wafer received TMBlue and the ELISA plate received TMB. This was allowed to react for 5 minutes at room temperature. At this point, the reaction was over and the silicon wafer was rinsed with deionized water and dried with nitrogen. The ELISA was stopped with $H_2SO_4$. A visual reading was made to determine the lowest antigen dilution differentiable from the negative and the test surface containing the insoluble product deposited on the surface put into the ellipsometer to measure the respective voltages.

OIA could be read out to a 1:40,000 antigen dilution as compared to ELISA (unstopped) which could be read to only a 1:10,000–1:20,000 dilution, while ELISA (stopped) could only be read to a 1:5,000–1:10,000 dilution by eye.

Instrument read results are shown in Tables 15a and 15b.

TABLE 15a

Catalytic Mass Enhanced Method (OIA)™ Results

| OBS[A] | Fold Antigen Dilution | Change in Intensity* |
|---|---|---|
| 2 | 0.000 | 0.006 |
| 2 | 5,000 | 0.339 |
| 2 | 10,000 | 0.154 |
| 2 | 20,000 | 0.059 |
| 2 | 40,000 | 0.023 |
| 2 | 80,000 | 0.013 |
| 2 | 160,000 | 0.011 |

[A]Number of observations made.
*Change in intensity is actual intensity minus background intensity recorded with the Comparison Ellipsometer.

TABLE 15b

ELISA Results
Optical Density Readings at 450 nM

| Dilution | 1 | 2 | 3 | 4 |
|---|---|---|---|---|
| 0 | 0 | 0.013 | 0.003 | — |
| 1:160,000 | 0 | 0 | 0.008 | 0.015 |
| 1:80,000 | 0.006 | 0.036 | 0.037 | 0.045 |
| 1:40,000 | 0.006 | 0.005 | 0.027 | 0.001 |
| 1:20,000 | 0.015 | 0.012 | 0.012 | 0.041 |
| 1:10,000 | 0.030 | 0.043 | 0.068 | 0.053 |
| 1:5,000 | 0.081 | 0.085 | 0.097 | 0.123 |
| 1:5,000 | 0.063 | 0.064 | 0.094 | 0.088 |

EXAMPLE 17

Latex and Catalytically Enhanced Assays

An enzyme-labeled assay was used to detect antigen from Streptococcus A and compared on the same silicon wafer with an assay using the amide modified surface activator latex, 0.161 µm (Rhone-Poulenc).

Both techniques are more sensitive than a commercially available (Wellcome Diagnostics) latex agglutination technique which has a cut-off at a 1:80 dilution of antigen. A direct instrumented comparison of the two techniques is presented below in Table 16. The mVolt readings given are a function of a change in light intensity recorded with the modified Sagax Comparison Ellipsometer.

TABLE 16

| Fold Antigen Dilution | mVolts/Latex | mVolts/Enzyme |
|---|---|---|
| 0 | 3.0 | 11.0 |
| 1:320 | 32.0 | 203.0 |
| 1:160 | 63.0 | 290.0 |
| 1:80 | 113.0 | 272.0 |
| 1:40 | 195.0 | 194.0 |
| 1:20 | 316.0 | 168.0 |
| 1:10 | 428.0 | 258.0 |

EXAMPLE 18

Multiple Analyte Protocol

Test surfaces and conjugated antibody preparations were produced as described in Example 16 for each of the following organisms, N. meningitidis, H. influenza Group B, Streptococcus pneumoniae, Streptococcus Group B, and E. coli K1. The test device was designed to accommodate these five test surfaces which were mounted onto the elevated platforms within the device (see, FIGS. 9A–E and 11A–E). A fixed volume of individual conjugate preparation for each of the following organisms, N. meningitidis, H. influenza Group B, Streptococcus pneumoniae, Streptococcus Group B, and E. coli K1 was prepared.

Equal volumes (75 µl) of a cerebral spinal fluid (CSF) sample and this conjugate preparation were mixed before pipetting one drop (approximately 25 µl) onto each of the five antibody coated test surfaces. The CSF samples were prepared with known levels and known combinations of antigens derived from the test organisms, as described in Example 16. Samples were incubated for 2 minutes, after which the test wafers were washed with deionized water and blotted dry. Substrate (TMB precipitating reagent) was added to each surface and incubated for 5 minutes. The wafers were washed with deionized water, blotted dry, and read. In this manner, a single sample was easily analyzed for the presence of one or more analytes. This poly-specific reagent maintained the specificity observed with the mono-specific reagents. No false positive responses were observed, and positive responses were comparable to the signal produced in a mono-specific test procedure.

EXAMPLE 19

Strep A Assay Device

The details of formation of the device shown in FIGS. 8A–8G is now provided. Monocrystalline silicon wafers, 100 mm in diameter, polished on one side, 20 mil ±2 mil were purchased from a semi-conductor supplier. The wafers were coated with 495 Å±15 Å silicon nitride or titanium dioxide using processes described above. Each wafer was sawed to a depth of 3.5 mils generating a pattern of 0.75 $cm^2$ sections. This allows the wafers to remain intact for subsequent processing. The wafers were then coated with the T-polymer siloxane as described in Example 5. A final polymer thickness of 100 Å±5 Å is used. Polymer coated wafers are cured for 24 ±2 hours at 145° C.±5° C.

Polymer coated wafers were submerged in a solution containing 5 µg/ml of an affinity purified rabbit anti-Strep A antibody in 0.1M HEPES (N-[2-Hydroxyethyl] piperazine-N'-[2-ethanesulfonic acid]) at pH 8.0. Wafers were coated with the antibody solution for 16–20 hours at 2° C.–8° C. The wafers were rinsed with deionized water and then dried under a stream of nitrogen. A procedural control was applied to the center of each 0.75 cm² using an x,y translational stage. A 1–2 μl spot was applied and incubated for 3 minutes at ambient temperature (20° C.). The concentration of antigen used was empirically determined to provide an intermediate color change. Antigen was mixed in deionized water. The antigen solution was rinsed from the surface with deionized water and then dried under a stream of nitrogen. The wafers were then submerged in a solution containing 0.5% of degraded gelatin in 50 mM MOPS (3-[N-Morpholino]propanesulfonic acid), pH 7.0 for 20 minutes at ambient temperature. The wafers were removed from the solution and dried under a stream of nitrogen. The gelatin layer serves to stabilize the antibody coating, and aids in storage of the device. The wafers are purple in color. The gelatin layer was fully hydrated by exposure of the wafers to steam for 30 seconds. The wafers were then air dried. The wafers will return to the original gold color. The wafers were then broken into individual 0.75 cm² test pieces.

Referring to FIGS. 8A–8G, the molded test device has the pre-cut absorbent pad placed in the bottom and the protective cover snapped into place. The upper laminate of blotting materials was placed in the lid of the device and the protective cover snapped into place. A small drop of epoxy is applied to the raised pedestal in the center of the device and a test surface applied. The glue was allowed to set, and then the device is closed and placed in the kit.

The antibody preparation used to coat the surface, or a separate antibody preparation, was conjugated to HRP using standard periodate chemistries described by Nakane. The exact dilution of conjugated antibody used in the mass enhancement reagent will depend on the level of HRP incorporation and the affinity and avidity of the antibody preparation used. The conjugate preparation was diluted in a solution containing 50 mM MOPSO (3-[N-Morpholino]-2-hydroxypropanesulfonic acid), pH 7.0, 20 mg/ml of standard alkaline treated casein, 0.3% (v/v) TWEEN 20™ detergent polyoxyethylenesorbitan monolaurate and 0.5% (v/v) Proclin 300 (Rohm and Haas). Conjugate solution was dispensed into Wheaton Natural polyethylene dropper bottles. Delivered drop size was approximately 30 μl. All other reagents were also dispensed into the Wheaton Natural dropper bottles.

Extraction tubes were prepared by dispensing 100 μl of a solution containing 2.3M NaNO₂ and 0.01% isopropanol into polyethylene tubes and allowing the solution to dry onto the tube. This may be accomplished by drying at ambient temperature, under circulating air, or at 45° C.

The reagent composition was as follows:
Reagent #1: 0.25M Acetic Acid with 0.035 mg/l bromcresol green
Reagent #2: 1.5M MOPSO, pH=7.3, with 0.2% (v/v) TWEEN 20™ detergent polyoxyethylenesorbitan monolaurate 0.5% (v/v) Proclin 300, and 20 mM EDTA.
Reagent #3: Conjugate.
Reagent #4: Deionized water containing 0.1% Proclin 300.
Reagent #5: Commercial preparation of precipitating TMB.

The test procedure for use of this device was as follows.
1. Remove reagent(s) from refrigerated storage and allow to warm to room temperature.
2. Remove an extraction tube containing dry reagent from the kit and place it upright in a rack or holder.
3. Label extraction tubes and test devices with appropriate patient information. Place test devices on a level surface while the assay is being performed.
4. Add 3 drops of Reagent 1 into the extraction tube and shake it gently to dissolve the dry reagent in the bottom. The liquid should become light green in color when dissolved and properly mixed. Color change in the extraction tubes may not be evident with bloody specimens, however assay performance is not affected.
5. Within 1 minute, place a throat swab containing a specimen or positive control into the tube. Press the swab against the sides of the tube while rolling the swab so that the liquid is moved in and out of the fiber tip. Allow the swab to incubate in the extraction solution for a minimum of 2 minutes.
6. Hold the swab shaft to the side and add 3 drops of Reagent 2 directly into the extraction tube. Use the swab to mix the reagent with the extract until the solution color changes from green to blue.
7. Separate the extraction solution from the swab by rolling the swab against the wall of the extraction tube while squeezing the sides of the tube as the swab is withdrawn. Discard the swab and retain the contents of the tube. Retain as much fluid from the swab as possible.
8. Add 1 drop of Reagent 3 to the extract and mix thoroughly. Do not let stand more than 30 minutes.
9. Use a clean transfer pipette to transfer 1 drop of the solution directly onto the center of the surface of the corresponding test device. Do not cover the entire surface of the test device.
10. Incubate the drop on the test surface for 2 to 5 minutes.
11. A vigorous wash of 1–2 second duration is important. Rinse the surface of the device using Reagent 4 wash solution with care not to exceed the capacity of the absorbent material surrounding the device.
12. Confirm that the blotting device is in position #1. Close the lid of the device momentarily to remove residual moisture from the surface. Blot with a clean surface each time blotting is necessary. Blotter should be in position I when blotting for the first time. If in position II, move to position I for the second blot. Repeated blotting in the same position may compromise test results.
13. Open the lid and apply 1 drop of Reagent 5 directly onto the center of the surface of the test device and incubate for 4 to 10 minutes. If placement of the first drop was not directly onto the center of the device, place the Reagent 5 drop directly over the area of the first drop.
14. Vigorously rinse the surface of the device for 1–2 seconds using Reagent 4 wash solution.
15. Move the blotter in the top of the device to position #2 and close the lid of the device momentarily to remove residual moisture from the surface. Open the lid and examine the test surface for a color change.

POSITIVE RESULT:
Solid blue/purple colored reaction circle of any intensity appears in the center of the device surface.

NEGATIVE RESULT:
No blue/purple colored reaction circle of any intensity appears on the test surface.

A Procedure control is present on each test surface. It appears as a small blue/purple dot in the center of the test surface upon completion of each positive or negative test. A negative test result will show only the procedure control. A positive test result will show the procedure control within the reaction circle. With very strong positive results, the procedure control may be less apparent within the reaction circle.

If the procedure control does not appear, the procedure can be repeated following the instructions. The reacted test surface and the color change associated with a positive reaction will not deteriorate over time. Therefore, the test device may be considered a permanent record. If a test device is to be saved for reference, the blotting material in the lid should be removed and disposed of in a biohazard container, and the device should be closed for storage.

EXAMPLE 20

Sensitivity of OIA Device

The analytical sensitivity of Strep A OIA was compared with commercially available Strep A kits using a cell suspension of a known density and extracting an aliquot of this suspension according to each kit's assay protocol. *Streptococcus pyogenes*, Lancefield group A, was obtained from the American Type Culture Collection (ATCC #12344) as primary culture on a slant tube. Cell suspensions were made sterile normal saline and serially diluted with the normal saline. Results from the study demonstrate at least a 10–100 fold greater sensitivity in the OIA device of this invention compared to at least six commercially available test kits.

Table 17 compares the clinical sensitivity of the Strep A OIA to the product insert claims of several commercially available rapid Strep A assays. The majority of these rapid assays discard all samples with Strep A colony counts of less than 20, however, in the numbers presented for the Strep A OIA assays none of the samples were discounted. Strep A OIA demonstrates a significant improvement in sensitivity relative to these rapid tests.

After inoculation, the swab was returned to the transport tubes and assayed following the Strep A OIA test procedure. Three drops of acid generating solution were added to extraction tubes and mixed well to dissolve a dried reagent. The swabs were placed in the extraction tube, thoroughly saturated with extraction reagents, and allowed to incubate for 2 minutes in the solution. Three drops of neutralizing solution were added to the extraction tubes and the swabs were used to mix the reagents. The extracted swabs were expressed against the side of the tube, then discarded. This extraction technique is common to most rapid GAS tests and liberates GAS antigen from the bacterium.

One drop of catalyst was added to the extract and mixed thoroughly. A drop of this solution was applied to the center of the test piece (FIGS. 8A–8G). Samples were incubated on the test surface for 2 minutes, then the test surface was rinsed with water and blotted dry by closing the lid. A drop of mass enhancer was applied to the center of the test surface and incubated for 4 minutes. The surface was again rinsed with water and blotted as before. The test results were determined without knowledge of the culture results.

An enhanced culture method was designed to confirm the presence of bacteria. In this method, the pledgets (plugs separating transport media and swab) were removed from all transport tubes, placed in Todd-Hewitt broth and incubated for 24–48 hours at 35° C.–37° C. If growth patterns con-

TABLE 17

Comparison of Test Kits for Detection of Group A Streptococcal Antigen Directly from Throat Swabs[1]

| Product Name/ Manufacturer | Methodology | Assay Time | | Sensitivity | Specificity | Accuracy | Predictive Value | |
|---|---|---|---|---|---|---|---|---|
| | | Extraction/Reaction | | | | | pos | neg |
| STREP A OIA BioStar Medical Products, Inc. | Mass enhanced on a silicon surface | 2–10 min | 6 min | 100%[2] | 98.9% | 99.1% | 100% | 98.9% |
| OIA Strep A BioStar Medical Products, Inc. | Ab coated latex on silicon surface | 2–10 min | 2 min | 83.3%[2] | 97.4% | 94.7% | 88.2% | 96.1% |
| Test Pack + Strep A Abbott Labs | Ab coated colloid on membrane | 1–30 min | 5 min | 93.7% | 94.5% | 94.3% | 89.7%[3] | 96.7%[3] |
| Cards[4]-OS Strep A Pacific Biotech, Inc. | Ab coated, dyed latex on membrane | 2–60 min | 5 min | 96.6%[4] | 96.8% | 96.7% | 95.5% | 97.6% |
| Directigen 1,2,3 Strep A Becton-Dickinson | Ab coated, dyed liposome on membrane | 3–120 min | not given | 90% | 92% | 91.2% | 75%[3] | 97%[3] |
| Reveal Colour Strep A Wellcome Diagnostics | Ab coated, dyed latex, agglutination | 2 min | 3 min w/rocking | 86% | 94% | 94% | 81% | 96% |

[1]Data obtained from manufacturers' package inserts.
[2]Based on all specimens.
[3]Data calculated from tables in package inserts.
[4]Specimen plate colony count not revealed in package insert.

Swabs were collected from patients presenting symptoms of pharyngitis using a single swab and standard specimen collection techniques. Four independent laboratories were used in the study. Immediately after the specimen was collected, the swab was returned to the transport tube and the capsule containing transport media crushed. Each site inoculated a 5% Sheep blood agar (SBA) plate with a specimen and plates were then incubated at 35° C.–37° C. Two of four sites incubated the plates under anaerobic conditions for 24 to 48 hours and two sites incubated the plates in an enriched $CO_2$ environment. Each site reported results as negative or positive with positives confirmed by a serotyping method.

sistent with the bacteria were observed, colonies were selected, re-isolated if necessary, and confirmed using a commercially available Streptococcus serotyping kit.

In a clinical study a total of 778 samples from four sites were examined. The SBA culture method determined 70 specimens to be positive, 4 of these specimens were determined to be negative relative to the enhanced culture method. The enhanced culture method determined that 92 specimens were positive. The sensitivity of SBA culture was 71.7% relative to the enhanced culture method for the frequency and population tested. These data support previous literature results showing conventional SBA culturing methods to be less sensitive than enhanced culture methods. Therefore, the consideration of conventional SBA culture methods as the "gold standard" should be re-evaluated.

OIA results were evaluated relative to both SBA culture and enhanced culture methods. The Strep A OIA yielded a sensitivity of 92.9%, a specificity of 94.8%, and an accuracy of 94.6% relative to the SBA culture, for the frequency and population tested. Strep A OIA appears to lack specificity relative to the SBA culture methods. However, the actual limitation lies in the SBA culture technique as 26 of the apparent Strep A OIA false positives were, in fact, true positives. The sensitivity of the Strep A OIA relative to culture appears to be reduced because of 4 SBA positive results which were Strep A OIA negative. These results were later determined to be culture non-isolates by the enhanced culture method. Strep A OIA detected 91 out of 92 enhanced culture positives yielding a sensitivity of 98.9%. It is important to note that the performance results include all data collected, irrespective of colony count.

EXAMPLE 21

Instrument Reading Protocols

1) Photodiode Modified Comparison Ellipsometer

The Comparison ellipsometer was modified as previously described above. The eyepiece was connected to a CCD camera to allow samples to be centered in the elliptical reticle. The zoom was adjusted so that the sample spot is completely enclosed in the ellipse.

The test strip used in the assay was 1 cm wide and 4–5 cm in length. These dimensions are easy to handle manually. Any dimension of test piece may be used with the proper design of sample positioning devices. Samples were applied as 20 µl drops evenly spaced along the length of the slide. One section was left for measurement of the test surface background. Samples were assayed as described in the previous examples.

The test strip was placed on the instrument's sample platform and the background section of the surface was centered in the ellipse. The sample platform has x,y positioning capabilities. Once the test surface was positioned, the background reading was taken at the photodiode. An LED displays the background intensity of the background section in volts. Computer software may also be designed to record the background intensity. After this measurement was complete, the platform was advanced to record a reading from a negative sample. The voltage was recorded directly, or may be recorded as sample minus background. The platform was advanced until all samples were measured.

The instrumented read out may provide a qualitative answer of yes or no relative to a pre-set signal. The assay would include a negative control and a low positive, or cut-off concentration and objectively evaluate samples relative to this threshold value.

If the assay is quantitative, the test surface or test device will allow measurement of a negative control and one or more known positive controls. Samples values will be compared to this curve for quantitation. Positive controls may cover several broad ranges if a semi-quantitative answer is adequate for the application being considered.

Monochromatic Light Source, Comparison Ellipsometer

This instrument has a smaller optical path due to the use of a light source that is collimated, a smaller reference surface, a smaller sample platform, polarizers positioned immediately next to the light source and the detector, and eliminating the lens system required for visual examination of the surface.

The reading protocol for this particular instrument accommodates five separate samples or four controls and one sample or two controls and three samples, etc. The sample slide is connected to a rotating post which controls the slides position. Alignment is not achieved by visual placement, but by sample placement on the test surface and the platform advancement. Any arrangement of the test surface may be used by modifying the x,y positioning platform. This allows the use of a test surface which can examine a large number of samples.

This instrument uses a photodiode detector which is masked to match a fixed sample size and the slide positioning and sample application allows the sample spot to fill the mask. Readings are made from an LED display in the cover of the instrument. Readings are in millivolts.

EXAMPLE 22

Group B Streptococcus

An optically active test surface was produced by immobilizing either a polyclonal or monoclonal anti-GBS antibody on the previously described siloxane coated surface. The antibodies were group specific, but may be to any of the group specific epitopes found on the GBS polysaccharide. The polyclonal preparations used were a protein G purified IgG fraction that was adsorbed to whole cells. The coating antibody concentration was in the range of 150 to 500 µg of antibody per 100 mm wafer, and was coated at 2–8 degrees C. for 12 to 16 hours. The 100 mm wafer may or may not possess a 495 Å silicon nitride. In particular, a monoclonal antibody was found to coat best at 200–300 µg/wafer in a buffer containing 50 mM Sodium Acetate at pH 5.0. A polyclonal antibody was found to coat the surface equally well but in a buffer containing 0.1M HEPES, pH 8.0. Buffers covering the pH range of 5.0 to 9.0 have been demonstrated to provide an effective antibody coating. Once the antibody was immobilized on the test surface, an overcoat of 0.5% degraded gelatin in 50 Mm MOPS, Ph 7.0 is applied as previously described. Antibody coated test surfaces were placed in single test devices prior to use.

For mass enhancement of the GBS assay, a group specific polyclonal antibody preparation was conjugated to HRP using the Nakane periodate method. Conjugation of the antibody to HRP at high Ph, greater than 9.75, resulted in an increase in non-specific binding. Optimal conjugating Ph was established at 9.0 to 9.75.

The GBS group specific antigen was extracted from the organism using an acid extraction protocol. A mixture of 0.25M acetic acid and 2.3M sodium nitrite was used to generate hyponitrous acid. The acetic acid was found to effectively extract the GBS antigen in the range of 0.1M to 1.0M. Antigen was extracted from the organism for 2 minutes. For all results described here, ATCC strain number 12386 was used. The solution was neutralized using an buffer containing 1.5M MOPSO, Ph 7.3, 0.2% TWEEN 20™ detergent, polyoxyethylenesorbitan monolaurate 0.5% Proclin300, and 20 Mm EGTA by adding an equal volume of the neutralizing buffer. A final Ph range of 6.0 to 7.5 is desired.

The extracted antigen was mixed 5:1 (sample:conjugate) with a 1:150 dilution of the conjugate preparation containing 50 Mm MOPSO, Ph 7.0, 20 mg/ml alkaline treated casein, 0.3% TWEEN 20™ detergent, polyoxyethylenesorbitan monolaurate and 0.5% Proclin300. A sample:conjugate ratio of between 3:1 and 10:1 was acceptable. The sample/conjugate mixture was incubated for 5 minutes at room temperature, then 20 μl of the mixture applied to the test device and incubated for 5 minutes at room temperature. The devices were used as previously described for washing and drying the test surface. After the test surface was dried, a drop of TMB precipitating substrate was applied to the device and incubated for 5 minutes at room temperature. After the wash/dry protocol was completed, the test result was interpreted. When instrumented results are desired, the wash dry protocol is accomplished by rinsing the test surface under a stream of deionized water and drying under a stream of nitrogen. The initial incubation of sample/conjugate was not required but was observed to increase the sensitivity of the assay. Assay sensitivity could be further increased with additional incubation time.

The current GBS assay demonstrated excellent tolerance to changes in the final extraction Ph. The visualization of a low positive was not effected by a change in Ph over the range 6.75 to 8.0, see Table 19. A visual scale was established for scoring results, wherein a 1+ or 2+ was a very weak purple spot on a gold background. A value of 10+ is a very strong blue result.

TABLE 18

GBS Sensitivity as a Function of Assay Time

| Sensitivity[a] | Total Assay Time[b] |
|---|---|
| $3 \times 10^6$ | 5[c] |
| $3 \times 10^4$ | 10[d] |
| $3 \times 10^3$ | 15[e] |

[a]Sensitivity is expressed in the number of cells/swab.
[b]Time is in minutes.
[c]Incubation times were 1 minute for sample/conjugate; 2 minutes for the sample on the surface; and 2 minutes for substrate.
[d]Incubation times were 5 minutes each for the sample on the test surface and substrate.
[e]Incubation times were 5 minutes each for the sample/conjugate, sample on the surface, and substrate.

TABLE 19

GBS DETECTION AS A FUNCTION OF THE FINAL ASSAY pH

| CELLS | pH 6.75 | pH 7.0 | pH 7.25 | pH 7.5 | pH 7.75 | pH 8.0 |
|---|---|---|---|---|---|---|
| $3 \times 10^6$ | 10+ | 10+ | 10+ | 10+ | 10+ | 10+ |
| $3 \times 10^5$ | 7+ | 7+ | 7+ | 7+ | 7+ | 7+ |
| $3 \times 10^4$ | 2+ | 2+ | 2+ | 2+ | 2+ | 2+ |
| 0 | − | − | − | − | − | − |

EXAMPLE 23

Chlamydia Detection

An optically active test surface, with or without the 495 Å silicon nitride coating, was coated with the polymeric siloxane, T-polymer, as previously described. These polymeric coated supports were further coated with a solution of between 1 and 10 μg/ml of bovine serum albumin (BSA) in 100 Mm sodium carbonate, pH 9.6, at 2–8 degrees C. for 12 to 16 hours. Subsequently, the test surface was coated with 0.5% degraded gelatin in 50 Mm MOPS, pH 7.0, at room temperature for 20 minutes and then dried under a stream of nitrogen. Coated test surfaces were mounted into the single use test devices previously described.

The Chlamydia specific LPS antigen was extracted from the synthetic fiber swab used for sample collection by immersing the swab in a solution (approximately 120 μl) of 0.01M PBS with 0.1% (w/v) chenodeoxycholic acid (CDOC), sodium salt, which had been alkalized with 10 μl in 1 ml of buffer of 1.0N NaOH to a final Ph of 11.5. Initially the CDOC was solubilized in absolute methanol at 0.2 g/ml. The swab was ideally vortexed in this solution for approximately 10 seconds and then incubated for 5 minutes at room temperature. The swab was then expressed of residual solution by squeezing the flexible extraction tube (polypropylene). An equal volume of 100 Mm $Na_2HPO_4$ with 0.1% CDOC at pH 7.0 was added to adjust the final pH to between 7.0 to 7.5.

A mass enhancement reagent was prepared by conjugating an anti-Chlamydial LPS antibody to HRP using the method of Nakane. The stock conjugate was diluted 1:75 to 1:200 in a diluent containing 50 mM MOPSO, pH 7.0, with 20 mg/ml of alkaline treated casein, 0.3% TWEEN 20™ detergent, polyoxyethylenesorbitan monolaurate and 0.5% Proclin500.

Approximately 30 μl of the extracted sample was put onto the BSA/polymeric siloxane test surface and incubated from 5 to 10 minutes at room temperature. Then approximately 30 μl of an anti-Chlamydial LPS antibody conjugated to HRP was added to the sample spot on the test surface and incubated for 1 to 5 minutes at room temperature. The test surface was washed with 1 to 2 ml of water and dried in the device as previously described. Approximately 30 μl of the TMB precipitating substrate was applied to the surface and incubated for 10 to 15 minutes at room temperature. The test device was washed and dried as previously described.

Alternatively, an antigen preparation was serially diluted from 1:100 to 1:320 in 0.01M PBS, pH 7.4. Three fold serial dilutions were performed. Five μl of these dilutions were added to 500 μl of 0.1% chenodeoxycholic acid in 0.01M PBS with 10 mM NaOH (final pH was 11.5). These were vortexed and allowed to sit for 5 minutes at room temperature. Five hundred μl of 100 mM phosphate buffer (mono and di basic mix) was added to neutralize the extraction buffer and 15 μl of this added to the wafer surface. This was incubated on the surface for 10 minutes at room temperature. A 15 μl aliquot of a 1:75 dilution of an anti-LPS antibody-HRP conjugate was added directly to the antigen spot on the surface and incubated at room temperature for the designated time. The wafer was washed with deionized water and blown dry under a stream of nitrogen. Substrate (30 μl) was applied to the antigen/conjugate spot and incubated for the designated time. The wafer was washed and dried as before and the intensity of captured antigen recorded with the photodiode modified Comparison Ellipsometer. The data was corrected for background. Readings are in millivolts are the average value for 2 readings, see Table 20. Table 20 demonstrates the effect of increased incubation times on the sensitivity of the assay.

TABLE 20

| SURFACE | CONJUGATE | SUBSTRATE | ANTIGEN DILUTION | mV | VISUAL |
|---|---|---|---|---|---|
| | | | Incubation Times (minutes) | | |
| 5 | 5 | 10 | 0 | 12.4 | – |
| | | | 1:320 | 52.5 | 1+ |
| | | | 1:160 | 86.0 | 1+ |
| | | | 1:40 | 109.5 | 3+ |
| | | | 1:20 | 708.0 | 5+ |
| 10 | 5 | 15 | 0 | –6.3 | – |
| | | | 1:320 | 181.5 | 2+ |
| | | | 1:160 | 172.9 | 2+ |
| | | | 1:40 | 861.1 | 5+ |
| | | | 1:20 | 1601.4 | 10+ |

EXAMPLE 24

Human Anti-HIV Detection

A silicon wafer, 100 mm diameter, was coated with polybutadiene (PBD) as previously described. The PBD coated optical test surface was coated with 20 µg/ml of a synthetic peptide corresponding to GP41 of the HIV virus which was conjugated to bovine serum albumin (BSA). This antigen preparation was diluted in 10 mM Potassium Phosphate, 0.85% NaCl, at pH 7.0, and the test surface was coated with the antigen for 2 to 3 hours at room temperature with agitation. The test surface was removed from the coating solution, rinsed with deionized water, and dried under a stream of nitrogen. The gp41 protein is very hydrophobic and binds well to the hydrophobic PBD surface.

A series of seronegative and seropositive human serum samples were used to test the gp41/BSA coated surface. Five microliter samples of serum were applied to the test surface and incubated for 15 minutes at room temperature. Antibody capture on the antigen surface was measured using the Comparison ellipsometer modified with a CCD camera. Results were reported in Grayscale units.

TABLE 21

Host Antibody Capture on a gp41 Surface

| Seropositive Serum Grayscale | Seronegative Serum Grayscale |
|---|---|
| 93.07 | 8.83 |
| 43.53 | 3.65 |
| 48.64 | 5.51 |
| 60.29 | 7.64 |
| 65.36 | 3.62 |

The average value reported for a seronegative serum was 5.85±2.1 grayscale units making any value of 12.15 grayscale units (negative+3 standard deviations) a positive response. The varying level of grayscale reported for the seropositive samples reflects varying antibody titers.

A recombinant antigen preparation which was a fusion of gp41 and p24 of the HIV virus was also evaluated as a coating material for the optical test surfaces of this invention. A 100 mm diameter silicon wafer was coated with PEI as previously described. This optical test surface was submerged in a coating solution containing 2.5 µg/ml of the fusion protein in 50 mM sodium carbonate, pH 8.0 and incubated for 3 hours at room temperature. The optical test surface was then rinsed with deionized water and dried under a stream of nitrogen. The optical test surface was tested for response to serum controls: negative, low, medium, and a high positive anti-HIV. Five microliters of each serum sample was applied to the surface and incubated for 15 minutes at room temperature. Surfaces were rinsed with deionized water and dried under a stream of nitrogen. Results were obtained with the modified Comparison Ellipsometer as described above.

TABLE 22

Antibody Capture by gp41/p24

| Serum Sample | Grayscale Value |
|---|---|
| Negative | 0.0 |
| Low | 29.28 |
| Medium | 41.22 |
| High | 52.94 |

EXAMPLE 25

RSV Detection

Optically active test surfaces were coated with the polymeric siloxane as previously described. These surfaces were placed in a 10 µg/ml polyclonal anti-RSV antibody solution. A number of buffers were examined in the antibody coating step, including HEPES, pH 8.0; Acetate, pH 5.0; Carbonate, pH 9.5; Borate, pH 8.0; and Phosphate, pH 7.4. All buffers were 0.1M in concentration. The 0.1M sodium carbonate, pH 9.5 was found to be optimal. Surface preparations were analyzed using a sequential assay. A 20 µl aliquot of positive control was applied to the surface and incubated for 10 minutes at room temperature. Surfaces were rinsed with deionized water and dried under a stream of nitrogen. Antibody-HRP conjugate (20 µl) was applied to the test surface, incubated 10 minutes, washed, dried, and then 20 µl of precipitating substrate applied for 10 minutes, followed by a wash/dry step. Antibody was coated for 12 to 16 hours at 2–8 degree C. The surface was rinsed and incubated for 20 minutes at room temperature in a solution containing 0.5% degraded gelatin, 50 mM MOPS, pH 7.0 and then dried under a stream of nitrogen.

The mass enhancement reagent was prepared by the Nakane method. A monoclonal antibody to the nuclear peptide of RSV was conjugated to HRP. The stock conjugate was diluted 1:30 to 1:250 in a solution containing 50 mM MOPSO, pH 7.0, and 20 mg/ml alkaline treated casein, 0.3% TWEEN 20™ detergent, polyoxyethylenesorbitan monolaurate and 0.5% Proclin300.

An alternate assay protocol involved thoroughly mixing 30 µl of a nasal washing with 30 µl of 10% Tween20 in PBS and 30 µl of a 1:40 dilution of the conjugate. A 30 µl aliquot of this sample was applied to the test surface and incubated for 12 minutes at room temperature. The rinse and drying protocols described for the single use test device were used. TMB precipitating substrate was applied to the surface, incubated for 8 minutes at room temperature, rinsed, and dried prior to interpretation.

TABLE 23

RSV Standard Curve

| Fold Dilution | Ellipsometric Intensity (mV) | Visual |
|---|---|---|
| 0 | 0.0020 | – |
| 1:1280 | 0.0244 | – |
| 1:640 | 0.0256 | + |
| 1:320 | 0.0356 | 1+ |
| 1:160 | 0.0694 | 2+ |
| 1:80 | 0.0578 | 2+ |
| 1:40 | 0.1198 | 3+ |
| 1:20 | 0.2236 | 4+ |
| 1:10 | 0.5235 | 5+ |
| 1:5 | 0.8833 | |

An UV inactivated antigen preparation from the Long Strain of RSV was purchased and contained a total of $2\times10^5$ PFU. This antigen preparation was diluted in buffer, 1:1, and assayed as described above. 15 µl of each sample was applied to the surface and represented 7.5% of the total antigen available.

TABLE 24

RSV Standard Curve

| Antigen Conc. | Ellipsometric Intensity (mV) |
|---|---|
| 0 | 0.0079 |
| $1 \times 10^5$ | 1.0221 |
| $1 \times 10^4$ | 0.3124 |
| $1 \times 10^3$ | 0.0466 |

EXAMPLE 26

Wavelength Dependence for a Thin Film Analyzer

Lundstrom, et al., U.S. Pat. No. 4,521,522, describe an instrument in which an incoming light beam passes through a polarizer and is reflected off the film at Brewster's angle for the substance to be measured. The incident radiation is polarized parallel to the plane and angle of incidence. The instrument requires the use of only one polarizer, however, when a second polarizer is used it must be set to exactly 90° relative to the first polarizer. A single polarizer is all that is required as there is no change in the polarization of the incident light upon reflection. For this polarization there is no change in the polarization for any incidence angle, demonstrated by the fact that the polarizer may be situated in either the incident or reflected beams. Only that part of both the light incident on the sample and the reflected light which is polarized parallel to the plane of incidence is measured.

The method is based on the minimum in reflectance observed at this angle when light polarized parallel to the plane of incidence is incident on the interface between dielectric media. This phenomena is only observed at Brewster's angle. A substrate with a high refractive index is required. A metal, which is highly reflective, but has a low refractive index has too shallow a reflection minimum for this technique.

For better signal resolution of small thickness changes, the above method requires a layer of oxide over the substrate to shift the minimum reading to an acceptable position in the reflection curve observed for polarized light, allowing a small thickness change to produce a larger change in the reflected light intensity. When an attachment layer is included, it is included for optimization of the substrate relative to the reflectance minimum, and not to increase performance of the receptive material.

With the pure parallel polarized light (p-polarized) described by Lundstrom a very minor change in the % reflectivity is observed with analyte binding; there is no change in the polarization of the light. In the current invention, in addition to the p-polarized light, there are also components of perpendicularly polarized light (s-polarized) in the incident light beam. Very large changes in rotation of the polarized light are observed upon interaction with thin films and these changes in the polarization rotation are measured as well as any change in intensity.

For very large angles of incident light, using the current invention, some degree of ellipticity can be generated in the light reflected from the test surface. The current invention maximizes a change in polarization rotation upon reflection with added mass, and is not associated with a minimum in reflectivity. The rotation of polarization upon reflection observed with the current invention is entirely absent for pure parallel polarized light. An additional advantage of the current invention is that nearly any substrate and dielectric thin film may be used, since it does not rely on the Brewster angle. Also the angle of incident light is not critical and does not have to be changed with the type of substrate material.

The current invention uses a monochromatic, collimated, light source such as a laser. It also includes a polarizer between the light source and the test surface oriented such that both p- and s-polarized components are incident on the surface. If the light source is sufficiently well polarized this polarizer is unnecessary. The light reflected from the surface passes through a second polarizer (the analyzer) and enters a photodiode. The fraction of s-polarized light is selected to maximize the signal change as a function of thickness while maintaining a low background light intensity. The light becomes elliptically polarized upon reflection, with the ellipticity and angle of rotation of polarization depending in a very sensitive manner on the optical properties of the surface. In a comparison ellipsometer, such as described in U.S. Pat. Nos. 4,332,476, 4,665,595, and 4,647,207, the light is then reflected off a reference surface which cancels that ellipticity in regions where the reference surface is optically identical to the sample surface. The current invention does not require a reference surface because it is not designed to establish the exact physical thickness or refractive index of a given material. Instead, the intensity of the light passed through the analyzer provides a measure of the polarization rotation concomitant with the ellipticity, and hence a relative measure of optical properties of the surface. Thus, it provides a simple means to measure the change in the thickness and refractive index of the surface materials.

The measurement protocol is essentially unmodified from the instrument above using x, y positioning platforms to determine where readings are made. However, the analyzing polarizer must be rotated to a pre-selected value for the background prior to making an initial reading. The preferred embodiment includes a polarizer near the analyzer. Light is transmitted through the analyzer to a detector. Readings may be recorded in volts or millivolts. Readings may be displayed on an LED or other display device or captured by a data processing package.

The impact of thin films on the lightness and wavelength dependence of light reflected from silicon was modeled with a computer simulation. The response of a thin film with a refractive index of 1.459 was modeled using a silicon surface and varying the thickness from 0 to 12 nm. The wavelength ranges examined were 400–420 nm, 540–560 nm, and 680–700 nm. An increase in lightness from the minimum lightness to the maximum lightness represents an increase in light intensity as a function of an increase in thickness. The lightness is a logarithm function of light intensity. From this data, the maximum sensitivity change as a function of thickness was achieved with a 540–560 nm light source. These data were generated using a 70° angle of incidence and the values will change slightly with the angle of incidence.

TABLE 25

| Wavelength | Min. Lightness | Max. Lightness | Change |
|---|---|---|---|
| 400–420 | −6.5 | −4.5 | −2.0 |
| 540–560 | −4.2 | −1.7 | −2.5 |
| 680–700 | −6.0 | −4.3 | −1.7 |

To confirm these observations, a standard antigen dilution curve was generated using the 9 minute assay protocol described in example 28. Intensities from the antigen dilution curve were measured, using the photodiode modified Comparison Ellipsometer, as a function of incident light wavelength. As the Thin Film Analyzer is a simplification of the Comparison Ellipsometer similar results are anticipated. Varying wavelengths of incident light were achieved by filtering white light through a narrow bandpass filter to select specific wavelengths. All filters were Corin P70 series filters.

TABLE 26

| Incident Light | Antigen Dilution | mV Response |
|---|---|---|
| White | 0 | 310 |
|  | 1:9600 | 317 |
|  | 1:4800 | 319 |
|  | 1:2400 | 371 |
|  | 1:1600 | 483 |
|  | 1:1000 | 780 |
|  | 1:400 | 1128 |
| 550 nm | 0 | 28 |
|  | 1:9600 | 29 |
|  | 1:4800 | 30 |
|  | 1:2400 | 36 |
|  | 1:1600 | 56 |
|  | 1:1000 | 93 |
|  | 1:400 | 176 |
| 600 nm | 0 | 33 |
|  | 1:9600 | 33 |
|  | 1:4800 | 34 |
|  | 1:2400 | 42 |
|  | 1:1600 | 66 |
|  | 1:1000 | 113 |
|  | 1:400 | 221 |
| 450 nm | 0 | 9 |
|  | 1:9600 | 9 |
|  | 1:4800 | 9 |
|  | 1:2400 | 11 |
|  | 1:1600 | 17 |
|  | 1:1000 | 27 |
|  | 1:400 | 50 |

EXAMPLE 27

Thin Film Analyzer Angle Dependence

The thin film analyzer shown in FIG. 14a was used with a 672 nm diode light source and the dual polarizer set-up diagrammed. The laser diode and photodiode were both mounted to accurately assess the angle of incidence and detection relative to a normal angle of incidence. Strep A antigen dilution curves were used to examine the angle dependence of the analyzer. The detector used with the thin film analyzer prematurely saturates, actual dynamic range is 3500+ mV. For a reference, the antigen curves were also examined with a small comparison ellipsometer also equipped with a 672 nm laser diode source.

TABLE 27

| Comparison Ellipsometer Readings | | | |
|---|---|---|---|
| Antigen Dilution | Average mV | 3SD | Range |
| 0 | 160.3 | 9.69 | 150.6–170.0 |
| 1:9600 | 190.4 | 5.58 | 184.8–195.9 |
| 1:2400 | 367.4 | 15.9 | 351.1–383.3 |
| 1:1000 | 766.0 | 26.3 | 739.7–792.3 |
| 1:400 | 1623.7 | 1.4 | 1622.3–1625.1 |

TABLE 28

| Thin film Analyzer | | | | |
|---|---|---|---|---|
| Angle | Antigen Dilution | Average mV[a] | 3SD | Range |
| 30°* | 0 | 12.0 | | |
|  | 1:9600 | 68.0 | | |
|  | 1:2400 | 90.0 | | |
|  | 1:1000 | 188.0 | | |
|  | 1:400 | 204.0 | | |
| 40°* | 0 | 64.0 | | |
|  | 1:9600 | 78.0 | | |
|  | 1:2400 | 84.0 | | |
|  | 1:1000 | 197.0 | | |
|  | 1:400 | 343.0 | | |
| 50° | 0 | 221.3 | 7.95 | 213.4–229.3 |
|  | 1:9600 | 263.4 | 13.2 | 250.2–276.6 |
|  | 1:2400 | 370.9 | 28.2 | 342.7–399.1 |
|  | 1:1000 | 574.2 | 54.0 | 520.2–628.2 |
|  | 1:400 | 1063.7 | 76.8 | 986.9–1140.5 |
| 56° | 0 | 133.3 | 9.0 | 124.3–142.3 |
|  | 1:9600 | 158.0 | 11.7 | 146.3–169.7 |
|  | 1:2400 | 340.1 | 44.4 | 295.7–384.5 |
|  | 1:1000 | 554.8 | 110.1 | 444.7–664.9 |
|  | 1:400 | 1025.2 | 84.6 | 940.7–1109.8 |
| 60° | 0 | 308.9 | 18.6 | 290.3–327.5 |
|  | 1:9600 | 352.3 | 9.6 | 342.7–361.9 |
|  | 1:2400 | 569.9 | 36.6 | 533.3–606.5 |
|  | 1:1000 | 1070.7 | 159.0 | 911.7–1229.7 |
|  | 1:400 | 1651.0 | 0.0 | 1651.0 |
| 70°* | 0 | 1300.0 | | |
|  | 1:9600 | 1372.0 | | |
|  | 1:2400 | 1482.0 | | |
|  | 1:1000 | 1649.0 | | |
|  | 1:400 | 1649.0 | | |

[a]Average mV signal from ten separate readings.
*Data represents single measurement at these angles.

At angles of incidence in the range of 30° to 40°, the thin film analyzer demonstrates excellent sensitivity, and the dynamic range observed is suitable for assays with a limited range requirement. The angles between 50° and 60° meet both the requirements of sensitivity and dynamic range. Background cannot be sufficiently minimized with a single polarizer for angles above 65°. This background could be reduced by electronic means. The dynamic range at these angles is sufficient to allow such correction mechanisms.

EXAMPLE 28

Comparison Ellipsometer Sensitivity for Strep A Assay

A Strep A assay protocol was developed which further enhances the readability of low positive samples. The sample (Strep A antigen) was mixed with conjugate and incubated 3 minutes at room temperature. An aliquot (20 µl) of this mixture was applied to the surface and incubated for 3 minutes. The rinse/dry protocol was performed as described above, either in the single use device or under a stream of nitrogen. Substrate was applied and incubated for 3 minutes, followed by the rinse/dry protocol. Results for an antigen dilution curve prepared with test surfaces with and without (visual - versus - non-visual) silicon nitride. Visual results were scored for increasing hues of purple from pale purple to dark blue. Surfaces without silicon nitride were reacted, rinsed, and dried without incorporation into a single use device. These surfaces were examined with a photodiode modified Comparison Ellipsometer. Readings were reported in millivolts and corrected for a background measurement. An eight fold increase in the performance of the Strep A OIA assay was observed with the instrumented detection based on an antigen dilution study. A total of 5 curves were examined.

TABLE 29

| Antigen Dilution | Visual | Average mV | 3SD | Range |
|---|---|---|---|---|
| 0 | — | 2.5 | 3.0 | −0.5–5.5 |
| 1:38400 | — | 16.8 | 6.6 | 10.2–23.4 |
| 1:19200 | — | 38.4 | 12.3 | 26.1–50.7 |
| 1:9600 | — | 54.5 | 11.7 | 42.8–66.2 |
| 1:4800 | 1+ | 161.3 | | |
| 1:2400 | 2+ | | | |
| 1:1600 | 5+ | | | |
| 1:1000 | 7+ | | | |
| 1:400 | 10+ | | | |

The test kit, the immunoassay device and the underlying coating and detection methods described herein are not intended to be limited by the assay format described or by the volumes, the concentrations or specific ingredients given for the various reagents, controls, and calibrators. It should be understood that similar chemical or other functional equivalents of the components used in the layer, layer coatings, or in any of the various reagents, additives, controls, and calibrators can be utilized within the scope of this invention.

The foregoing examples serve to illustrate the efficiency and utility of this technology to detect a variety of analytes using the pre-formed slide consisting of a substrate, AR material(s), activation, and receptive material(s) to produce an interference color change as a signal of analyte attachment.

Without being bound to the substrate formats or materials utilized in the preceding examples, it is possible to utilize a diversity of combinations of substrate formats and substrate materials which are functionally equivalent substitutes capable of having AR material bound to their surface, or are capable of being activated to allow attachment of the receptive material.

It is contemplated that the inventive concepts herein described may have differing embodiments and it is intended that the appended claims be construed to include all such alternative embodiments of the invention except insofar as they are limited by the prior art.

We claim:

1. A method for optimization of a visual signal of an optical assay device for the detection of an analyte, comprising the steps of:

(a) providing a substrate having a length and an anti-reflective film thereon with a plurality of thicknesses varied incrementally along the length of said substrate, providing an attachment layer of a chosen thickness on said anti-reflective film, providing a receptive layer of a chosen thickness for the analyte on said attachment layer, (b) contacting said analyte with said receptive layer under conditions such that a mass change on said receptive layer results, and (c) determining one or more thicknesses of said plurality of thicknesses of said anti-reflective film that in combination with the other layers of said device produces a visual signal comprising a maximized visual contrast in interference color upon said change in mass relative to a background interference color, over a range of concentrations of said analyte.

2. A method for optimization of a visual signal of an optical assay device for the detection of an analyte, comprising the steps of:

(a) providing a substrate having a length and an anti-reflective film thereon, providing an attachment layer on said substrate said attachment layer with a plurality of thicknesses varied incrementally along the length of said substrate, providing a receptive layer of a chosen thickness for the analyte on said attachment layer, (b) contacting said analyte with said receptive layer under conditions such that a mass change on said receptive layer results, and (c) determining one or more thicknesses of said plurality of thicknesses of said attachment layer that in combination with the other layers of said device produces a visual signal comprising a maximized visual contrast in interference color upon said change in mass relative to a background interference color, over a range of concentrations of said analyte.

3. A method for optimization of a visual signal of an optical assay device for the detection of an analyte, comprising the steps of:

(a) providing a substrate having a length and upon said substrate an anti-reflective film of an optimal thickness, providing an attachment layer on said substrate said attachment layer with a plurality of thicknesses varied incrementally along the length of said substrate, providing a receptive layer of a chosen thickness for the analyte on said attachment layer, (b) contacting said analyte with said receptive layer under conditions such that a mass change on said receptive layer results, and (c) determining one or more thicknesses of said plurality of thicknesses of said attachment layer that in combination with the other layers of said device produces a visual signal comprising a maximized visual contrast in interference color upon said change in mass relative to a background interference color, over a range of concentrations.

4. (Amended) A method for optimization of a visual signal of an optical assay device for the detection of an analyte, comprising the steps of:

(a) providing a substrate having a length and upon said substrate a first anti-reflective film of an optimal thickness and further providing a second anti-reflective film on said first anti-reflective film with a plurality of thicknesses varied incrementally along the length of said substrate, providing an attachment layer of a chosen thickness on said second anti-reflective film, providing a receptive layer of a chosen thickness for the analyte on said attachment layer, (b) contacting said analyte with said receptive layer under conditions such that a mass change on said receptive layer results, and (c) determining one or more thicknesses of said plurality of thicknesses of said second anti-reflective film that in combination with the other layers of said device produces a visual signal comprising a maximized visual contrast in interference color upon said change in mass relative to a background interference color, over a range of concentrations of said analyte.

5. A method for optimization of a visual signal of an optical assay device for the detection of an analyte, comprising the steps of:

(a) providing a substrate having a length and an anti-reflective film thereon with a plurality of thicknesses varied incrementally along the length of said substrate, providing on said anti-reflective film an attachment layer of an optimal thickness, providing a receptive layer of a chosen thickness for the analyte on said attachment layer, (b) contacting said analyte with said receptive layer under conditions such that a mass change on said receptive layer results, and (c) determining one or more thicknesses of said plurality of thicknesses of said anti-reflective film that in combination with the other layers of said device produces a visual signal comprising a maximized visual contrast in interference color upon said change in mass relative to a background interference color, over a range of concentrations of said analyte.

* * * * *